United States Patent
Ford et al.

(10) Patent No.: US 10,947,196 B2
(45) Date of Patent: Mar. 16, 2021

(54) BETA ADRENERGIC AGONIST AND METHODS OF USING THE SAME

(71) Applicant: CURASEN THERAPEUTICS, INC., San Mateo, CA (US)

(72) Inventors: Anthony P. Ford, San Mateo, CA (US); Wei Chen, Saratoga, CA (US); David Scott Carter, Sunnyvale, CA (US); Jiaxin Yu, Foster City, CA (US)

(73) Assignee: CuraSen Therapeutics, Inc., San Mateo, CA (US)

( * ) Notice: Subject to any disclaimer, the term of this patent is extended or adjusted under 35 U.S.C. 154(b) by 0 days.

(21) Appl. No.: 16/831,370

(22) Filed: Mar. 26, 2020

(65) Prior Publication Data
US 2020/0308115 A1    Oct. 1, 2020

Related U.S. Application Data

(60) Provisional application No. 62/934,482, filed on Nov. 12, 2019, provisional application No. 62/824,876, filed on Mar. 27, 2019.

(51) Int. Cl.
| | |
|---|---|
| *C07D 213/30* | (2006.01) |
| *C07D 209/42* | (2006.01) |
| *A61K 9/00* | (2006.01) |
| *A61P 25/30* | (2006.01) |
| *A61P 25/28* | (2006.01) |
| *A61P 25/16* | (2006.01) |

(52) U.S. Cl.
CPC .......... *C07D 209/42* (2013.01); *A61K 9/0019* (2013.01); *A61K 9/0034* (2013.01); *A61K 9/0073* (2013.01); *A61P 25/16* (2018.01); *A61P 25/28* (2018.01); *A61P 25/30* (2018.01)

(58) Field of Classification Search
CPC .................................................. C07D 213/30
USPC ......................................... 546/334; 514/357
See application file for complete search history.

(56) References Cited

U.S. PATENT DOCUMENTS

| | | | |
|---|---|---|---|
| 6,291,491 B1 * | 9/2001 | Weber ................. | C07D 417/12 514/357 |
| 2014/0194430 A1 | 7/2014 | Eis et al. | |

FOREIGN PATENT DOCUMENTS

| | | |
|---|---|---|
| EP | 0195397 A1 | 9/1986 |
| WO | WO 2019/053427 A1 | 3/2019 |

OTHER PUBLICATIONS

Dryuk et al., "Synthesis and, etc.," CA 118:118906 (Year: 1993).*
Dryuk, V. G. et al.: "*Synthesis and pesticidal activity of 2-methyl-5-oxiranylpyridine derivatives*"; Fiziologicheski Aktivaye Veshchestva, 1991, vol. 23, pp. 53-58. ISSN: 0533-1153.
International Search Report dated Jul. 24, 2020, regarding PCT/US2020/024948.
PUBCHEM, Substance Record for SID 33009977, Available Date: Dec. 5, 2007 [retrieved on May 11, 2020]. Retrieved from the Internet <URL: https://pubchem.ncbi.nlm.nih.gov/substance/33009977.
PUBCHEM, Substance Record for SID 35557804, Available Date: Dec. 5, 2007 [retrieved on Jun. 30, 2020]. Retrieved from the Internet <URL: https://pubchem.ncbi.nim.nih.gov/substance/35557804>.
Fragile X Syndrome—Harvard Health 2010 (https://www.health.harvard.edu/a_to_z/fragile-x-syndrome-a-to-z).
Down Syndrome Management and Treatment—Cleveland Clinic 2020 (https://my.clevelandclinic.org/health/diseases/17818-down-syndrome/management-and-treatment).
Down Syndrome Prevention—Cleveland Clinic 2020 (https://my.clevelandclinic.org/health/diseases/17818-down-syndrome/prevention.
Alzheimer's Disease Prevention: 7 Tips to Lower Your Risk of Getting Alzheimer's, 2020 (https://www.webmd.com/alzheimers/guide/understanding-alzheimers-disease-prevention#1).
Mayo Clinic Patient Care & Health information Diseases & Conditions Parkinson's Disease 2020 (https://www.mayoclinic.org/diseases-conditions/parkinsons-disease/symptoms-causes/syc-20376055).

* cited by examiner

*Primary Examiner* — Patricia L Morris
(74) *Attorney, Agent, or Firm* — DLA Piper LLP (US)

(57) ABSTRACT

The present disclosure is directed to chemical compounds and to the use of such compounds in the treatment of diseases associated with an adrenergic receptor.

6 Claims, 13 Drawing Sheets

BETA ADRENERGIC AGONIST AND METHODS OF USING THE SAME

CROSS-REFERENCE TO RELATED APPLICATIONS

This application claims the benefit of U.S. Provisional App. No. 62/824,876, filed on Mar. 27, 2019 and U.S. Provisional App. No. 62/934,482, filed Nov. 12, 2019, the content of each of which is hereby incorporated by reference.

FIELD

The present disclosure relates generally to chemical compounds and, in some embodiments, to beta adrenergic agonists and uses in the treatment of diseases associated with an adrenergic receptor.

BACKGROUND

PCT Application Publication Number WO 2017/197324 discloses "[a]drenergic receptor modulating compounds and methods . . . of treating a subject for a disease or condition associated with an adrenergic receptor including administering a therapeutically effective amount of the subject compound."

United States Patent Application Publication Number 2013/0096126 discloses "a method for enhancing learning or memory of both in a mammal having impaired learning or memory or both from a neuro-degenerative disorder, which entails the step of administering at least one compound or a salt thereof which is a β1-adrenergic receptor agonist, partial agonist or receptor ligand in an amount effective to improve the learning or memory or both of said mammal."

United States Patent Application Publication Number 2014/0235726 discloses "a method of improving cognition in a patient with Down syndrome, which entails administering one or more β2 adrenergic receptor agonists to the patient in an amount and with a frequency effective to improve cognition of the patient as measured by contextual learning tests."

United States Patent Application Publication Number 2016/0184241 discloses "a method of improving cognition in a patient with Down syndrome, which entails intranasally administering one or more β2-ADR agonists or pharmaceutically-acceptable salts of either or both to the patient in an amount and with a frequency effective to improve cognition of the patient as measured contextual learning tests."

SUMMARY

The present disclosure is based at least in part on the identification of compounds that modulate adrenergic receptor and methods of using the same to treat diseases associated with an adrenergic receptor. Disclosed herein is a compound according to Formula (I) or an optically pure stereoisomer, pharmaceutically acceptable salt, solvate, or prodrug thereof Formula (I)

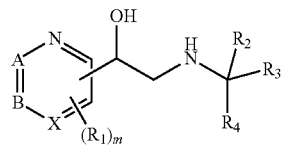

In some embodiments, each A, B, and X is independently a nitrogen or carbon. In some embodiments, each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, and unsubstituted or substituted heteroaryl. In some embodiments, m is an integer selected from 0 to 4.

In some embodiments, $R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

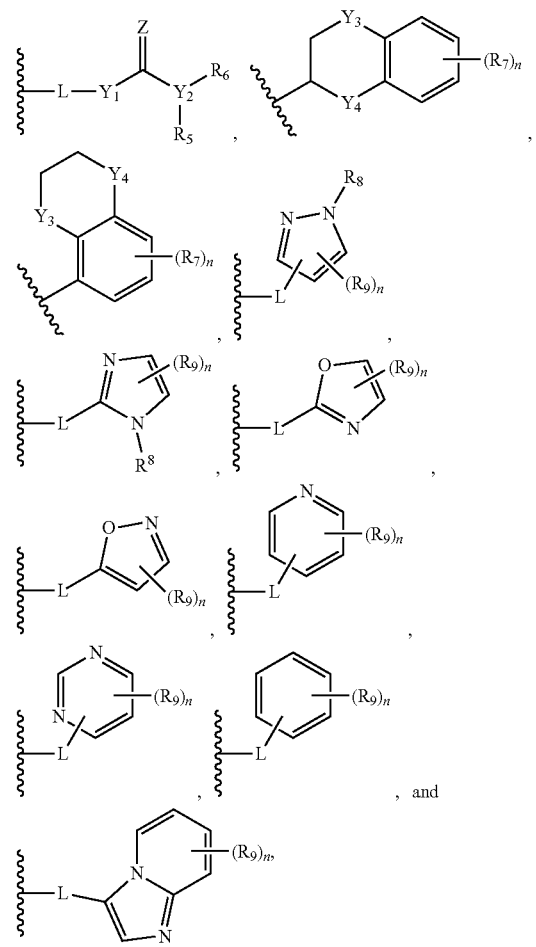

or $R_2$ and $R_3$ together with the carbon form an unsubstituted or substituted 3-7 membered cycloalkyl or heterocycle ring.

In some embodiments, L is a C1-C5 alkyl linker optionally substituted, each $Y_1$, $Y_2$, $Y_3$, and $Y_4$ is independently a covalent bond, a carbon, an oxygen, or a nitrogen, optionally substituted with hydrogen, unsubstituted or substituted alkyl, or unsubstituted or substituted cycloalkyl, and Z is O or S.

In some embodiments, $R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl.

In some embodiments, n is an integer selected from 0 to 4, $R_8$ is selected from the group consisting of hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, and unsubstituted or substituted amino.

Also disclosed herein is a compound according to Formula (II) or an optically pure stereoisomer, pharmaceutically acceptable salt, solvate, or prodrug thereof Formula (II)

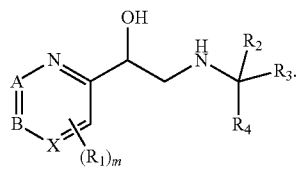

In some embodiments, each A, B, and X is independently a nitrogen or carbon. In some embodiments, each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, and unsubstituted or substituted heteroaryl. In some embodiments, m is an integer selected from 0 to 4.

In some embodiments, $R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

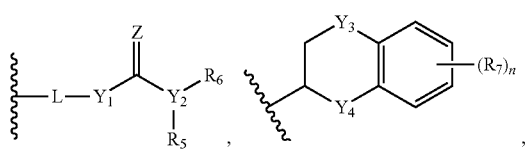

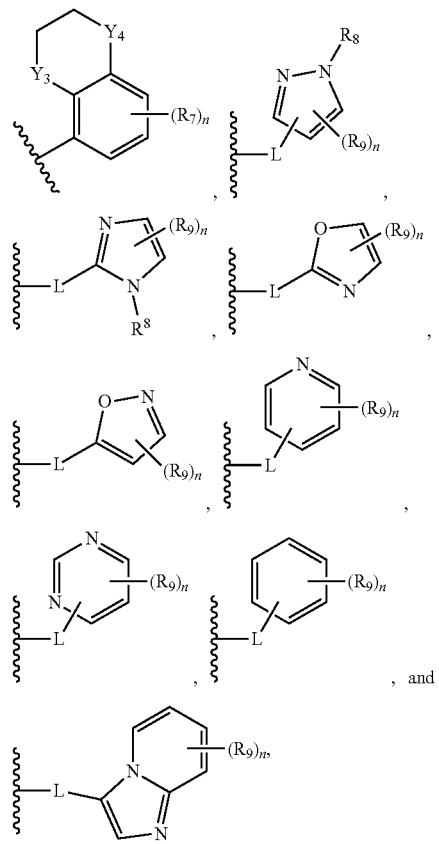

or $R_2$ and $R_3$ together with the carbon form an unsubstituted or substituted 3-7 membered cycloalkyl or heterocycle ring.

In some embodiments, L is a C1-C5 alkyl linker optionally substituted, each $Y_1$, $Y_2$, $Y_3$, and $Y_4$ is independently a covalent bond, a carbon, an oxygen, or a nitrogen, optionally substituted with hydrogen, unsubstituted or substituted alkyl, or unsubstituted or substituted cycloalkyl, and Z is O or S.

In some embodiments, $R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl.

In some embodiments, n is an integer selected from 0 to 4, $R_8$ is selected from the group consisting of hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, and unsubstituted or substituted amino.

Further disclosed herein is a compound according to Formula (III) or an optically pure stereoisomer, pharmaceutically acceptable salt, solvate, or prodrug thereof

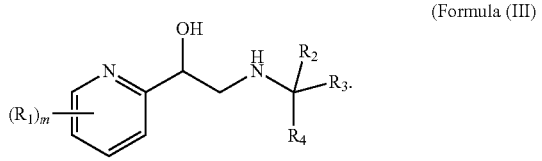
(Formula (III))

In some embodiments, each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)— alkyl, unsubstituted or substituted —(C=O)-cycloalkyl, unsubstituted or substituted —(C=O)-aryl, unsubstituted or substituted —(C=O)-heteroaryl, unsubstituted or substituted aryl, and unsubstituted or substituted heteroaryl. m is an integer selected from 0 to 4.

In some embodiments, $R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

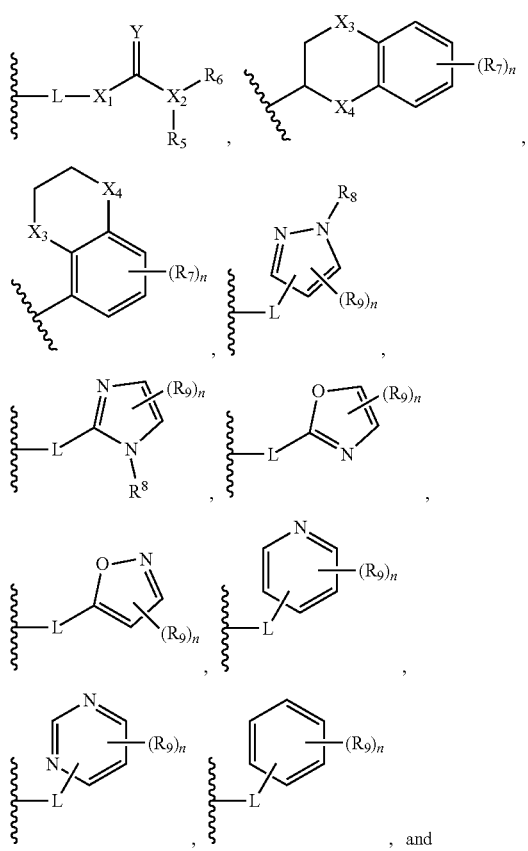
, and

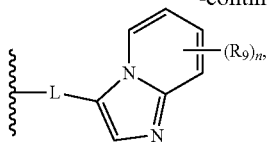

or $R_2$ and $R_3$ together with the carbon form an unsubstituted or substituted 3-7 membered cycloalkyl or heterocycle ring.

In some embodiments, L is a C1-C5 alkyl linker optionally substituted, each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cycloalkyl, and Y is O or S.

In some embodiments, $R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl.

In some embodiments, n is an integer selected from 0 to 4, $R_8$ is selected from the group consisting of hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, and unsubstituted or substituted amino.

Further disclosed herein is a compound according to Formula (I'):

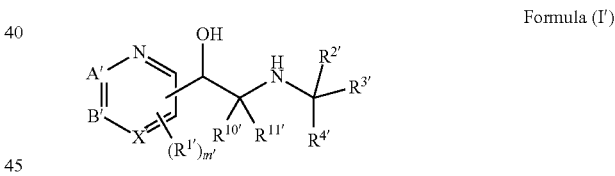
Formula (I')

or a pharmaceutically acceptable salt thereof,
wherein:
A', B', and X' are each independently nitrogen or carbon;
each $R^{1'}$ is independently halogen, —R', —CN, —NO$_2$, —SF$_5$, —OR$^x$, —NR$^x{}_2$, —NHR$^x$, —SO$_2$R', —C(O)R', —C(O)NR'$_2$;
each R' is independently hydrogen or an optionally substituted group selected from: C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;
each R$^x$ is independently an optionally substituted group selected from: C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

$R^{2'}$, $R^{3'}$, and $R^{4'}$ are each independently halogen, —R', —CN, —NO$_2$, —OR', —NR'$_2$,

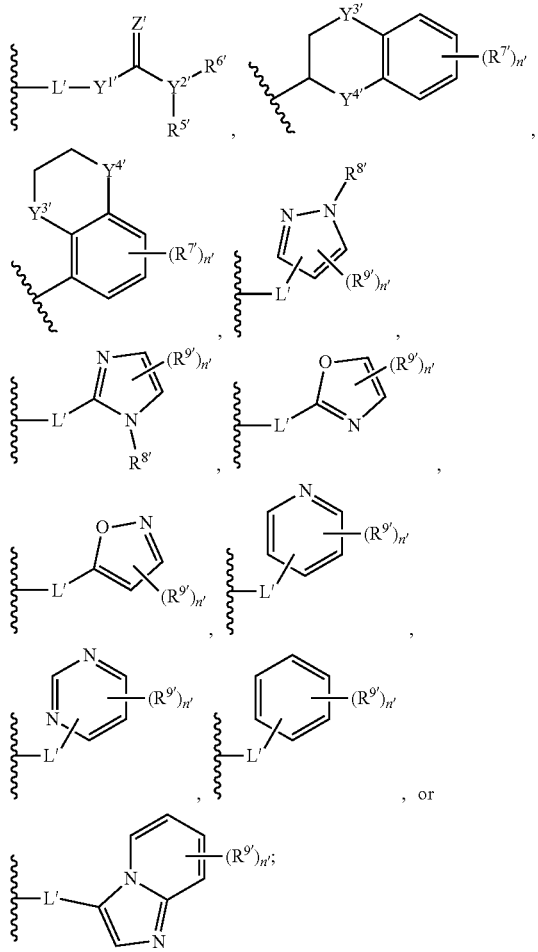

or $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted C1-5 alkylene;

$Y^{1'}$, $Y^{2'}$, $Y^{3'}$, and $Y^{4'}$ are each independently a covalent bond, a carbon, an oxygen, or a nitrogen, optionally substituted with hydrogen, an optionally substituted $C_{1-6}$ alkyl, or an optionally substituted 3-7 membered saturated carbocyclic ring;

Z' is O or S;

$R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{7'}$ is independently —R', halogen, —CN, —NO$_2$, —NR'$_2$, or —OR';

n' is an integer selected from 0 to 4;

$R^{8'}$ is hydrogen, —CN, optionally substituted alkyl, or an optionally substituted aryl ring; and each $R^{9'}$ is independently hydrogen, halogen, —CN, —NR'$_2$, or optionally substituted alkyl; and $R^{10'}$ and $R^{11'}$ are each independently hydrogen or optionally substituted $C_{1-2}$ aliphatic.

Further disclosed herein is a compound according to Formula (I"):

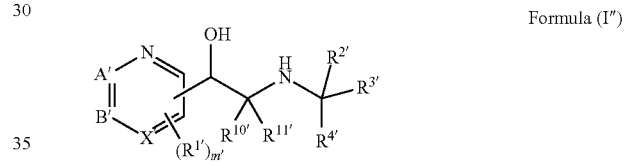

Formula (I")

or a pharmaceutically acceptable salt thereof, wherein:

A', B', and X' are each independently nitrogen or carbon;

each $R^{1'}$ is independently halogen, —R', —CN, —NO$_2$, —SF$_5$, —NR$^x$$_2$, —NHR$^x$, —SO$_2$R', —C(O)R', —C(O)NR'$_2$, —NR'C(O)R', —NR'CO$_2$R', or —CO$_2$R';

each R' is independently hydrogen or an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each $R^x$ is independently an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

R$^{2'}$, R$^{3'}$, and R$^{4'}$ are each independently halogen, —R', —CN, —NO$_2$, —OR', —NR'$_2$,

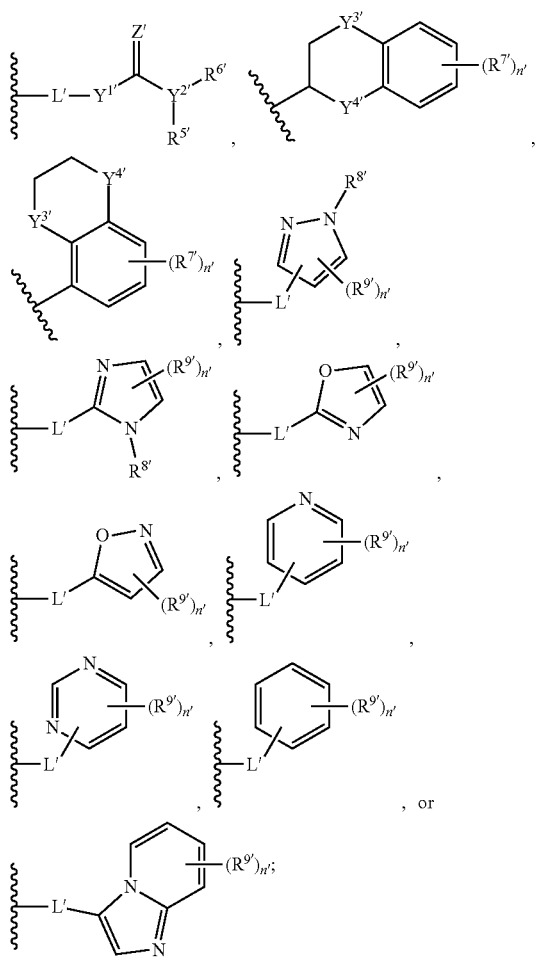

or

R$^{2'}$ and R$^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted C$_{1-5}$ alkylene;

Y$^{1'}$, Y$^{2'}$, Y$^{3'}$, and Y$^{4'}$ are each independently a covalent bond, a carbon, an oxygen, or a nitrogen, optionally substituted with hydrogen, an optionally substituted C$_{1-6}$ alkyl, or an optionally substituted 3-7 membered saturated carbocyclic ring;

Z' is O or S;

R$^{5'}$ and R$^{6'}$ are each independently hydrogen or optionally substituted alkyl, or R$^{5'}$ and R$^{6'}$ are cyclically linked and, together with Y$^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each R$^{7'}$ is independently —R', halogen, —CN, —NO$_2$, —NR'$_2$, or —OR';

n' is an integer selected from 0 to 4;

R$^{8'}$ is hydrogen, —CN, optionally substituted alkyl, or an optionally substituted aryl ring; and each R$^{9'}$ is independently hydrogen, halogen, —CN, —NR'$_2$, or optionally substituted alkyl; and R$^{10'}$ and R$^{11'}$ are each independently hydrogen or optionally substituted C$_{1-2}$ aliphatic.

Further disclosed herein is a compound with the following structure:

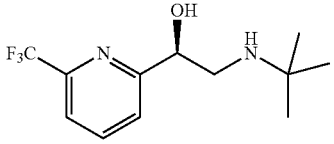

or a pharmaceutically acceptable salt thereof.

Further disclosed herein is a compound with the following structure:

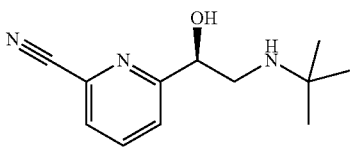

or a pharmaceutically acceptable salt thereof.

Further disclosed herein is a compound with the following structure:

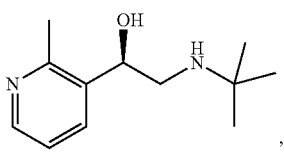

or a pharmaceutically acceptable salt thereof.

Also disclosed herein is a pharmaceutical composition including a compound as disclosed herein, i.e., a compound with a structure of Formula (I), Formula (II), Formula (III), Formula (I'), Formula (I''), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), and Formula (XXV'), and a pharmaceutically acceptable excipient.

In certain embodiments a compound as disclosed herein is an agonist, partial agonist or antagonist of an adrenergic receptor; in some embodiments the compound is a β1-adrenergic receptor agonist, β2-adrenertic receptor agonist or non-selective β1/β2-adrenergic receptor agonist; in some embodiments the compound is a β1-adrenergic receptor agonist; in some embodiments the compound is a β2-adrenergic receptor agonist; in some embodiments the compound is a compound is a non-selective β1/β2-adrenergic agonist.

Further disclosed is a method of treating a subject with a disease, the method including administering to the subject a therapeutically effective amount of a compound as disclosed herein, i.e., a compound with a structure of Formula (I), Formula (I"), Formula (II), Formula (III), Formula (I'), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), or Formula (XXV'). In some embodiments, the disease is a disease associated with an adrenergic receptor. In some embodiments, the disease is a neurodegenerative disease. In some embodiments, the subject is a human.

In some embodiments, the disease is selected from myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis. In some embodiments, the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

In some embodiments, the disease is a neurodegenerative disease that is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS). In some embodiments the disease is a neurodegenerative disease that is one or more selected from the group consisting of MCI, aMCI, Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS (Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), and ADHD (attention deficit hyperactivity disorder). In some embodiments the subject does not have Alzheimer's disease (AD). In some embodiments the subject does not have Down Syndrome.

In certain embodiments of the methods disclosed herein, the methods include administering to the subject a compound as disclosed herein and a peripherally acting β-blocker (PABRA).

As used herein, the term "peripherally acting β-blocker (PABRA)" means a β adrenergic receptor antagonist or simply a β1-, β2- or non-selective β-blocker. Examples of selective peripherally acting β-blockers (PABRA) that may in certain embodiments be used in the methods disclosed herein include nadolol, atenolol, sotalol and labetalol. In certain embodiments a β-blocker that can be used in the methods herein is one or more selected from the group consisting of acebutolol, betaxolol, bisoprolol, celiprolol, esmolol, metaprolol and nevivolol; in other embodiments the methods do not use acebutolol, betaxolol, bisoprolol, celiprolol, esmolol, metaprolol or nevivolol as a β-blocker.

In certain embodiments a peripherally acting β-blocker (PABRA) is administered to the subject prior to administration of a compound of the disclosure; in other embodiments a peripherally acting β-blocker (PABRA) is administered to the subject concurrently with the administration of a compound of the disclosure.

In certain embodiments of the compositions and methods provided herein, one or more peripherally acting β-blockers (PABRA) are administered prior to or concurrently with a compound of the disclosure in order to inhibit or preclude agonism of peripheral β1 and/or β2 adrenergic receptors by a compound of the disclosure. In various embodiments it is preferred to block peripheral β1 and/or β2 adrenergic receptors in accordance with the compositions and methods of the present disclosure in order to preclude, or at least minimize, any adverse peripheral cardiac, metabolic or muscular effects on humans being treated.

In some embodiments of the methods provided herein, a β1 agonist and or a β2 agonist, or a non-selective β1/β2 agonist is administered to the patient in addition to a compound as disclosed herein.

As used herein, the term "β1 agonist" is used to mean β1-adrenergic receptor agonist or β1-ADR agonist. In certain embodiments the term β1 agonist is understood to include compounds that are primarily β1 agonists, but which may also exhibit some peripheral agonism for other adrenergic receptors, such as β2-adrenergic receptors. In this application, the terms β1-adrenergic receptor agonist", "β1-ADR agonist", "β1AR agonist" and β1 agonist" may be used interchangeably. In certain embodiments, the term β1-ADR agonist expressly includes both selective and partial agonists, as well as biased and non-biased agonists. Examples of β1 adrenergic agonists include, for example, xamoterol, noradrenalin, isoprenaline, dopamine, pindolol and dobutamine and the pharmaceutically-acceptable salts of any of the above. Partial agonists and ligands of the β1-ADR are known. Further, using the methodology of Kolb et al, but for β1-ADR instead, one skilled in the art could determine new ligands by structure-based discovery. See *Proc. Natl. Acad. Sci. USA* 2009, 106, 6843-648.

As used herein, the term β2 agonist is used to mean β2-adrenergic receptor agonist or β2-ADR agonist. In certain embodiments, the term β2 agonist is understood to include compounds that are primarily β2 agonists, but which may also exhibit some peripheral agonism for other adrenergic receptors, such as β1-adrenergic receptors. In this application the terms "β2-adrenergic receptor agonist", "β2-ADR agonist", "β2AR agonist" and "β2 agonist" may be used interchangeably. In some embodiments the term β2-ADR agonist expressly includes both selective and partial agonists. β2 agonists that may be used in accordance with various aspects and embodiments of the present disclosure may be short-acting, long-acting or ultra long-acting. Examples of short-acting β2 agonists that may be used are salbutamol, levosalbutamol, terbutaline, pirbuterol, procaterol, metaproterenol, bitolterol mesylate, oritodrine, isoprenaline, salmefamol, fenoterol, terbutaline, albuterol, and isoetharine. Examples of long-acting β2 agonists that may be used are salmeterol, bambuterol, formoterol and clenbuterol. Examples of ultra long-acting β2 agonists include indacaterol, vilanterol and olodaterol.

It was surprisingly found that compounds of the present disclosure exhibit unexpectedly beneficial properties, as demonstrated in the Examples section herein. For instance, it was surprisingly found that compounds of the present disclosure act as low nM (<10 nM) partial agonists of the β2 adrenergic receptor. Furthermore, compounds of the present disclosure exhibit an unexpectedly high ability to cross the blood brain barrier and accumulate in the cerebral spinal fluid. Additionally, compounds of the present disclosure exhibit excellent oral bioavailability and stability, while simultaneously exhibiting low toxicity and a low potential for drug-drug interactions.

DETAILED DESCRIPTION

Figure 1:
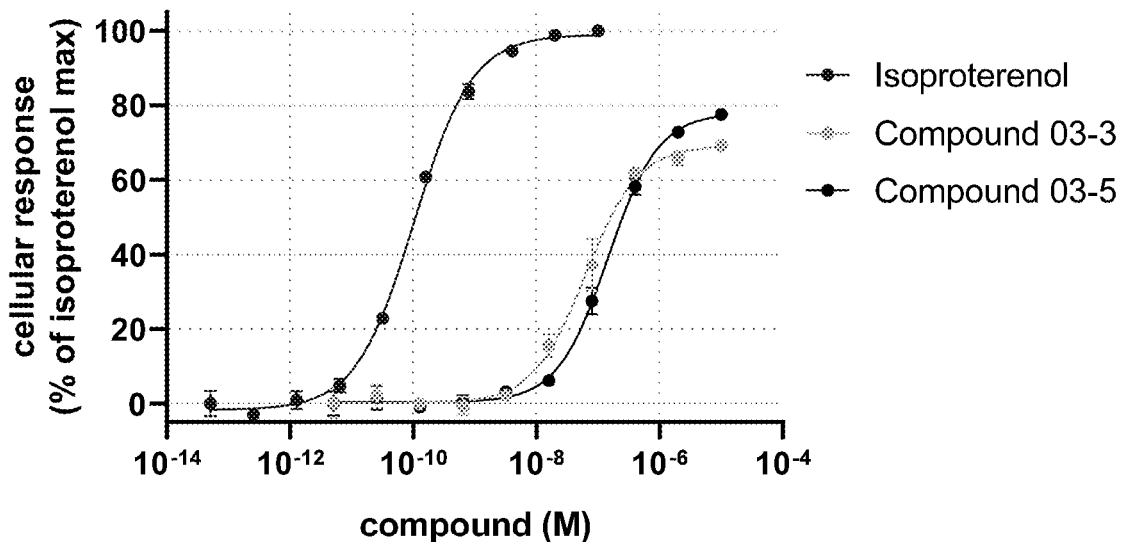
FIG. 1 summarizes the concentration dependent inhibition of Compounds 03-3 and 03-5 in (31 expressing CHO cells with isoproterenol as control.

In the following detailed description of the embodiments of the instant disclosure, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the instant disclosure.

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements. The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment. A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art. All publications, patent applications, patents, and other references mentioned herein are incorporated by reference in their entirety. All sequences provided in the disclosed Genbank Accession numbers are incorporated herein by reference as available on Aug. 11, 2011. In case of conflict, the present specification, including explanations of terms, will control. In addition, the materials, methods, and examples are illustrative only and not intended to be limiting.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multicyclic ring systems include, but are not limited to, bicyclo[4.4.0]decane, bicyclo[2.2.1]heptane, spiro[2.2]pentane, and the like. (Cycloalkyl)oxy refers to —O-cycloalkyl. (Cycloalkyl)thio refers to —S-cycloalkyl. This term also encompasses oxidized forms of sulfur, such as —S(O)—cycloalkyl, or —S(O)$_2$-cycloalkyl.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, —CH=CH(CH$_3$), —CH=C(CH$_3$)$_2$, —C(CH$_3$)=CH$_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and —C≡C(CH$_3$), among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups. Aryloxy refers to —O-aryl. Arylthio refers to —S-aryl, wherein aryl is as defined herein. This term also encompasses oxidized forms of sulfur, such as —S(O)-aryl, or —S(O)$_2$-aryl. Heteroaryloxy refers to —O-heteroaryl. Heteroarylthio refers to —S-heteroaryl. This term also encompasses oxidized forms of sulfur, such as —S(O)-heteroaryl, or —S(O)$_2$-heteoaryl.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups. Heterocyclyloxy refers to —O-heterocycyl. Heterocyclylthio refers to —S-heterocycyl. This term also encompasses oxidized forms of sulfur, such as —S(O)-heterocyclyl, or —S(O)$_2$-heterocyclyl.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —NO$_2$; cyano group refers to —CN; isocyano group refers to —N≡C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

As described herein, compounds of the present disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-40}$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-40}$(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; N(R°)N(R°)C(O)R°; —N(R°)N(R°)C(O)NR°$_2$; —N(R° N(R°)C(O)OR°; —(CH$_2$)$_{0-4}$C(O) R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O) (CH$_2$)$_{0-4}$SR°; SC(S)SR'; —(CH$_2$)$_{0-4}$SC(O)R°; —(CH$_2$)$_{0-4}$C(O)NR°$_2$; —C(S)NR°$_2$; —C(S)SR°; —SC(S)SR°; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-40}$S(O)$_2$R°; —S(O)$_2$NR°$_2$; —S(O)(NR°)R°; —S(O)$_2$N═C(NR°$_2$)$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched) alkylene)O—N(R°)$_2$; or —(C$_{1-4}$ straight or branched)alkylene)C(O)O—N(R°$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$; -(haloR$^\bullet$); —(CH$_2$)$_{0-2}$OH; —(CH$_2$)$_{0-2}$OR$^\bullet$; —(CH$_2$)$_{0-2}$CH(OR$^\bullet$)$_2$; —O(haloR$^\bullet$); —CN; —N$_3$; —(CH$_2$)$_{0-2}$C(O)R$^\bullet$; —(CH$_2$)$_{0-2}$C(O)OH; —(CH$_2$)$_{0-2}$C(O)OR$^\bullet$; —(CH$_2$)$_{0-2}$ SR$^\bullet$; —(CH$_2$)$_{0-2}$ SH; —(CH$_2$)$_{0-2}$NH$_2$; —(CH$_2$)$_{0-2}$NHR$^\bullet$; —(CH$_2$)$_{0-2}$NR$^\bullet_2$; —NO$_2$, —SiR$^\bullet_3$; —OSiR$^\bullet_3$; —C(O)SR$^\bullet$; —(C$_{1-4}$ straight or branched alkylene)C(O)OR$^\bullet$; or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-2}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O; ═S; ═NNR*$_2$; ═NNHC(O)R*; ═NNHC(O)OR*; ═NNHS(O)$_2$R*; ═NR*; ═NOR*; —O(C(R*$_2$))$_{2-3}$O—; or —S(C(R*$_2$))$_{2-3}$S—; wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$; -(haloR$^\bullet$); —OH, —OR$^\bullet$; —O(haloR$^\bullet$); —CN; —C(O)OH; —C(O)OR$^\bullet$; —NH$_2$; —NHR$^\bullet$; —NR$^\bullet_2$; or —NO$_2$; wherein each R$^\bullet$ is unsubstituted or where preceded by "halo" is substituted only with one or more halogens, and is independently C$_{1-4}$ aliphatic, —CH$_2$Ph; —O(CH$_2$)$_{0-1}$ Ph; or a 5-6-membered saturated; partially unsaturated; or aryl ring having 0-4 heteroatoms independently selected from nitrogen, oxygen, or sulfur.

Suitable substituents on a substitutable nitrogen of an "optionally substituted" group include —R$^\dagger$; —NR$^\dagger_2$; —C(O)R$^\dagger$; —C(O)OR$^\dagger$; —C(O)C(O)R$^\dagger$; C(O)CH$_2$C(O)R$^\dagger$;

—S(O)$_2$R$^\dagger$; —S(O)$_2$NR$^\dagger_2$; —C(S)NR$^\dagger_2$; —C(NH)NR$^\dagger_2$; or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R˙; -(haloR˙); —OH; —OR˙; —O(haloR˙); —CN; —C(O)OH; —C(O)OR˙; —NH$_2$; —NHR˙; —NR˙$_2$; or —NO$_2$; wherein each R' is unsubstituted or where preceded by "halo" is substituted only with one or more halogens, and is independently C$_{1-4}$ aliphatic, —CH$_2$Ph; —O(CH$_2$)$_{0-1}$Ph; or a 5-6-membered saturated; partially unsaturated; or aryl ring having 0-4 heteroatoms independently selected from nitrogen, oxygen, or sulfur.

Thiol refers to —SH. Thiocarbonyl refers to (=S). Sulfonyl refers to —SO$_2$-alkyl, —SO$_2$-substituted alkyl, —SO$_2$-cyclo alkyl, —SO$_2$-substituted cycloalkyl, —SO$_2$-aryl, —SO$_2$— substituted aryl, —SO$_2$-heteroaryl, —SO$_2$-substituted heteroaryl, —SO$_2$-heterocyclyl, and —SO$_2$— substituted heterocyclyl. Sulfonylamino refers to —NR$^a$SO$_2$alkyl, —NR$^a$SO$_2$-substituted alkyl, —NR$^a$SO$_2$cycloalkyl, —NR$^a$SO$_2$substituted cycloalkyl, —NR$^a$SO$_2$aryl, —NR$^a$SO$_2$substituted aryl, —NR$^a$SO$_2$heteroaryl, —NR$^a$SO$_2$ substituted heteroaryl, —NR$^a$SO$_2$heterocyclyl, —NR$^a$SO$_2$ substituted heterocyclyl, wherein each R$^a$ independently is as defined herein.

Carboxyl refers to —COOH or salts thereof. Carboxyester refers to —C(O)O-alkyl, —C(O)O— substituted alkyl, —C(O)O-aryl, —C(O)O-substituted aryl, —C(O)β-cycloalkyl, —C(O)O— substituted cycloalkyl, —C(O)O-heteroaryl, —C(O)O-substituted heteroaryl, —C(O)O— heterocyclyl, and —C(O)O-substituted heterocyclyl. (Carboxyester)amino refers to —NR$^a$—C(O)O-alkyl, —NR$^a$—C(O)O-substituted alkyl, —NR$^a$—C(O)O-aryl, —NR$^a$—C(O)O-substituted aryl, —NR$^a$—C(O)β-cycloalkyl, —NR$^a$—C(O)O-substituted cycloalkyl, —NR$^a$—C(O)O-heteroaryl, —NR$^a$—C(O)O-substituted heteroaryl, —NR$^a$—C(O)O-heterocyclyl, and —NR$^a$—C(O)O-substituted heterocyclyl, wherein R$^a$ is as recited herein. (Carboxyester)oxy refers to —O—C(O)O-alkyl, —O—C(O)O— substituted alkyl, —O—C(O)O-aryl, —O—C(O)O-substituted aryl, —O—C(O)β-cycloalkyl, —O—C(O)O-substituted cycloalkyl, O—C(O)O-heteroaryl, —O—C(O)O-substituted heteroaryl, —O—C(O)O-heterocyclyl, and —O—C(O)O-substituted heterocyclyl. Oxo refers to (=O).

The terms "amine" and "amino" refer to derivatives of ammonia, wherein one of more hydrogen atoms have been replaced by a substituent which include, but are not limited to alkyl, alkenyl, aryl, and heterocyclyl groups. In some embodiments, substituted amino can include —NH—CO—R. Carbamate groups refers to —O(C=O)NR$_1$R$_2$, where R$_1$ and R$_2$ are independently hydrogen, aliphatic groups, aryl groups, or heterocyclyl groups.

Aminocarbonyl refers to —C(O)N(R$^b$)$_2$, wherein each R$^b$ independently is selected from hydrogen, alkyl, substituted alkyl, aryl, substituted aryl, cycloalkyl, substituted cycloalkyl, heterocyclyl, substituted heterocyclyl. Also, each R$^b$ may optionally be joined together with the nitrogen bound thereto to form a heterocyclyl or substituted heterocyclyl group, provided that both R$^b$ are not both hydrogen. Aminocarbonylalkyl refers to -alkylC(O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not both hydrogen. Aminocarbonylamino refers to —NR$^a$C(O)N(R$^b$)$_2$, wherein R$^b$ and each R$^b$ are as defined herein. Aminodicarbonylamino refers to —NR$^a$C(O)C(O)N(R$^b$)$_2$, wherein R$^a$ and each R$^b$ are as defined herein Aminocarbonyloxy refers to —O—C(O)N(R$^b$)$_2$, wherein each R$^b$ independently is as defined herein Aminosulfonyl refers to —SO$_2$N(R$^b$)$_2$, wherein each R$^b$ independently is as defined herein.

Imino refers to —N=R$^c$ wherein R$^c$ may be selected from hydrogen, aminocarbonylalkyloxy, substituted aminocarbonylalkyloxy, aminocarbonylalkylamino, and substituted aminocarbonylalkylamino Additionally, unless otherwise stated, structures depicted herein are also meant to include compounds that differ only in the presence of one or more isotopically enriched atoms. For example, compounds having the present structures including the replacement of hydrogen by deuterium (e.g., D or H$^2$) or tritium (e.g., T or H$^3$), or the replacement of a carbon by a $^{13}$C- or $^{14}$C-enriched carbon are included and are within the scope of this invention. Such compounds are useful, for example, as analytical tools, as probes in biological assays, or as therapeutic agents in accordance with the present invention Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)).

Disclosed herein is a compound according to Formula (I) or an optically pure stereoisomer, pharmaceutically acceptable salt, solvate, or prodrug thereof

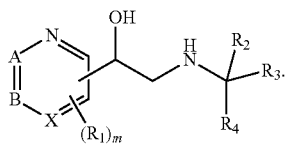

Formula (I)

Each A, B, and X can be independently a nitrogen or carbon. Each $R_1$ can be independently hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, or unsubstituted or substituted heteroaryl. m can be an integer selected from 0 to 4.

$R_2$, $R_3$, and $R_4$ can be independently H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

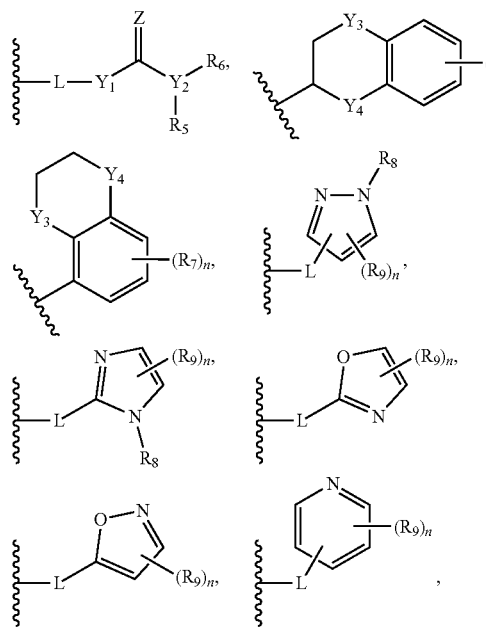

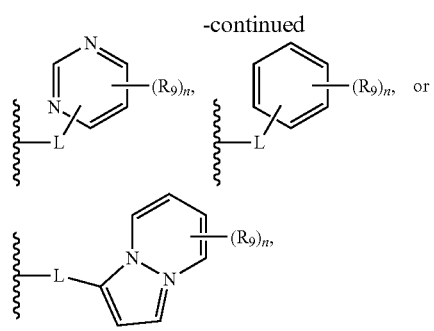

or $R_2$ and $R_3$ together with the carbon can form an unsubstituted or substituted 3-7 membered cycloalkyl or heterocycle ring.

L can be a C1-C5 alkyl linker optionally substituted, each $Y_1$, $Y_2$, $Y_3$, and $Y_4$ can be independently a covalent bond, a carbon, an oxygen, or a nitrogen, optionally substituted with hydrogen, unsubstituted or substituted alkyl, or unsubstituted or substituted cycloalkyl, and Z can be O or S.

$R_5$ and $R_6$ can be independently hydrogen, unsubstituted or substituted alkyl, or $R_5$ and $R_6$ are cyclically linked and together with $Y_2$ to form an optionally substituted cycloalkyl or heterocycle, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, or unsubstituted or substituted heteroaryl.

n can be an integer selected from 0 to 4, $R_8$ can be hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, or unsubstituted or substituted amino.

Also disclosed herein is a compound according to Formula (II) or an optically pure stereoisomer, pharmaceutically acceptable salt, solvate, or prodrug thereof

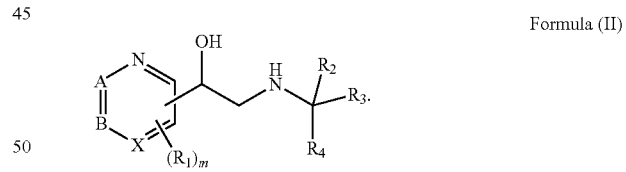

Formula (II)

Each A, B, and X can be independently a nitrogen or carbon. Each $R_1$ can be hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, or unsubstituted or substituted heteroaryl. m can be an integer selected from 0 to 4.

$R_2$, $R_3$, and $R_4$ can be independently H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

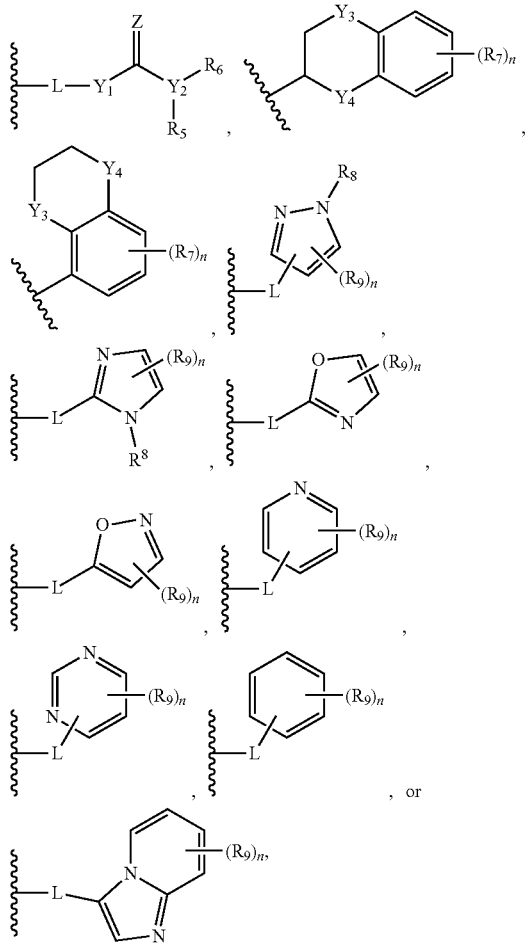

or $R_2$ and $R_3$ together with the carbon can form an unsubstituted or substituted 3-7 membered cycloalkyl or heterocycle ring.

L can be a C1-C5 alkyl linker optionally substituted, each $Y_1$, $Y_2$, $Y_3$, and $Y_4$ can be independently a covalent bond, a carbon, an oxygen, or a nitrogen, optionally substituted with hydrogen, unsubstituted or substituted alkyl, or unsubstituted or substituted cycloalkyl, and Z can be O or S.

$R_5$ and $R_6$ can be independently hydrogen, unsubstituted or substituted alkyl, or $R_5$ and $R_6$ can be cyclically linked and together with $Y_2$ to form an optionally substituted cycloalkyl or heterocycle, each $R_7$ can be hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, or unsubstituted or substituted heteroaryl.

n can be an integer selected from 0 to 4, $R_8$ can be hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, or unsubstituted or substituted amino.

Further disclosed herein is a compound according to Formula (III) or an optically pure stereoisomer, pharmaceutically acceptable salt, solvate, or prodrug thereof

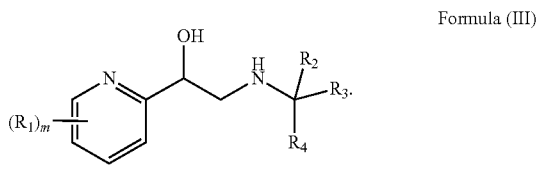

Formula (III)

Each $R_1$ can be independently hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, or unsubstituted or substituted heteroaryl. m can be an integer selected from 0 to 4.

$R_2$, $R_3$, and $R_4$ can be independently H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

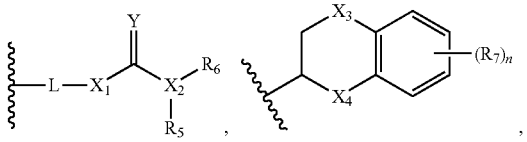

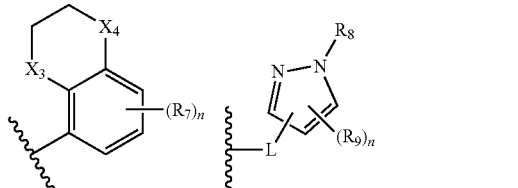

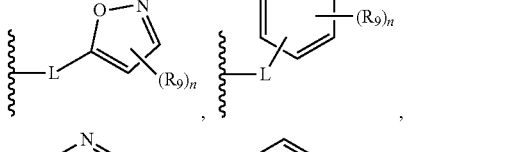

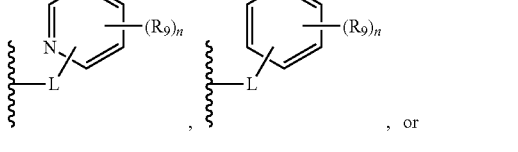

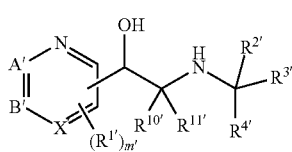

or $R_2$ and $R_3$ together with the carbon can form an unsubstituted or substituted 3-7 membered cycloalkyl or heterocycle ring.

L can be a C1-C5 alkyl linker optionally substituted, each $X_1$, $X_2$, $X_3$, and $X_4$ can be independently a covalent bond, a carbon, an oxygen, or a nitrogen, optionally substituted with hydrogen, unsubstituted or substituted alkyl, or unsubstituted or substituted cycloalkyl, and Y can be O or S.

$R_5$ and $R_6$ can be independently hydrogen, unsubstituted or substituted alkyl, or $R_5$ and $R_6$ can be cyclically linked and together with $Y_2$ to form an optionally substituted cycloalkyl or heterocycle, each $R_7$ can be independently hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cyclo alkyl, unsubstituted or substituted aryl, or unsubstituted or substituted heteroaryl.

n can be an integer selected from 0 to 4, $R_8$ can be hydrogen, cyano, unsubstituted or substituted alkyl, and unsubstituted or substituted aryl, and $R_9$ is selected from the group consisting of hydrogen, halogen, cyano, unsubstituted or substituted alkyl, unsubstituted or substituted alkoxy, or unsubstituted or substituted amino.

Further disclosed herein is a compound according to Formula (I'):

Formula (I')

or a pharmaceutically acceptable salt thereof,
wherein:
A', B', and X' are each independently nitrogen or carbon;
each $R^{1'}$ is independently halogen, —R', —CN, —NO$_2$, —SF$_5$, —OR$^x$, —NR$^x{}_2$, —NHR$^x$, —SO$_2$R', —C(O)R', —C(O)NR'$_2$;
each R' is independently hydrogen or an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;
each R$^x$ is independently an optionally substituted group selected from: $C_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;
m' is an integer selected from 0 to 4;
$R^{2'}$, $R^{3'}$, and $R^{4'}$ are each independently halogen, —R', —CN, —NO$_2$, —OR', —NR'$_2$,

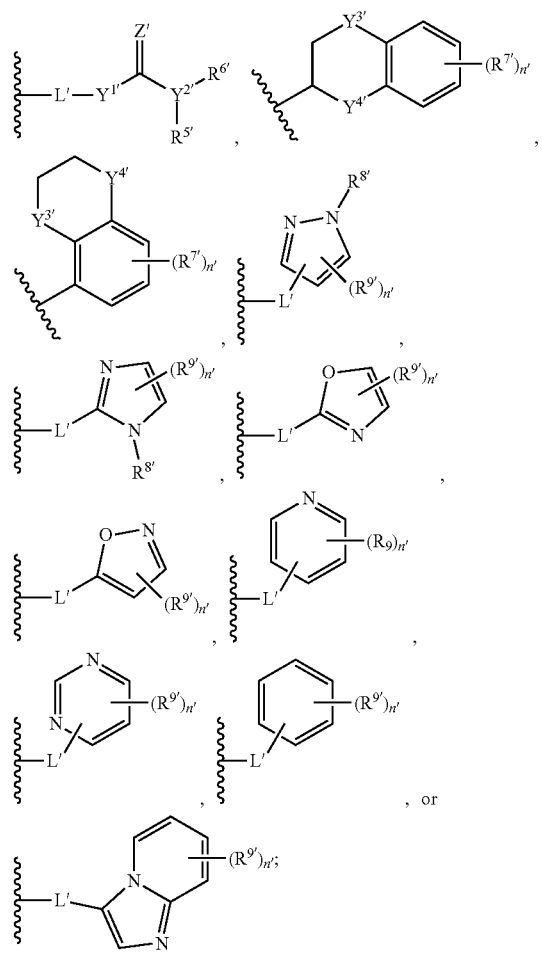

or
$R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;
L' is optionally substituted $C_{1-5}$ alkylene;
$Y^{1'}$, $Y^{2'}$, $Y^{3'}$, and $Y^{4'}$ are each independently a covalent bond, a carbon, an oxygen, or a nitrogen, optionally substituted with hydrogen, an optionally substituted $C_{1-6}$ alkyl, or an optionally substituted 3-7 membered saturated carbocyclic ring;

Z' is O or S;

R$^{5'}$ and R$^{6'}$ are each independently hydrogen or optionally substituted alkyl, or R$^{5'}$ and R$^{6'}$ are cyclically linked and, together with Y$^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each R$^{7'}$ is independently —R', halogen, —CN, —NO$_2$, —NR'$_2$, or —OR';

n' is an integer selected from 0 to 4;

R$^{8'}$ is hydrogen, —CN, optionally substituted alkyl, or an optionally substituted aryl ring;

each R$^{9'}$ is independently hydrogen, halogen, —CN, —NR'$_2$, or optionally substituted alkyl; and R$^{10'}$ and R$^{11'}$ are each independently hydrogen or optionally substituted C$_{1-2}$ aliphatic.

Further disclosed herein is a compound according to Formula (I"):

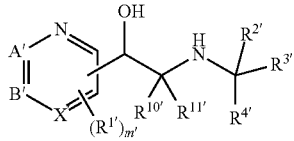

Formula (I")

or a pharmaceutically acceptable salt thereof, wherein:

A', B', and X' are each independently nitrogen or carbon;

each R$^{1'}$ is independently halogen, —R', —CN, —NO$_2$, —SF$_5$, —NR$^x$$_2$, —NHR$^x$, —SO$_2$R', —C(O)R', —C(O)NR'$_2$, —NR'C(O)R', —NR'CO$_2$R', or —CO$_2$R';

each R' is independently hydrogen or an optionally substituted group selected from: C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

each R$^x$ is independently an optionally substituted group selected from: C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur;

m' is an integer selected from 0 to 4;

R$^{2'}$, R$^{3'}$, and R$^{4'}$ are each independently halogen, —R', —CN, —NO$_2$, —OR', —NR'$_2$,

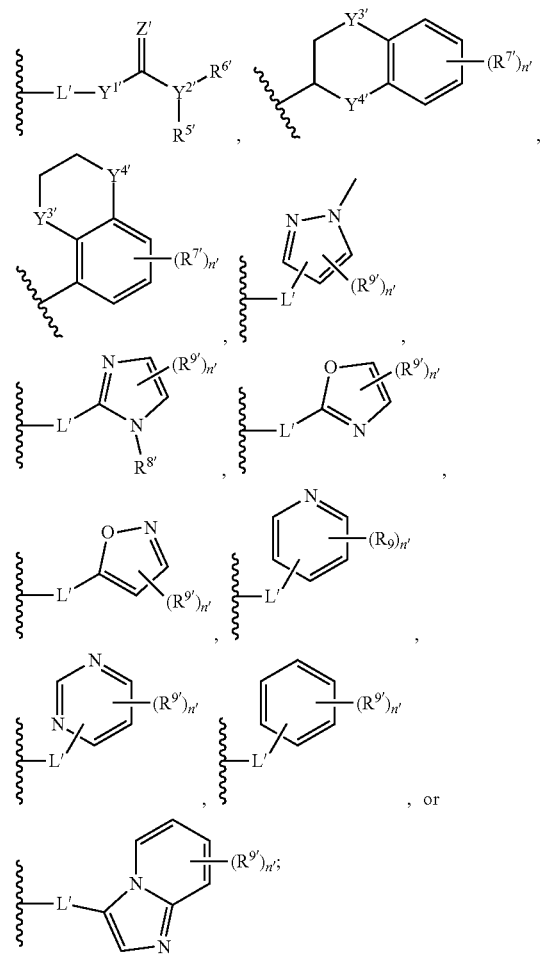

or

R$^{2'}$ and R$^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

L' is optionally substituted C$_{1-5}$ alkylene;

Y'', Y$^{2'}$, Y$^{3'}$, and Y$^{4'}$ are each independently a covalent bond, a carbon, an oxygen, or a nitrogen, optionally substituted with hydrogen, an optionally substituted C$_{1-6}$ alkyl, or an optionally substituted 3-7 membered saturated carbocyclic ring;

Z' is O or S;

R$^{5'}$ and R$^{6'}$ are each independently hydrogen or optionally substituted alkyl, or R$^{5'}$ and R$^{6'}$ are cyclically linked and, together with Y$^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur;

each $R^{7'}$ is independently —R', halogen, —CN, —NO$_2$, —NR'$_2$, or —OR';

n' is an integer selected from 0 to 4;

$R^{8'}$ is hydrogen, —CN, optionally substituted alkyl, or an optionally substituted aryl ring;

each $R^{9'}$ is independently hydrogen, halogen, —CN, —NR'$_2$, or optionally substituted alkyl; and $R^{10'}$ and $R^{11'}$ are each independently hydrogen or optionally substituted $C_{1-2}$ aliphatic.

As defined above and described herein, A' is nitrogen or carbon. In some embodiments A' is nitrogen. In some embodiments A' is carbon.

In some embodiments A' is selected from those depicted in Table 1, below.

As defined above and described herein, B' is nitrogen or carbon. In some embodiments B' is nitrogen. In some embodiments B' is carbon.

In some embodiments B' is selected from those depicted in Table 1, below.

As defined above and described herein, X' is nitrogen or carbon. In some embodiments X' is nitrogen. In some embodiments X' is carbon.

In some embodiments X' is selected from those depicted in Table 1, below.

As defined above, each $R^{1'}$ is independently halogen, —R', —CN, —NO$_2$, —SF$_5$, —OR$^x$, —NR$^x_2$, —NHR$^x$, —SO$_2$R', —C(O)R', —C(O)NR'$_2$, —NR'C(O)R', —NR'CO$_2$R', or —CO$_2$R'.

In some embodiments, $R^{1'}$ is hydrogen. In some embodiments, $R^{1'}$ is halogen. In some embodiments, $R^{1'}$ is —R'. In some embodiments, $R^{1'}$ is cyano. In some embodiments, $R^{1'}$ is —NO$_2$. In some embodiments, $R^{1'}$ is —SF$_5$. In some embodiments, $R^{1'}$ is —OR X. In some embodiments, $R^{1'}$ is —NR$^x_2$. In some embodiments, $R^{1'}$ is —NHR$^x$. In some embodiments, $R^{1'}$ is —SO$_2$R'. In some embodiments, $R^{1'}$ is —C(O)R'. In some embodiments, $R^{1'}$ is —C(O)NR'$_2$. In some embodiments, $R^{1'}$ is —NR'C(O)R'. In some embodiments, $R^{1'}$ is —NR'CO$_2$R'. In some embodiments, $R^{1'}$ is —CO$_2$R'.

In some embodiments, $R^{1'}$ is —Br. In some embodiments, $R^{1'}$ is —Cl. In some embodiments, $R^{1'}$ is —F.

In some embodiments, $R^{1'}$ is —CH$_3$. In some embodiments, $R^{1'}$ is —CH$_2$CH$_3$. In some embodiments, $R^{1'}$ is —CH(CH$_3$)$_2$.

In some embodiments, $R^{1'}$ is —CF$_3$. In some embodiments, $R^{1'}$ is —CF$_2$H. In some embodiments, $R^{1'}$ is —CFH$_2$. In some embodiments, $R^{1'}$ is —CF$_2$CH$_3$. In some embodiments, $R^{1'}$ is —CH$_2$CF$_3$. In some embodiments, $R^{1'}$ is —C≡CH. In some embodiments, $R^{1'}$ is vinyl. In some embodiments, $R^{1'}$ is —C≡CF$_3$. In some embodiments, $R^{1'}$ is —CO$_2$H.

In some embodiments, $R^{1'}$ is —CN.

In some embodiments, $R^{1'}$ is —OCH$_3$. In some embodiments, $R^{1'}$ is —OCH$_2$CH$_3$. In some embodiments, $R^{1'}$ is —OCH(CH$_3$)$_2$. In some embodiments, $R^{1'}$ is —OCF$_3$. In some embodiments, $R^{1'}$ is —NHCH$_3$. In some embodiments, $R^{1'}$ is —NHCD$_3$. In some embodiments, $R^{1'}$ is —N(CD$_3$)CO$_2$tBu. In some embodiments, $R^{1'}$ is —NHCH$_2$CH$_3$. In some embodiments, $R^{1'}$ is —NHCH(CH$_3$)$_2$. In some embodiments, $R^{1'}$ is —NHCH$_2$CF$_3$. In some embodiments, $R^{1'}$ is —NHPh. In some embodiments, $R^{1'}$ is —NHAc. In some embodiments, $R^{1'}$ is —N(CH$_3$)$_2$. In some embodiments, $R^{1'}$ is

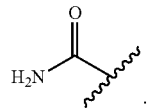

In some embodiments, $R^{1'}$ is

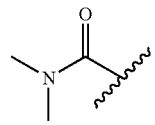

In some embodiments, $R^{1'}$ is

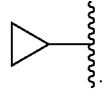

In some embodiments, $R^{1'}$ is

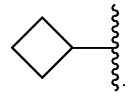

In some embodiments, $R^{1'}$ is

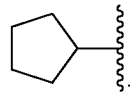

In some embodiments, $R^{1'}$ is

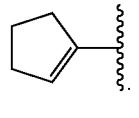

In some embodiments, $R^{1'}$ is

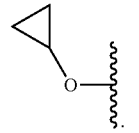

In some embodiments, R¹' is

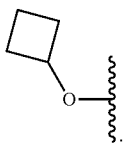 [SMILES: *OC1CCC1]

In some embodiments, R¹' is

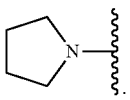

In some embodiments, R¹' is

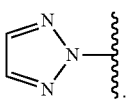

In some embodiments, R¹' is

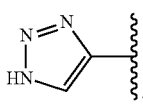

In some embodiments, R¹' is

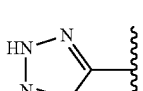

In some embodiments, R¹' is

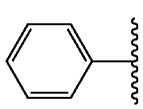

In some embodiments, R¹' is

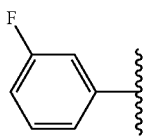

In some embodiments, R¹' is

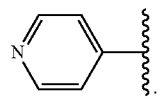

In some embodiments, R¹' is

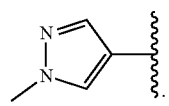

In some embodiments, R¹' is

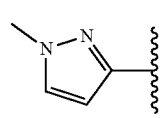

In some embodiments, R¹' is

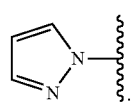

In some embodiments, R¹' is

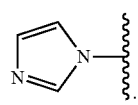

In some embodiments, R¹' is

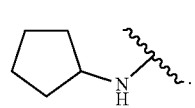 [SMILES: *NC1CCCC1]

In some embodiments, R¹' is

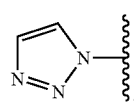

In some embodiments, R¹' is

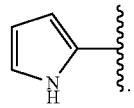

In some embodiments, R$^{1'}$ is

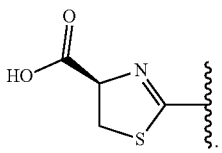

In some embodiments, R$^{1'}$ is

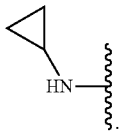

In some embodiments, R$^{1'}$ is

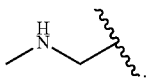

In some embodiments, R$^{1'}$ is

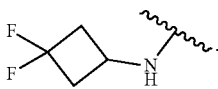

In some embodiments, R$^{1'}$ is

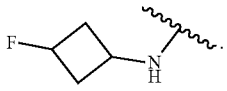

In some embodiments, R$^{1'}$ is

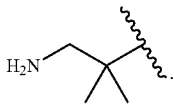

In some embodiments, R$^{1'}$ is selected from those depicted in Table 1, below.

As defined above, each R' is independently hydrogen or an optionally substituted group selected from C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur.

In some embodiments, R' is hydrogen.

In some embodiments, R' is an optionally substituted C$_{1-6}$ aliphatic. For instance, in some embodiments, R' is —CF$_3$, —CF$_2$H, or —CFH$_2$.

In some embodiments, R' is an optionally substituted 3-8 membered saturated monocyclic carbocyclic ring.

In some embodiments, R' is an optionally substituted 3-8 membered partially unsaturated monocyclic carbocyclic ring.

In some embodiments, R' is an optionally substituted phenyl.

In some embodiments, R' is an optionally substituted 8-10 membered bicyclic partially unsaturated carbocyclic ring.

In some embodiments, R' is an optionally substituted 8-10 membered bicyclic aromatic carbocyclic ring.

In some embodiments, R' is an optionally substituted 4-8 membered saturated monocyclic heterocyclic ring having 1-2 heteroatoms independently selected from nitrogen, oxygen, or sulfur.

In some embodiments, R' is an optionally substituted 4-8 membered partially unsaturated monocyclic heterocyclic ring having 1-2 heteroatoms independently selected from nitrogen, oxygen, or sulfur.

In some embodiments, R' is an optionally substituted 5-6 membered monocyclic heteroaromatic ring having 1-4 heteroatoms independently selected from nitrogen, oxygen, or sulfur.

In some embodiments, R' is an optionally substituted 8-10 membered bicyclic partially unsaturated ring having 1-5 heteroatoms independently selected from nitrogen, oxygen, or sulfur.

In some embodiments, R' is an optionally substituted 8-10 membered bicyclic heteroaromatic ring having 1-5 heteroatoms independently selected from nitrogen, oxygen, or sulfur.

In some embodiments, R' is selected from those depicted in Table 1, below.

As defined above, each R$^x$ is independently an optionally substituted group selected from C$_{1-6}$ aliphatic, a 3-8 membered saturated or partially unsaturated monocyclic carbocyclic ring, phenyl, an 8-10 membered bicyclic partially unsaturated or aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic partially unsaturated or heteroaromatic ring having 1-5 heteroatoms independently selected from nitrogen, oxygen, or sulfur.

In some embodiments, R$^x$ is an optionally substituted C$_{1-6}$ aliphatic. For instance, in some embodiments, R$^x$ is —CF$_3$, —CF$_2$H, or —CFH$_2$. In some embodiments, R$^x$ is C$_{1-6}$ alkyl.

As defined above, m' is an integer selected from 0 to 4.

In some embodiments, m' is 0. In some embodiments, m' is 1. In some embodiments, m' is 2. In some embodiments, m' is 3. In some embodiments, m' is 4.

As defined above, R$^{2'}$, R$^{3'}$, and R$^{4'}$ are each independently halogen, —R', —CN, —OH, —OR', —NR'$_2$, —NHR', —NH$_2$,

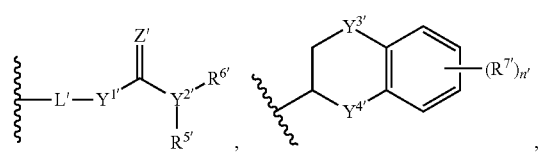

-continued

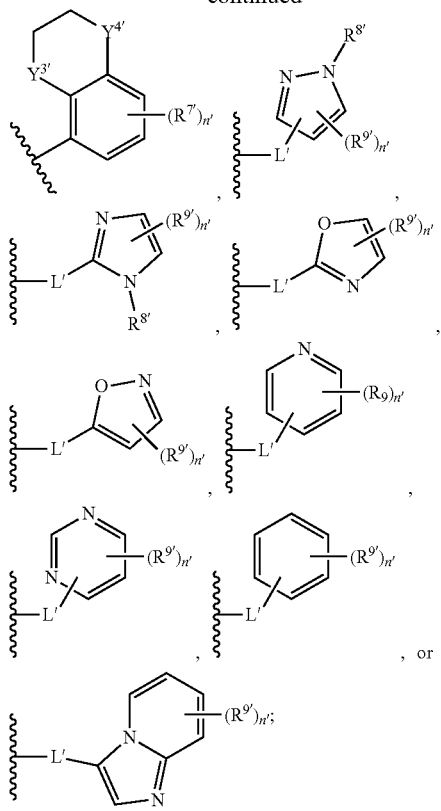

or R[2'] and R[3'] together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur;

In some embodiments, R[2'] is hydrogen. In some embodiments, R[2'] is halogen. In some embodiments, R[2'] is —R'. In some embodiments, R[2'] is —CN. In some embodiments, R[2'] is —NO$_2$. In some embodiments, R[2'] is —OH. In some embodiments, R[2'] is —OR'. In some embodiments, R[2'] is —NR'$_2$. In some embodiments, R[2'] is —NHR'. In some embodiments, R[2'] is —NH$_2$.

In some embodiments, R[2'] is

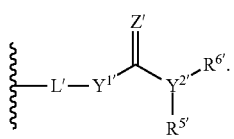

In some embodiments, R[2'] is

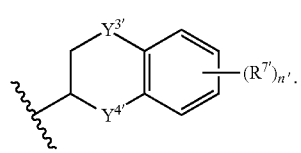

In some embodiments, R[2'] is

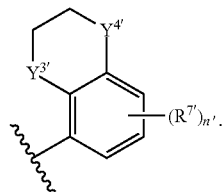

In some embodiments, R[2'] is

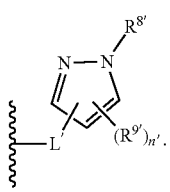

In some embodiments, R[2'] is

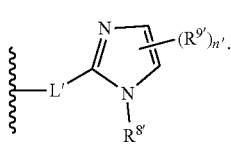

In some embodiments, R[2'] is

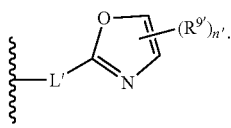

In some embodiments, R[2'] is

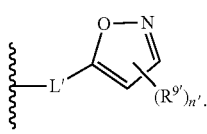

In some embodiments, R[2'] is

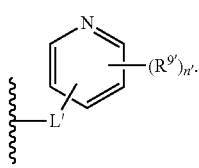

In some embodiments, R²' is

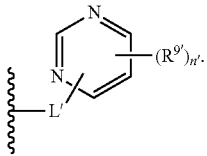

In some embodiments, R²' is

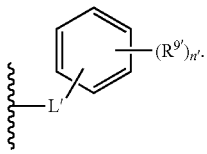

In some embodiments, R²' is

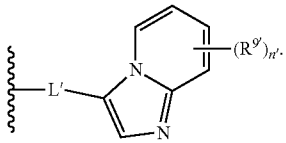

In some embodiments, R²' is hydrogen. In some embodiments, R²' is deuterium. In some embodiments, R²' is —CH₃. In some embodiments, R²' is —CD₃. In some embodiments, R²' is

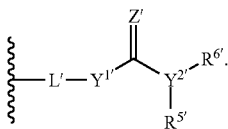

In some embodiments, R³' is hydrogen. In some embodiments, R³' is halogen. In some embodiments, R³' is —R'. In some embodiments, R³' is —CN. In some embodiments, R³' is —NO₂. In some embodiments, R³' is —OH. In some embodiments, R³' is —OR'. In some embodiments, R³' is —NR'₂. In some embodiments, R³' is —NHR'. In some embodiments, R³' is —NH₂.

In some embodiments, R³' is

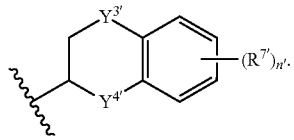

In some embodiments, R³' is

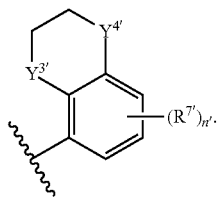

In some embodiments, R³' is

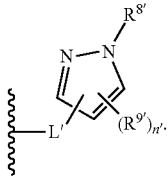

In some embodiments, R³' is

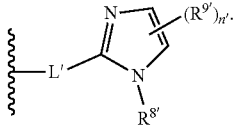

In some embodiments, R³' is

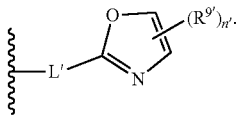

In some embodiments, R³' is

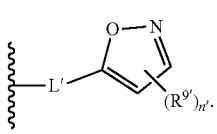

In some embodiments, $R^{3'}$ is

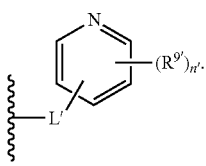

In some embodiments, $R^{3'}$ is

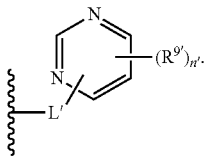

In some embodiments, $R^{3'}$ is

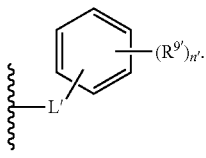

In some embodiments, $R^{3'}$ is

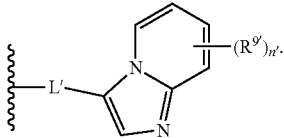

In some embodiments, $R^{3'}$ is hydrogen. In some embodiments, $R^{3'}$ is deuterium. In some embodiments, $R^{3'}$ is —CH$_3$. In some embodiments, $R^{3'}$ is —CD$_3$. In some embodiments, $R^{3'}$ is

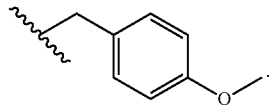

In some embodiments, $R^{2'}$ and $R^{3'}$ together with the carbon form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or a partially unsaturated monocyclic heterocyclic ring having 1-2 heteroatoms independently selected from nitrogen, oxygen, and sulfur.

In some embodiments, $R^{2'}$ and $R^{3'}$ together with the carbon form an optionally substituted 3-7 membered saturated carbocyclic ring.

In some embodiments, $R^{2'}$ and $R^{3'}$ together with the carbon form an optionally substituted 5-6 membered monocyclic heteroaryl ring having 1-4 heteroatoms independently selected from nitrogen, oxygen, and sulfur.

In some embodiments, $R^{2'}$ and $R^{3'}$ together with the carbon form an optionally substituted 3-7 membered saturated or a partially unsaturated monocyclic heterocyclic ring having 1-2 heteroatoms independently selected from nitrogen, oxygen, and sulfur.

In some embodiments, $R^{2'}$ and $R^{3'}$ together with the carbon form

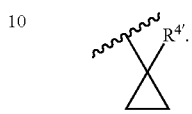

In some embodiments, $R^{2'}$ and $R^{3'}$ together with the carbon form

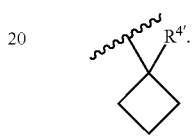

In some embodiments, $R^{2'}$ and $R^{3'}$ together with the carbon form

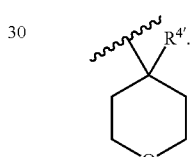

In some embodiments, $R^{2'}$ and $R^{3'}$ together with the carbon form

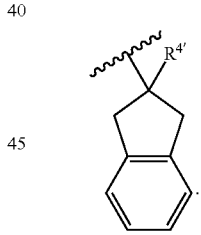

In some embodiments, $R^{4'}$ is hydrogen. In some embodiments, $R^{4'}$ is halogen. In some embodiments, $R^{4'}$ is —R'. In some embodiments, $R^{4'}$ is —CN. In some embodiments, $R^{4'}$ is —NO$_2$. In some embodiments, $R^{4'}$ is —OH. In some embodiments, $R^{4'}$ is —OR'. In some embodiments, $R^{4'}$ is —NR'$_2$. In some embodiments, $R^{4'}$ is —NHR'. In some embodiments, $R^{4'}$ is —NH$_2$. In some embodiments, $R^{4'}$ is —CF$_3$.

In some embodiments, $R^{4'}$ is

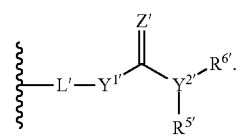

In some embodiments, R⁴' is

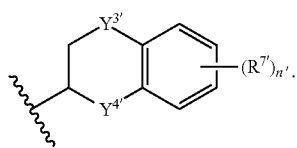

In some embodiments, R⁴' is

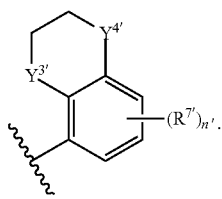

In some embodiments, R⁴' is

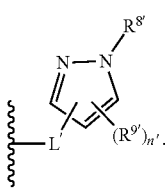

In some embodiments, R⁴' is

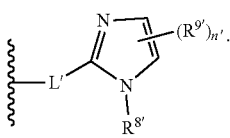

In some embodiments, R⁴' is

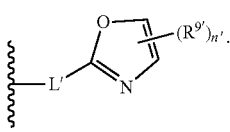

In some embodiments, R⁴' is

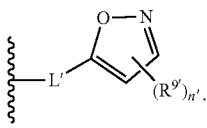

In some embodiments, R⁴' is

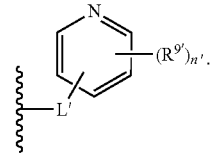

In some embodiments, R⁴' is

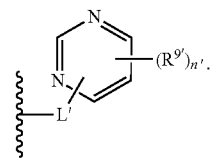

In some embodiments, R⁴' is

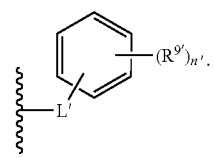

In some embodiments, R⁴' is

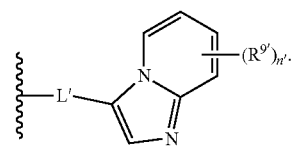

In some embodiments, R⁴' is hydrogen. In some embodiments, R⁴' is deuterium. In some embodiments, R⁴' is —CH₃. In some embodiments, R⁴' is —CD₃. some embodiments, R⁴' is

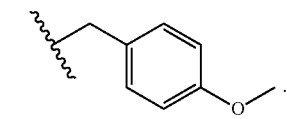 [SMILES: *Cc1ccc(OC)cc1]

In some embodiments, R²', R³', and R⁴', are each selected from those depicted in Table 1, below.

As defined above, L' is optionally substituted $C_{1-5}$ alkylene.

In some embodiments, L' is —CH₂—.

In some embodiments, L' is selected from those depicted in Table 1, below.

As defined above, Y¹', Y²', Y³', and Y⁴' are each independently a covalent bond, a carbon, an oxygen; or a nitrogen, optionally substituted with hydrogen, an optionally substituted $C_{1-6}$ alkyl, or an optionally substituted 3-7 membered saturated carbocyclic ring.

In some embodiments, Y¹' is a covalent bond. In some embodiments, Y¹' is a carbon. In some embodiments, Y¹' is an oxygen. In some embodiments, Y¹' is a nitrogen, optionally substituted with hydrogen, an optionally substituted $C_{1-6}$ alkyl, or an optionally substituted 3-7 membered saturated carbocyclic ring.

In some embodiments, $Y^{2'}$ is a covalent bond. In some embodiments, $Y^{2'}$ is a carbon. In some embodiments, $Y^{2'}$ is an oxygen. In some embodiments, $Y^{2'}$ is a nitrogen, optionally substituted with hydrogen, an optionally substituted $C_{1-6}$ alkyl, or an optionally substituted 3-7 membered saturated carbocyclic ring.

In some embodiments, $Y^{3'}$ is a covalent bond. In some embodiments, $Y^{3'}$ is a carbon. In some embodiments, $Y^{3'}$ is an oxygen. In some embodiments, $Y^{3'}$ is a nitrogen, optionally substituted with hydrogen, an optionally substituted $C_{1-6}$ alkyl, or an optionally substituted 3-7 membered saturated carbocyclic ring.

In some embodiments, $Y^{3'}$ is a covalent bond. In some embodiments, $Y^{3'}$ is a carbon.

In some embodiments, $Y^{4'}$ is a covalent bond. In some embodiments, $Y^{4'}$ is a carbon. In some embodiments, $Y^{4'}$ is an oxygen. In some embodiments, $Y^{4'}$ is a nitrogen, optionally substituted with hydrogen, an optionally substituted $C_{1-6}$ alkyl, or an optionally substituted 3-7 membered saturated carbocyclic ring.

In some embodiments, $Y^{4'}$ is a covalent bond. In some embodiments, $Y^{4'}$ is a carbon.

In some embodiments, $Y^{1'}$, $Y^{2'}$, $Y^{3'}$, and $Y^{4'}$ are each selected from those depicted in Table 1, below.

As defined above, $Z'$ is O or S.

In some embodiments, $Z'$ is O. In some embodiments, $Z'$ is S.

In some embodiments, $Z'$ is selected from those depicted in Table 1, below.

As defined above, $R^{5'}$ and $R^{6'}$ are each independently hydrogen or optionally substituted alkyl, or $R^{5'}$ and $R^{6'}$ are cyclically linked and, together with $Y^{2'}$, to form an optionally substituted 3-7 membered saturated carbocyclic ring; an optionally substituted 5-6 membered monocyclic heteroaryl ring having 1-4 heteroatoms independently selected from nitrogen, oxygen, and sulfur; an optionally substituted 3-7 membered saturated or partially unsaturated monocyclic heterocyclic ring having 1-2 heteroatoms independently selected from nitrogen, oxygen, and sulfur; or an optionally substituted 7-12 membered saturated or partially unsaturated bicyclic heterocyclic ring having 1-4 heteroatoms independently selected from nitrogen, oxygen, and sulfur.

In some embodiments, $R^{5'}$ is hydrogen. In some embodiments, $R^{5'}$ is an optionally substituted $C_{1-6}$ alkyl.

In some embodiments, $R^{6'}$ is hydrogen. In some embodiments, $R^{6'}$ is an optionally substituted $C_{1-6}$ alkyl.

In some embodiments, $R^{5'}$ and $R^{6'}$ are cyclically linked and together with $Y^{2'}$ form an optionally substituted 3-7 membered saturated carbocyclic ring.

In some embodiments, $R^{5'}$ and $R^{6'}$ are cyclically linked and together with $Y^{2'}$ form an optionally substituted 5-6 membered monocyclic heteroaryl ring having 1-4 heteroatoms independently selected from nitrogen, oxygen, and sulfur.

In some embodiments, $R^{5'}$ and $R^{6'}$ are cyclically linked and together with $Y^{2'}$ form an optionally substituted 3-7 membered saturated or partially unsaturated monocyclic heterocyclic ring having 1-2 heteroatoms independently selected from nitrogen, oxygen, and sulfur.

In some embodiments, $R^{5'}$ and $R^{6'}$ are cyclically linked and together with $Y^{2'}$ form an optionally substituted 7-12 membered saturated or partially unsaturated bicyclic heterocyclic ring having 1-4 heteroatoms independently selected from nitrogen, oxygen, and sulfur.

In some embodiments, $R^{5'}$ and $R^{6'}$ are each selected from those depicted in Table 1, below.

As defined above, each $R^{7'}$ is independently —R', halogen, —CN, —NO$_2$, —OH, —NR'$_2$, —NHR', —NH$_2$, or —OR'.

In some embodiments, $R^{7'}$ is hydrogen. In some embodiments, $R^{7'}$ is halogen. In some embodiments, $R^{7'}$ is —CN. In some embodiments, $R^{7'}$ is —NO$_2$. In some embodiments, $R^{7'}$ is —OH. In some embodiments, $R^{7'}$ is —NR'$_2$. In some embodiments, $R^{7'}$ is —NHR'. In some embodiments, $R^{7'}$ is —NH$_2$. In some embodiments, $R^{7'}$ is —OR'.

In some embodiments, each $R^T$ is independently selected from those depicted in Table 1, below.

As defined above, n' is an integer selected from 0 to 4.

In some embodiments, n' is 0. In some embodiments, n' is 1. In some embodiments, n' is 2. In some embodiments, n' is 3. In some embodiments, n' is 4.

As defined above, $R^{8'}$ is hydrogen, —CN, optionally substituted alkyl, or an optionally substituted aryl ring.

In some embodiments, $R^{8'}$ is hydrogen. In some embodiments, $R^{8'}$ is —CN. In some embodiments, $R^{8'}$ is an optionally substituted $C_{1-6}$ alkyl. In some embodiments, $R^{8'}$ is an optionally substituted aryl ring.

In some embodiments, $R^{8'}$ is selected from those depicted in Table 1, below.

As defined above, each $R^{9'}$ is independently hydrogen, halogen, —CN, —OR', —NR'$_2$, or optionally substituted alkyl.

In some embodiments, $R^{9'}$ is hydrogen. In some embodiments, $R^{9'}$ is halogen. In some embodiments, $R^{9'}$ is —CN. In some embodiments, $R^{9'}$ is —OR$^x$. In some embodiments, $R^{9'}$ is —NR'$_2$. In some embodiments, $R^{9'}$ is —NHR'. In some embodiments, $R^{9'}$ is —NH$_2$. In some embodiments, $R^{9'}$ is an optionally substituted $C_{1-6}$ alkyl.

In some embodiments, $R^{9'}$ is selected from those depicted in Table 1, below.

As defined above, $R^{10'}$ and $R^{11'}$ are each independently hydrogen or optionally substituted $C_{1-2}$ aliphatic. In some embodiments, $R^{10'}$ and $R^{11'}$ are each independently hydrogen, methyl, or ethyl.

In some embodiments, $R^{10'}$ is hydrogen. In some embodiment, $R^{10'}$ is an optionally substituted $C_1$ aliphatic. In some embodiment, $R^{10'}$ is methyl. In some embodiment, $R^{10'}$ is an optionally substituted $C_2$ aliphatic. In some embodiment, $R^{10'}$ is ethyl.

In some embodiments, $R^{10'}$ is selected from those depicted in Table 1, below.

In some embodiments, $R^{11'}$ is hydrogen. In some embodiment, $R^{11'}$ is an optionally substituted $C_1$ aliphatic. In some embodiment, $R^{11'}$ is methyl. In some embodiment, $R^{11'}$ is an optionally substituted $C_2$ aliphatic. In some embodiment, $R^{11'}$ is ethyl.

In some embodiments, $R^{11'}$ is selected from those depicted in Table 1, below.

Further disclosed herein is a compound according to Formula (II'):

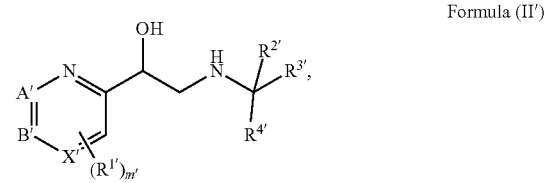

Formula (II')

or a pharmaceutically acceptable salt thereof, wherein each of A', B', X', $R^{1'}$, $R^{2'}$, $R^{3'}$, $R^{4'}$, and m' is as defined above and as described in embodiments provided herein, both singly and in combination.

Further disclosed herein is a compound according to Formula (III'):

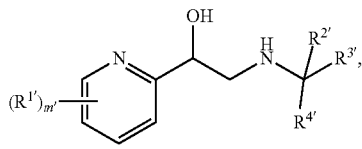

Formula (III')

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a compound according to Formula (IV'):

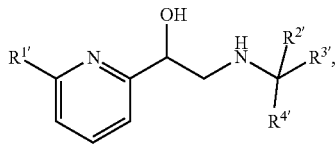

Formula (IV')

or a pharmaceutically acceptable salt thereof, wherein each of $R^{1'}$, $R^{2'}$, $R^{3'}$, and $R^{4'}$ is as defined above and as described in embodiments provided herein, both singly and in combination. In some such embodiments, $R^{1'}$ is —$CF_3$. In some such embodiments, $R^{1'}$ is —$CF_2H$. In some such embodiments, $R^{1'}$ is —$OCF_3$. In some such embodiments, $R^{1'}$ is —CN. In some such embodiments, $R^{1'}$ is —C(O)$NR'_2$. In some such embodiments, $R^{1'}$ is a cyclopropyl group. In some such embodiments, $R^{1'}$ is a tetrazole. In some such embodiments, $R^{1'}$ is phenyl. In some such embodiments, $R^{1'}$ is —Br. In some such embodiments, $R^{1'}$ is —$CH_3$.

Further disclosed herein is a compound according to Formula (V'):

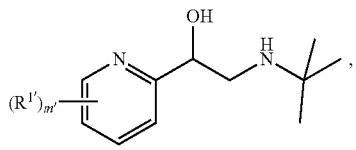

Formula (V')

or a pharmaceutically acceptable salt thereof, wherein each of $R^{1'}$ and m' is as defined above and as described in embodiments provided herein, both singly and in combination.

Further disclosed herein is a compound according to Formula (VI'):

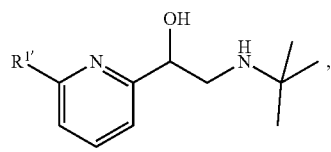

Formula (VI')

or a pharmaceutically acceptable salt thereof, wherein $R^{1'}$ is as defined above and as described in embodiments provided herein, both singly and in combination.

Further disclosed herein is a compound according to Formula (VII'):

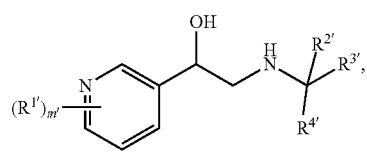

Formula (VII')

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a compound according to Formula (VIII'):

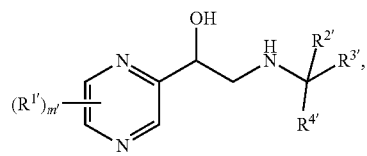

Formula (VIII')

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a compound according to Formula (IX'):

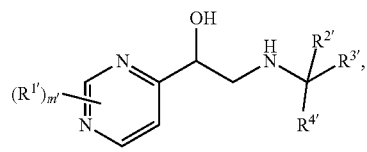

Formula (IX')

or a pharmaceutically acceptable salt thereof, wherein each of $R^{1'}$, $R^{2'}$, $R^{3'}$, $R^{4'}$, and m' is as defined above and as described in embodiments provided herein, both singly and in combination.

Further disclosed herein is a compound according to Formula (X'):

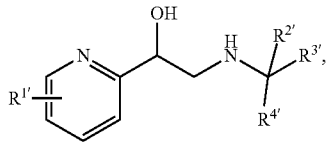

Formula (X')

or a pharmaceutically acceptable salt thereof,
wherein
R$^{1'}$ is halogen, —R$^x$, —CN, —NO$_2$, —SF$_5$, —OR', —SO$_2$R', or —C(O)R';
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring; and
R' and R$^x$ are as defined above and as described in embodiments provided herein, both singly and in combination. In some such embodiments, R$^{1'}$ is —CF$_3$. In some such embodiments, R$^{1'}$ is —CF$_2$H. In some such embodiments, R$^{1'}$ is —OCF$_3$. In some such embodiments, R$^{1'}$ is —CN. In some such embodiments, R$^{1'}$ is —C(O)NR'$_2$. In some such embodiments, R$^{1'}$ is a cyclopropyl group. In some such embodiments, R$^{1'}$ is a tetrazole. In some such embodiments, R$^{1'}$ is phenyl. In some such embodiments, R$^{1'}$ is —Br. In some such embodiments, R$^{1'}$ is —CH$_3$.

Further disclosed herein is a compound according to Formula (XI'):

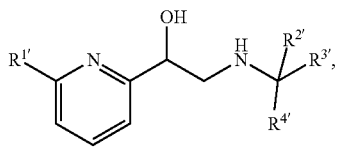

Formula (XI')

or a pharmaceutically acceptable salt thereof,
wherein:
R$^{1'}$ is halogen, —R', —CN, —NO$_2$, —SF$_5$, —OR', —SO$_2$R', or —C(O)R'; R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring; and
R' and R$^x$ are as defined above and as described in embodiments provided herein, both singly and in combination.

Further disclosed herein is a compound according to Formula (XII'):

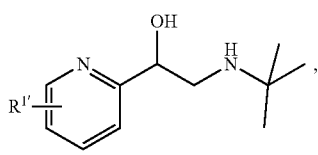

Formula (XII')

or a pharmaceutically acceptable salt thereof,
wherein:
R$^{1'}$ is halogen, —R', —CN, —NO$_2$, —SF$_5$, —SO$_2$R', or —C(O)R'; and
R' and R$^x$ are as defined above and as described in embodiments provided herein, both singly and in combination.

Further disclosed herein is a compound according to Formula (XIII'):

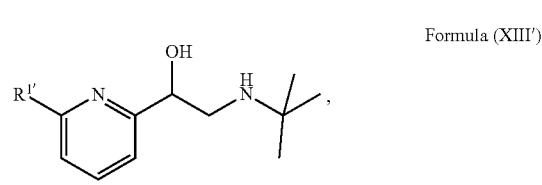

Formula (XIII')

or a pharmaceutically acceptable salt thereof,
wherein:
R$^{1'}$ is halogen, —R', —CN, —NO$_2$, —SF$_5$, —SO$_2$R', or —C(O)R'; and
R' and R$^x$ are as defined above and as described in embodiments provided herein, both singly and in combination.

Further disclosed herein is a compound according to Formula (XIV'):

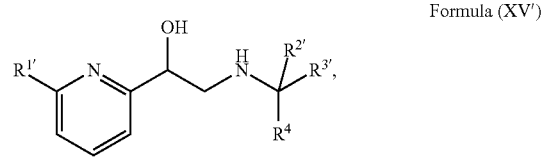

Formula (XIV')

or a pharmaceutically acceptable salt thereof,
wherein
R$^{1'}$ is halogen, —R', —CN, or —NO$_2$;
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring; and
R' is as defined above and as described in embodiments provided herein, both singly and in combination.

Further disclosed herein is a compound according to Formula (XV'):

Formula (XV')

or a pharmaceutically acceptable salt thereof,
wherein:
R$^{1'}$ is halogen, —R', —CN, or —NO$_2$;
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring; and
R' is as defined above and as described in embodiments provided herein, both singly and in combination.

Further disclosed herein is a compound according to Formula (XVI'):

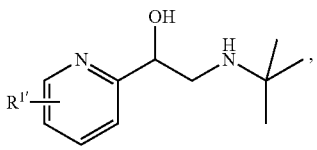

Formula (XVI')

or a pharmaceutically acceptable salt thereof,
wherein:
R$^{1'}$ is halogen, —R', —CN, or —NO$_2$; and
R' is as defined above and as described in embodiments provided herein, both singly and in combination.

Further disclosed herein is a compound according to Formula (XVII'):

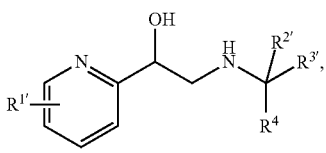

Formula (XVII')

or a pharmaceutically acceptable salt thereof,
wherein
R$^{1'}$ is halogen, —R', —CN, or —NO$_2$;
each R' is an optionally substituted C$_{1-6}$ aliphatic; and
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring.

Further disclosed herein is a compound according to Formula (XVIII'):

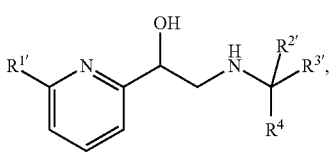

Formula (XVIII')

or a pharmaceutically acceptable salt thereof,
wherein:
R$^{1'}$ is halogen, —R', —CN, or —NO$_2$;
each R' is an optionally substituted C$_{1-6}$ aliphatic; and
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring.

Further disclosed herein is a compound according to Formula (XIX'):

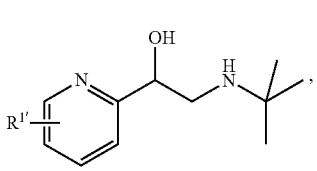

Formula (XIX')

or a pharmaceutically acceptable salt thereof,
wherein:
R$^{1'}$ is halogen, —R', —CN, or —NO$_2$; and
R' is optionally substituted C$_{1-6}$ aliphatic.

Further disclosed herein is a compound according to Formula (XX'):

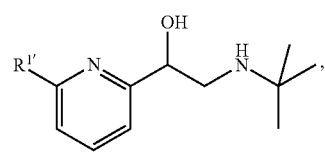

Formula (XX')

or a pharmaceutically acceptable salt thereof,
wherein:
R$^{1'}$ is halogen, —R', —CN, or —NO$_2$; and
R' is an optionally substituted C$_{1-6}$ aliphatic.

Further disclosed herein is a compound according to Formula (XXI'):

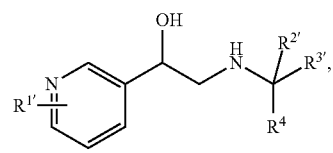

Formula (XXI')

or a pharmaceutically acceptable salt thereof,
wherein
R$^{1'}$ is halogen, —R', —CN, or —NO$_2$;
each R' is an optionally substituted C$_{1-6}$ aliphatic; and
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring.

Further disclosed herein is a compound according to Formula (XXII'):

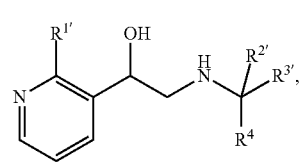

Formula (XXII')

or a pharmaceutically acceptable salt thereof,
wherein:
R$^{1'}$ is halogen, —R', —CN, or —NO$_2$;
each R' is an optionally substituted C$_{1-6}$ aliphatic; and
R$^{2'}$, R$^{3'}$, and R$^{4'}$ are each independently halogen, —R', —CN, —NO$_2$, —OR', or —NR'$_2$, or
R$^{2'}$ and R$^{3'}$ together with the carbon form an optionally substituted 3-7 membered cycloalkyl or heterocycle ring.

Further disclosed herein is a compound according to Formula (XXIII'):

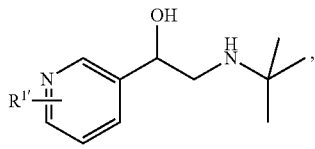

Formula (XXIII')

or a pharmaceutically acceptable salt thereof, wherein:
R$^{1'}$ is halogen, —R', —CN, or —NO$_2$; and
R' is optionally substituted C$_{1-6}$ aliphatic.

Further disclosed herein is a compound according to Formula (XXIV'):

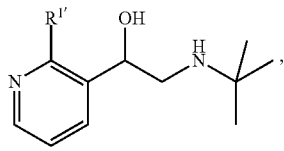

Formula (XXIV')

or a pharmaceutically acceptable salt thereof, wherein:
R$^{1'}$ is halogen, —R', —CN, or —NO$_2$; and
R' is an optionally substituted C$_{1-6}$ aliphatic.

Further disclosed herein is a compound according to Formula (XXV'):

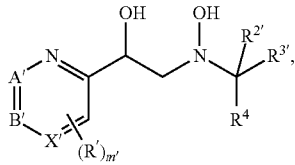

Formula (XXV')

or a pharmaceutically acceptable salt thereof,
wherein each of A', B', X', R$^{1'}$, R$^{2'}$, R$^{3'}$, R$^{4'}$, and m' is as defined above and as described in embodiments provided herein, both singly and in combination.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those at risk or needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. In some embodiments, such amount should be sufficient to modulate an adrenergic receptor.

In some embodiments, an effective amount of an adrenergic receptor modulating compound is an amount that ranges from about 50 ng/ml to 50 pg/ml (e.g., from about 50 ng/ml to 40 pg/ml, from about 30 ng/ml to 20 pg/ml, from about 50 ng/ml to 10 µg/ml, from about 50 ng/ml to 1 µg/ml, from about 50 ng/ml to 800 ng/ml, from about 50 ng/ml to 700 ng/ml, from about 50 ng/ml to 600 ng/ml, from about 50 ng/ml to 500 ng/ml, from about 50 ng/ml to 400 ng/ml, from about 60 ng/ml to 400 ng/ml, from about 70 ng/ml to 300 ng/ml, from about 60 ng/ml to 100 ng/ml, from about 65 ng/ml to 85 ng/ml, from about 70 ng/ml to 90 ng/ml, from about 200 ng/ml to 900 ng/ml, from about 200 ng/ml to 800 ng/ml, from about 200 ng/ml to 700 ng/ml, from about 200 ng/ml to 600 ng/ml, from about 200 ng/ml to 500 ng/ml, from about 200 ng/ml to 400 ng/ml, or from about 200 ng/ml to about ng/ml).

In some embodiments, an effective amount of an adrenergic receptor modulating compound is an amount that ranges from about 10 pg to 100 mg, e.g., from about 10 pg to 50 pg, from about 50 pg to 150 pg, from about 150 pg to 250 pg, from about 250 pg to 500 pg, from about 500 pg to 750 pg, from about 750 pg to 1 ng, from about 1 ng to 10 ng, from about 10 ng to 50 ng, from about 50 ng to 150 ng, from about 150 ng to 250 ng, from about 250 ng to 500 ng, from about 500 ng to 750 ng, from about 750 ng to 1 mg, from about 1 pg to 10 pg, from about 10 pg to 50 pg, from about 50 pg to 150 pg, from about 150 pg to 250 pg, from about 250 pg to 500 pg, from about 500 pg to 750 pg, from about 750 pg to 1 mg, from about 1 mg to 50 mg, from about 1 mg to 100 mg, or from about 50 mg to 100 mg. The amount can be a single dose amount or can be a total daily amount. The total daily amount can range from about 10 pg to 100 mg, or can range from about 100 mg to 500 mg, or can range from about 500 mg to 1000 mg.

Also disclosed herein are pharmaceutical compositions including compounds as disclosed herein e.g., with the structures of Formula (I), Formula (II), Formula (III), Formula (I'), Formula (I''), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), and Formula (XXV'). The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

In some embodiments, a compound as disclosed herein may be an adrenergic receptor modulating compound (e.g., an agonist, partial agonist or antagonist of an adrenergic receptor). The adrenergic receptor modulating compounds of the present disclosure can in some embodiments find use in modulating the activity of a target adrenergic receptor in vitro or in vivo. Aspects of the subject methods include contacting a sample with an effective amount of an adrenergic receptor modulating compound (e.g., as described herein) to determine whether the activity desired exists.

Adrenergic receptors (ADRs) are G-protein coupled receptors (GPCR) that are widely expressed throughout the body and play an important role in regulating multiple physiological processes including cognition, stress-related behavior, inflammation, and smooth muscle contraction/dilation, cardiac muscle contraction, airway reactivity and cognition. Adrenergic receptors mediate the central and peripheral effects of noradrenaline (NA) and adrenaline. Multiple subtypes of ADRs exist, including α-adrenergic receptors and β-adrenergic receptors. Each subtype is expressed in distinct patterns and involved in different physiological processes. Therefore, ligands that selectively target one subtype are valuable both as research tools to identify the roles of different ADR subtypes and as therapeutic agents for multiple diseases related to dysfunction of the NA and adrenaline systems.

β-adrenergic receptors further include three sub-types: β1-adrenergic receptor (β1-ADR), β2-adrenergic receptor (β2-ADR), and β3-adrenergic receptor (β3-ADR). Because these subtypes are expressed in distinct patterns and involved in different physiological processes, ligands that can selectively target one subtype have therapeutic potential for multiple diseases. However, discovery of subtype-selective ligands has been challenging due to a high level of sequence homology shared by these subtypes. A lot of existing agonists for β-adrenergic receptors also exhibit inferior blood-brain-barrier (BBB) penetration, which is required in an effort for drug discovery for central nervous system (CNS) indications.

As a class of G-protein coupled receptor, adrenergic receptors signal via G protein- and β-arrestin-dependent pathways. G protein- or β-arrestin signaling can mediate different physiological responses. Recently, it has become clear that agonists can show biased activation of signaling pathways. The ability of ligands to activate the receptor and produce responses in a pathway-dependent manner has been termed "signaling bias" or "functional selectivity". As G proteins and β-arrestins mediate distinct physiological processes, biased agonists can provide improved therapeutic selectivity with reduced adverse effects. Thus, the present disclosure is directed to β-adrenergic receptor subtype-selective agonists with improved blood-brain-barrier (BBB) penetration.

An adrenergic receptor modulating compound can be an agonist of the target adrenergic receptor. In some cases, an effective amount of an adrenergic receptor modulating compound is an amount sufficient to activate an activity related to the adrenergic receptor in a cell by 10% or more, such as 20% or more, 30% or more, 40% or more, 50% or more, 60% or more, 70% or more, 80% or more, 90% or more, 100% or more, 200% or even more relative to a control, e.g., a control cell exhibiting a known activity level of the receptor.

The adrenergic receptor modulating compound can be a partial agonist of the target adrenergic receptor. In some cases, an effective amount of an adrenergic receptor modulating compound is an amount sufficient to achieve partially agonism of the adrenergic receptor in a cell, e.g., where the subject compound achieves 10% activation or more of the receptor, such as 20% or more, 30% or more, 40% or more, 50% or more, 60% or more, 70% or more, 80% or more, or 90% or more, relative to a control, e.g., a receptor that is fully activated. Partial agonism may be assessed using any convenient methods, such as a cell based assay using a known full agonist as a 100% activation control, where the relative maximum activation of the receptor can be measured relative to the full agonist.

The adrenergic receptor modulating compound can be an antagonist of the target adrenergic receptor. In some cases, an effective amount of an adrenergic receptor modulating compound is an amount sufficient to inhibit or decrease the activity of the target adrenergic receptor in a sample by 10% or more, such as 20% or more, 30% or more, 40% or more, 50% or more, 60% or more, 70% or more, 80% or more, 90% or more, or even more relative to a control, e.g., a sample not contacted with the compound of interest.

In some embodiments, a compound of the present disclosure acts as a low nM partial agonist of the β2 adrenergic receptor. For instance, in some embodiments, a compound of the present disclosure has an $EC_{50}$ of less than about 1 nM, less than about 5 nM, less than about 10 nM, less than about 15 nM, less than about 20 nM, less than 25 nM, less than 30 nM, less than 35 nM, less than 40 nM, less than 45 nM, less than 50 nM, less than 55 nM, less than 60 nM, less than 65 nM, less than 70 nM, less than 75 nM, less than 80 nM, less than 85 nM, less than 90 nM, less than 95 nM, or less than 100 nM. In some embodiments, a compound of the present disclosure acts as a low nM partial agonist of the β2 adrenergic receptor and has an $EC_{50}$ of from about 0.001 nM to about 200 nM, 0.001 nM to about 150 nM, about 0.001 nM to about 100 nM, 0.01 nM to about 100 nM, 0.1 nM to about 100 nM, or about 0.1 nM to about 80 nM, or about 0.1 nM to about 60 nM, or about 0.1 nM to about 40 nM, or about 0.1 nM to about 30 nM, or about 0.1 nM to about 20 nM, or about 0.1 nM to about 10 nM.

In some embodiments, a compound of the present disclosure acts as a low µM, partial agonist of the β2 adrenergic receptor. For instance, in some embodiments, a compound of the present disclosure has an $EC_{50}$ of less than about 0.1 µM, less than about 0.5 µM, less than about 1.0 µM, less than about 1.5 µM, less than about 2.0 µM, less than about 2.5 µM, less than about 3.0 µM, less than about 3.5 µM, less than about 4.0 µM, less than about 4.5 µM, less than about 5.0 µM, less than about 5.5 µM, less than about 6.0 µM, less than about 6.5 µM, less than about 7.0 µM, less than about 7.5 µM, less than about 8.0 µM, less than about 8.5 µM, less than about 9.0 µM, less than about 9.5 µM, or less than about 10.0 µM, In some embodiments, a compound of the present disclosure acts as a low µM. partial agonist of the β2 adrenergic receptor and has an $EC_{50}$ of from about 0.01 µM to about 10 µM, about 0.01 µM to about 9.0 µM, about 0.01 µM to about 8.0 µM, about 0.01 µM to about 7.0 µM, about 0.01 µM to about 6.0 µM, about 0.01 µM to about 5.0 µM, about 0.01 µM to about 4.0 µM, about 0.01 µM to about 3.0 µM, about 0.01 µM to about 2.0 µM, about 0.01 µM to about 1.0 µM, about 0.01 µM to about 9.0 µM, about 0.1 µM to about 1.0 µM, In some embodiments of the method, the target adrenergic receptor is a β1-adrenergic receptor. In some embodiments of the method, the target adrenergic receptor is a β2-adrenergic receptor. In some embodiments of the method, the target adrenergic receptor is a β3-adrenergic receptor. In some embodiments, the compound is an agonist for both β1-adrenergic receptor and β2-adrenergic receptor. In certain cases, the compound is selective for the β2-adrenergic receptor over a β1-adrenergic receptor.

The target adrenergic receptor may be one that is responsible for a mediating an intracellular signal or pathway in a cell. In some embodiments, the sample includes a cell and modulating the adrenergic receptor modulates a physiological process in the cell. Any convenient physiological processes can be targeted for modulation in a cell using the subject methods. In some embodiments, the physiological process is one that is implicated in cardiac function, in certain instances, the physiological process is one that is implicated in cognitive function. In certain instances, the physiological process is one that is implicated in an inflammatory pathway or condition. The subject methods can provide for mediation of the intracellular concentration of a signaling molecule in a cell, such as cAMP. The subject methods can provide for partial or full blockage of the target adrenergic receptor to result in modulation (e.g., activation) of cAMP in a sample. In some embodiments, the method does not modulate β-arrestin pathways of the cell. In some cases, the cells are inflammatory cells and the function of the cells is regulated. The subject methods can provide for inhibition of an inflammatory pathway in a cell. In some cases, TNF-alpha is inhibited in the cell, e.g., the concentration or production of TNF-alpha is reduced by practicing the subject method. In certain embodiments of the method, the cell is a neuron. In some embodiments, modulating the adrenergic receptor enhances neurogenesis.

The compounds of this disclosure may be employed in a conventional manner for controlling, preventing, treating a disease described herein, including, but not limited to, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis, cerebral autosomal dominant arteriopathy with subcortical infarcts (CADASIL) and diabetic retinopathy. Such methods of treatment, their dosage levels and requirements may be selected by those of ordinary skill in the art from available methods and techniques.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

In some embodiments, the subject method includes administering a therapeutically effective amount of one or more additional active agents. By combination therapy is meant that an adrenergic receptor modulating compound can be used in a combination with another therapeutic agent to treat a single disease or condition. In particular embodiments, a compound of the present disclosure is administered concurrently with the administration of another therapeutic agent, which can be administered as a component of a composition including the compound of the present disclosure or as a component of a different composition.

The subject compounds can be administered in combination with other therapeutic agents in a variety of therapeutic applications. Therapeutic applications of interest for combination therapy include those applications in which activity of a target adrenergic receptor is the cause or a compounding factor in disease progression. As such, the subject compounds find use in combination therapies in which the inhibition of a target adrenergic receptor in the subject is desired. Examples of disease conditions which may be treated by a combination therapy including a subject compound include, but are not limited to, cardiac conditions or diseases, neurodegenerative or neurodevelopmental disease, respiratory disorders, asthma, memory impairment, depression, inflammatory diseases, stroke, ischemic brain or tissue injury and cancer. Agents of interest which can be used in jointly with the subject adrenergic receptor modulating compounds include, but are not limited to, antidepressants, antipsychotics, beta-blockers, vasoconstrictors, antihypotensives, decongestants, chemotherapeutic agents, agents used in Alzheimer's disease, and anti-inflammatory agents.

The subject adrenergic receptor modulating compounds can be used jointly with any agent useful in the treatment of a cardiac condition, such as cardiogenic shock, hypertension, congestive heart failure, coronary heart disease, arrhythmias, myocardial infarction or ischemic heart diseases. Agents of interest which can be used in jointly with the subject adrenergic receptor modulating compounds include, but are not limited to, denopamine, dobutamine, xamoterol, acebutolol, atenolol, betaxolol, bisoprolol, pindolol, esmolol, metoprolol, nebivolol, vortioxetine, Carvedilol, Labetalol, Phentolamine, Prazosin, Cirazoline, Methoxamine, Synephrine, Etilefrine, Metaraminol, Midodrine, and cumarin.

The subject adrenergic receptor modulating compounds can be used jointly with any agent useful in the treatment of a neurodegenerative or neurodevelopmental disease, such as such as Alzheimer's Disease, memory impairment, cognitive impairment, depression, stroke and ischemic brain or tissue injury, Down's syndrome or Autism. Agents of interest which can be used in jointly with the subject adrenergic receptor modulating compounds include, but are not limited to, acepromazine. In some embodiments, the subject adrenergic receptor modulating compounds can be used in the treatment of a disease, such as a neurodegenerative or neurodevelopmental disease, in combination with a cholinesterase inhibitor or a NMDA receptor modulators. Agents of interest include, but are not limited to, Donepezil, Aricept, Galantamine, Razadyne, Memantine, Namenda, Rivastigmine, Exelon, Tacrine and Cognex. Other agents of interest which can be used in jointly with the subject adrenergic receptor modulating compounds include, but are not limited to, 4-NEMD, 7-Me-marsanidine, Agmatine, Apraclonidine, Brimonidine, Cannabigerol, Clonidine, Detomidine, Dexmedetomidine, Fadolmidine, Guanabenz, Guanfacine, Lofexidine, Marsanidine, Medetomidine, Methamphetamine, Mivazerol, Rilmenidine, Romifidine, Talipexole, Tiamenidine, Tizanidine, Tolonidine, Xylazine, Xylometazoline, Aripiprazole, Asenapine, Atipamezole, Cirazoline, Clozapine, Efaroxan, Idazoxan, Lurasidone, Melperone, Mianserin, Mirtazapine, Napitane, Olanzapine, Paliperidone, Phenoxybenzamine, Phentolamine, Piribedil, Rauwolscine, Risperidone, Rotigotine, Quetiapine, Norquetiapine, Setiptiline, Tolazoline, Yohimbine, Ziprasidone and Zotepine. Other agents of interest which can be used in jointly with the subject adrenergic receptor modulating compounds include, but are not limited to, bitolterol, fenoterol, hexoprenaline, isoprenaline or isoproterenol, levosalbutamol or levalbuterol, orciprenaline or metaproterenol, pirbuterol, procaterol, salbutamol or albuterol, terbutaline, bambuterol, clenbuterol, formoterol, salmeterol, carmoterol, indacaterol, milveterol, olodaterol, vilanterol, fenoterol, hexoprenaline, isoxsuprine, ritodrine, salbutamol or albuterol, terbutaline, zilpaterol, ICI-118,551 and butoxamine.

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to stroke, ischemia, Alzheimer's, ankylosing spondylitis, arthritis, osteoarthritis, rheumatoid arthritis, psoriatic arthritis, asthma atherosclerosis, Crohn's disease, colitis, dermatitis diverticulitis, fibromyalgia, hepatitis, irritable bowel syndrome, systemic lupus erythematous, nephritis, ulcerative colitis and Parkinson's disease. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/orantifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

Also provided are kits that include the disclosed adrenergic receptor modulating compounds. Systems of the present disclosure include collections of active agents brought together, e.g., by a health care practitioner, for administration to a subject, such as a patient. Such systems may include an adrenergic receptor modulating compound and one or more additional active agents disclosed herein. Kits that include adrenergic receptor modulating compounds which are provided that may include one or more dosages of an adrenergic receptor modulating compound, and optionally one or more dosages of one or more additional active agents. Conveniently, the formulations may be provided in a unit dosage format. In such kits, in addition to the containers containing the formulation(s), e.g. unit doses, is an informational package insert describing the use of the subject formulations in the methods of the as disclosed herein, e.g., instructions for using the subject unit doses to treat cellular proliferative disease conditions. These instructions may be present in the subject systems and kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Table 1 below illustrates the compounds synthesized and characterized in the instant disclosure. Table 1 also illustrates representative compounds contemplated by the instant disclosure.

TABLE 1

The compound in the instant disclosure.

| Compound No. | Chemical Structure | MS (m/z) (M + 1) |
|---|---|---|
| 03-1 | 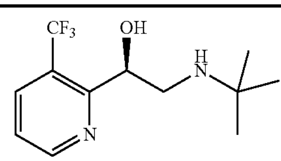 | 263.2 |
| 03-2 | 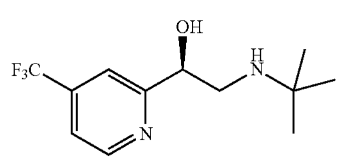 [SMILES: CC(C)(C)NC[C@H](O)c1cc(C(F)(F)F)ccn1] | 263.2 |

TABLE 1-continued
The compound in the instant disclosure.
| Compound No. | Chemical Structure | MS (m/z) (M + 1) |
|---|---|---|
| 03-3 | 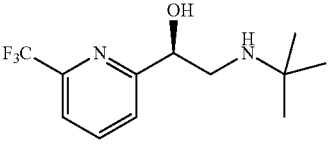 [SMILES: CC(C)(C)NC[C@H](O)c1cccc(C(F)(F)F)n1] | 263.2 |
| 03-4 | 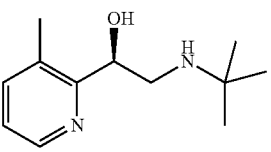 | 209.2 |
| 03-5 | 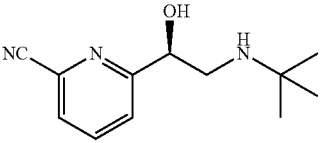 [SMILES: CC(C)(C)NC[C@H](O)c1cccc(C#N)n1] | 220.24 |
| 03-6 | 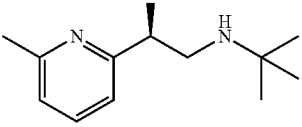 | 209.32 |
| 03-7 | 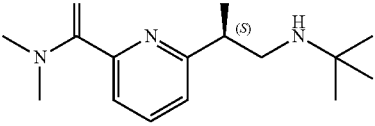 | 266.1 |
| 03-8 | 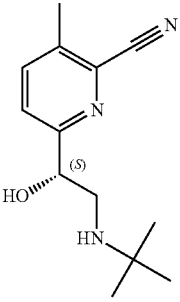 | 234.23 |
| 03-9 | 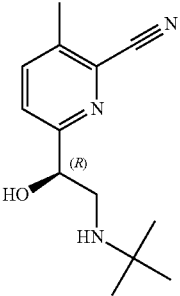 | 234.23 |

TABLE 1-continued

The compound in the instant disclosure.

| Compound No. | Chemical Structure | MS (m/z) (M + 1) |
|---|---|---|
| 03-10 | 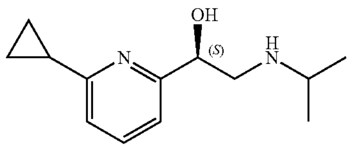 | 221.1 |
| 03-11 | 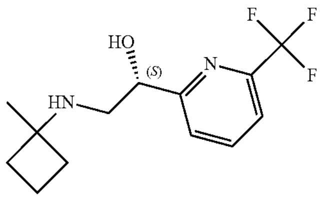 | 275.17 |
| 03-12 | 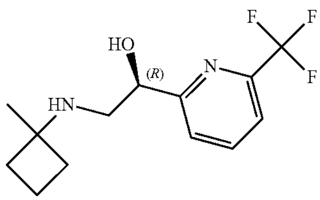 | 275.17 |
| 03-13 | 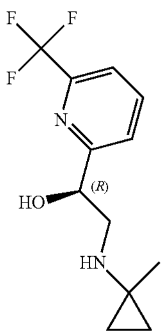 | 261.14 |
| 03-14 | 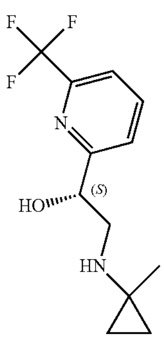 | 261.14 |
| 03-15 | 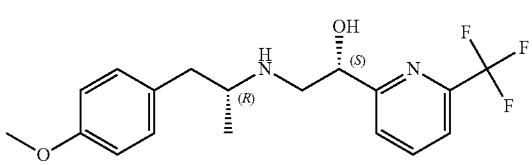 | 355.32 |
| 03-16 | 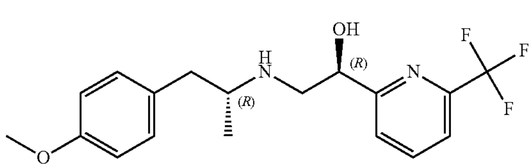 | 355.32 |

TABLE 1-continued

The compound in the instant disclosure.

| Compound No. | Chemical Structure | MS (m/z) (M + 1) |
|---|---|---|
| 03-17 | 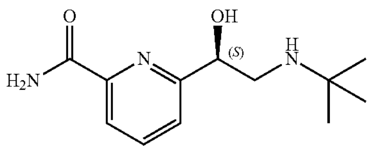 | 238.1 |
| 03-18 | 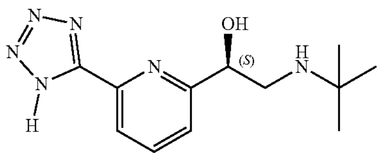 | 263.2 |
| 03-19 | 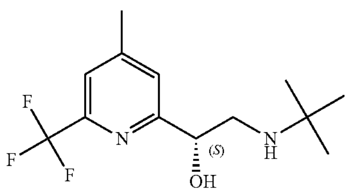 | 277.1 |
| 03-20 | 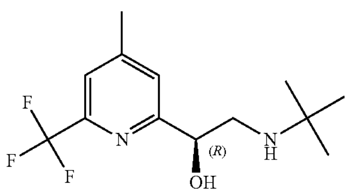 | 277.1 |
| 03-21 | 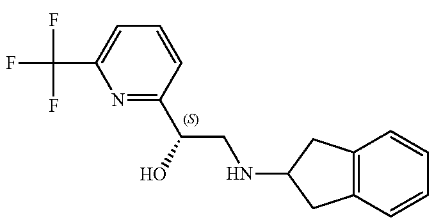 | 323.27 |
| 03-22 | 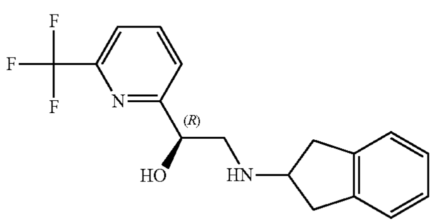 | 323.27 |
| 03-23 | 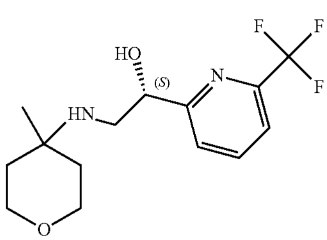 | 305.25 |

TABLE 1-continued

| Compound No. | Chemical Structure | MS (m/z) (M + 1) |
|---|---|---|
| 03-24 | 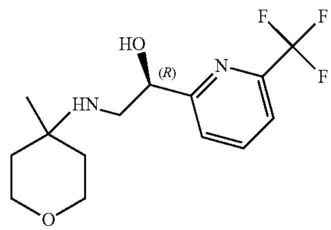 | 305.25 |
| 03-25 | 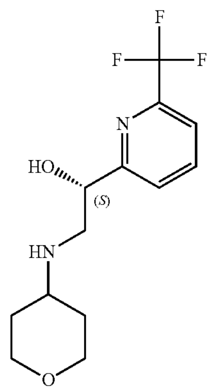 | 291.18 |
| 03-26 | 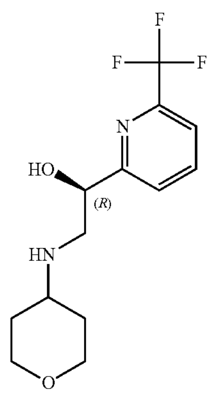 | 291.18 |
| 03-28 | 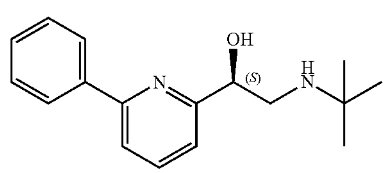 | 271.1 |
| 03-29 | 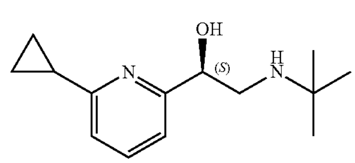 | 253.2 |

TABLE 1-continued

The compound in the instant disclosure.

| Compound No. | Chemical Structure | MS (m/z) (M + 1) |
|---|---|---|
| 03-30 | 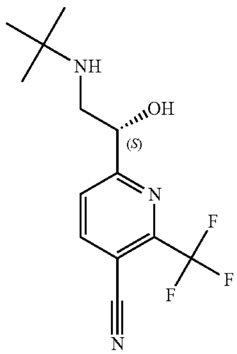 | 288.25 |
| 03-31 | 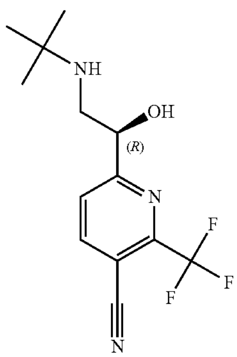 | 288.25 |
| 03-32 | 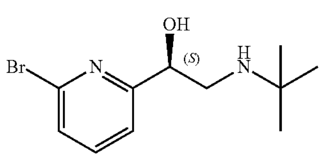 | 273.1 |
| 03-33 | 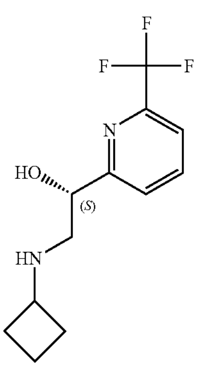 | 261.24 |

TABLE 1-continued

The compound in the instant disclosure.

| Compound No. | Chemical Structure | MS (m/z) (M + 1) |
|---|---|---|
| 03-34 | 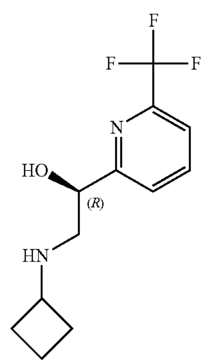 | 261.24 |
| 03-35 | 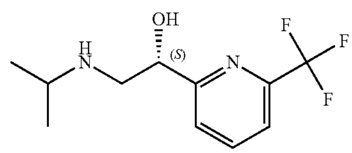 | 249.17 |
| 03-36 | 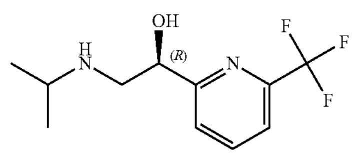 | 249.17 |
| 03-37 | 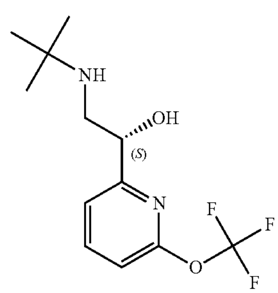 | 279.17 |
| 03-38 | 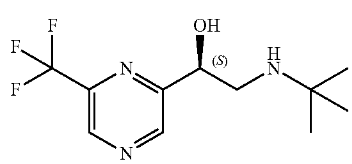 | 264.1 |
| 03-43 | 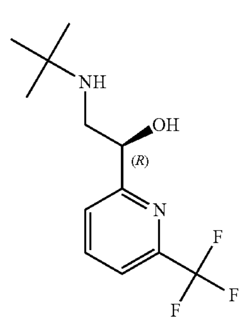 | 263.2 |

TABLE 1-continued

The compound in the instant disclosure.

| Compound No. | Chemical Structure | MS (m/z) (M + 1) |
|---|---|---|
| 03-44 | (structure) | 245.1 |
| 03-45 | (structure) | 264.1 |
| 03-46 | (structure) | 263.1 |
| 03-47 | (structure) | 209.32 |
| 03-48 | (structure) | 220.25 |
| 03-49 | (structure) | 272.1 |
| 03-50 | (structure) | 229.2 |

TABLE 1-continued

The compound in the instant disclosure.

| Compound No. | Chemical Structure | MS (m/z) (M + 1) |
|---|---|---|
| 03-51 | 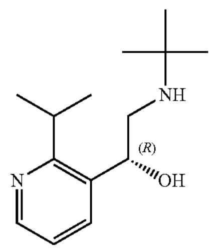 | 237.2 |
| 03-52 | 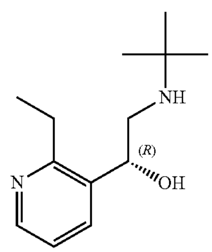 | 223.2 |
| 03-53 | 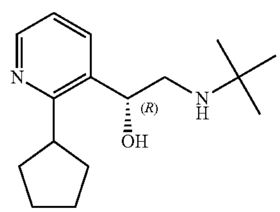 | 263.2 |
| 03-54 | 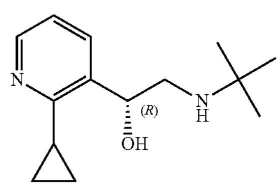 | 235.3 |
| 03-55 | 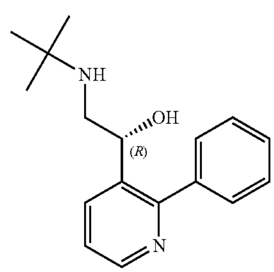 | 271.4 |
| 03-56 | 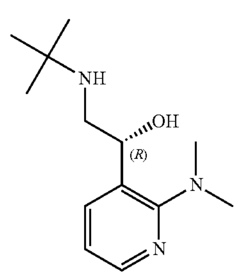 | 238.2 |

TABLE 1-continued

The compound in the instant disclosure.

| Compound No. | Chemical Structure | MS (m/z) (M + 1) |
|---|---|---|
| 03-57 | 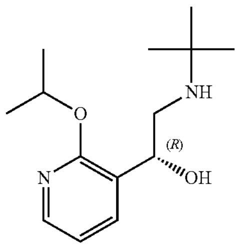 | 253.2 |
| 03-58 | 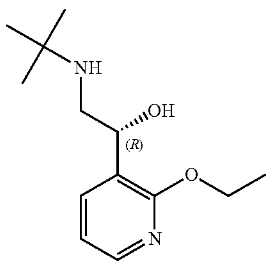 | 239.2 |
| 03-59 | 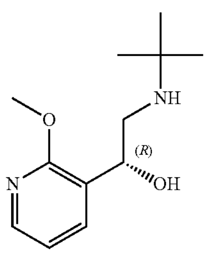 | 225.2 |
| 03-60 | 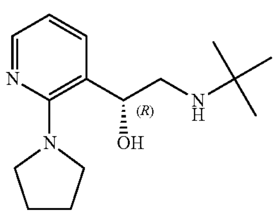 | 264.2 |
| 03-61 | 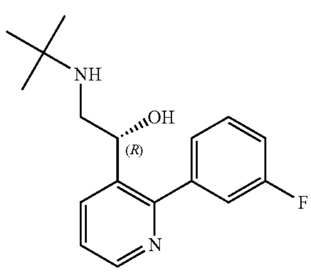 | 289.3 |
| 03-62 | 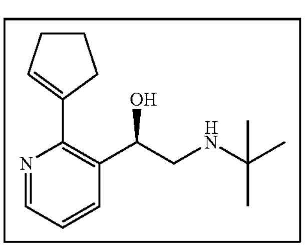 [SMILES: CC(C)(C)NC[C@H](O)c1cccnc1C1=CCCC1] | 261.4 |

TABLE 1-continued

The compound in the instant disclosure.

| Compound No. | Chemical Structure | MS (m/z) (M + 1) |
|---|---|---|
| 03-63 | 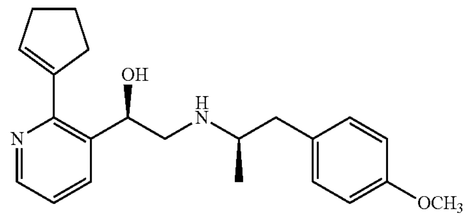 [SMILES: COc1ccc(C[C@@H](C)NC[C@H](O)c2cccnc2C2=CCCC2)cc1] | 353.5 |
| 03-64 | 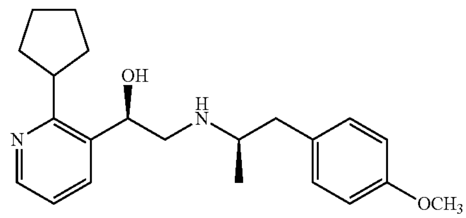 [SMILES: COc1ccc(C[C@@H](C)NC[C@H](O)c2cccnc2C2CCCC2)cc1] | 355.5 |
| 03-65 | 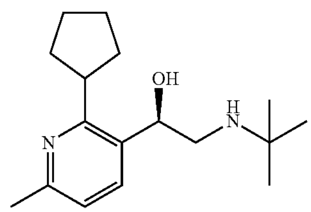 [SMILES: Cc1ccc([C@@H](O)CNC(C)(C)C)c(C2CCCC2)n1] | 277.4 |
| 03-66 | 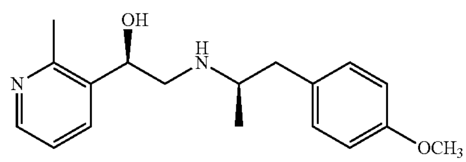 [SMILES: COc1ccc(C[C@@H](C)NC[C@H](O)c2cccnc2C)cc1] | 301.3 |
| 03-67 | 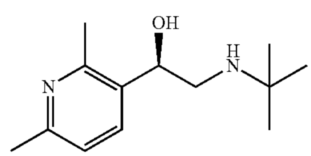 [SMILES: Cc1ccc([C@@H](O)CNC(C)(C)C)c(C)n1] | 223.3 |
| 03-68 | 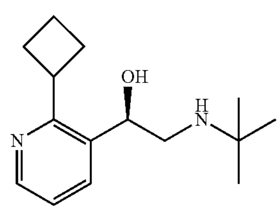 [SMILES: CC(C)(C)NC[C@H](O)c1cccnc1C1CCC1] | 249.3 |
| 03-70 | 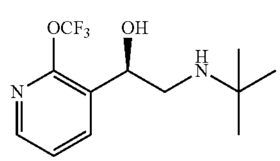 [SMILES: CC(C)(C)NC[C@H](O)c1cccnc1OC(F)(F)F] | 279.3 |
| 03-71 | 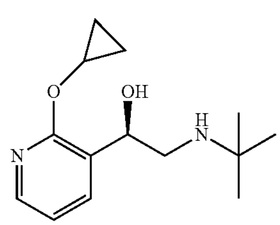 [SMILES: CC(C)(C)NC[C@H](O)c1cccnc1OC1CC1] | 251.3 |

TABLE 1-continued

The compound in the instant disclosure.

| Compound No. | Chemical Structure | MS (m/z) (M + 1) |
|---|---|---|
| 03-72 | 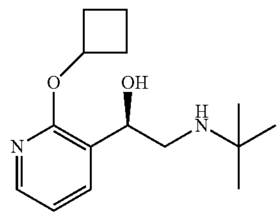 [SMILES: CC(C)(C)NC[C@H](O)c1cccnc1OC1CCC1] | 265.3 |
| 03-73 | 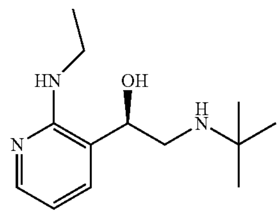 [SMILES: CCNc1ncccc1[C@@H](O)CNC(C)(C)C] | 238.4 |
| 03-74 | 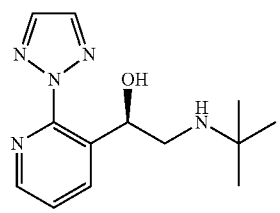 [SMILES: CC(C)(C)NC[C@H](O)c1cccnc1-n1nccn1] | 262.2 |
| 03-75 | 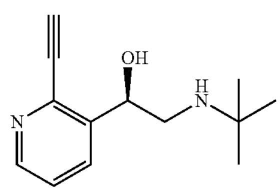 [SMILES: C#Cc1ncccc1[C@@H](O)CNC(C)(C)C] | 219.3 |
| 03-76 | 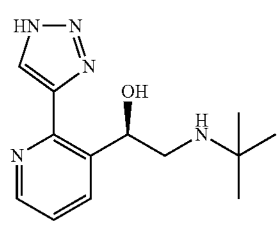 [SMILES: CC(C)(C)NC[C@H](O)c1cccnc1-c1c[nH]nn1] | 262.3 |
| 03-77 | 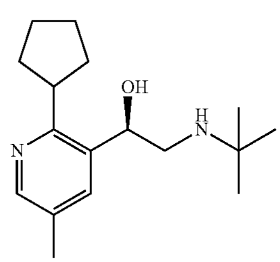 [SMILES: Cc1cnc(C2CCCC2)c([C@@H](O)CNC(C)(C)C)c1] | 277.4 |

TABLE 1-continued

The compound in the instant disclosure.

| Compound No. | Chemical Structure | MS (m/z) (M + 1) |
|---|---|---|
| 03-78 | 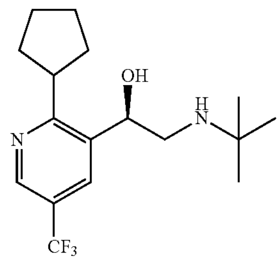 [SMILES: CC(C)(C)NC[C@H](O)c1cc(C(F)(F)F)cnc1C1CCCC1] | 331.3 |
| 03-79 | 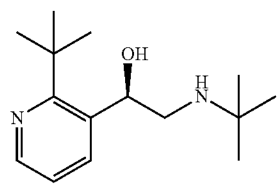 [SMILES: CC(C)(C)NC[C@H](O)c1cccnc1C(C)(C)C] | 251.4 |
| 03-80 | 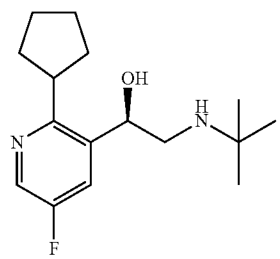 [SMILES: CC(C)(C)NC[C@H](O)c1cc(F)cnc1C1CCCC1] | 281.4 |
| 03-81 | 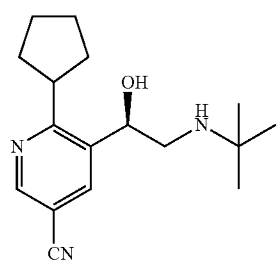 [SMILES: CC(C)(C)NC[C@H](O)c1cc(C#N)cnc1C1CCCC1] | |
| 03-82 | 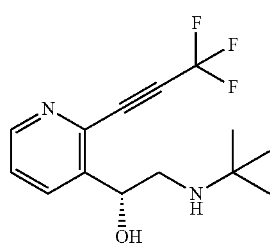 [SMILES: CC(C)(C)NC[C@H](O)c1cccnc1C#CC(F)(F)F] | |
| 03-83 | 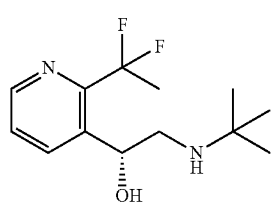 [SMILES: CC(C)(C)NC[C@H](O)c1cccnc1C(C)(F)F] | 259.3 |

TABLE 1-continued

The compound in the instant disclosure.

| Compound No. | Chemical Structure | MS (m/z) (M + 1) |
| --- | --- | --- |
| 03-84 | 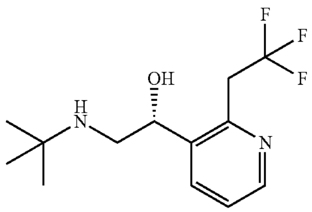 [SMILES: CC(C)(C)NC[C@H](O)c1cccnc1CC(F)(F)F] | 277.3 |
| 03-85 | 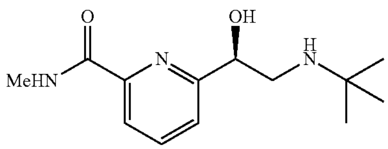 [SMILES: CNC(=O)c1cccc([C@@H](O)CNC(C)(C)C)n1] | 252.2 |
| 03-86 | 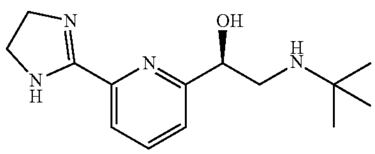 [SMILES: CC(C)(C)NC[C@H](O)c1cccc(C2=NCCN2)n1] | 263.1 |
| 03-87 | 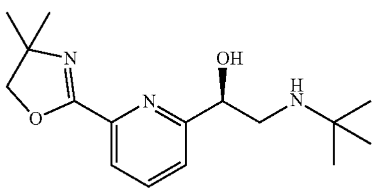 [SMILES: CC1(C)COC(c2cccc([C@@H](O)CNC(C)(C)C)n2)=N1] | 275.3 |
| 03-88 | 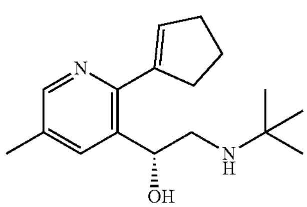 [SMILES: Cc1cnc(C2=CCCC2)c([C@@H](O)CNC(C)(C)C)c1] | 275.3 |
| 03-89 | 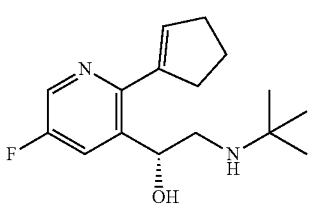 [SMILES: CC(C)(C)NC[C@H](O)c1cc(F)cnc1C1=CCCC1] | 279.4 |
| 03-90 | 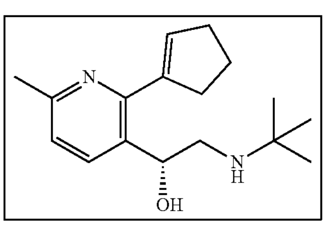 [SMILES: Cc1ccc([C@@H](O)CNC(C)(C)C)c(C2=CCCC2)n1] | 275.4 |

TABLE 1-continued
The compound in the instant disclosure.
| Compound No. | Chemical Structure | MS (m/z) (M + 1) |
|---|---|---|
| 03-91 | 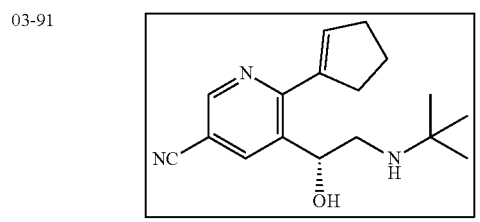 | |
| 03-92 | 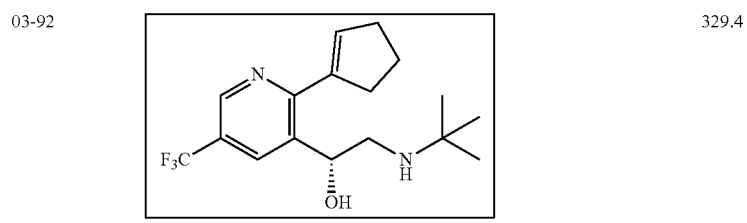 | 329.4 |
| 03-93 | 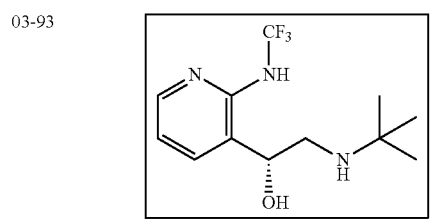 | |
| 03-94 | 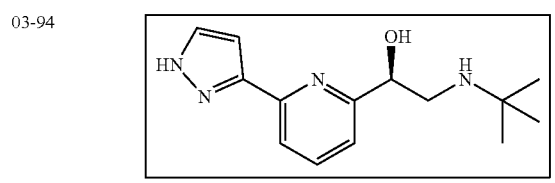 | |
| 03-95 | 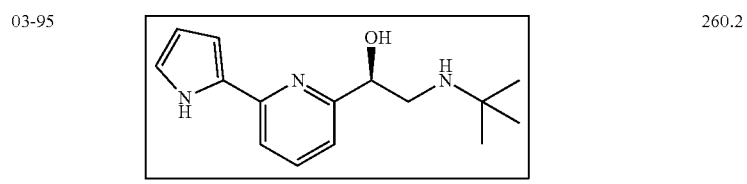 | 260.2 |
| 03-96 | 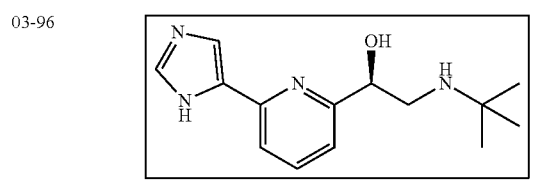 | |
| 03-97 | 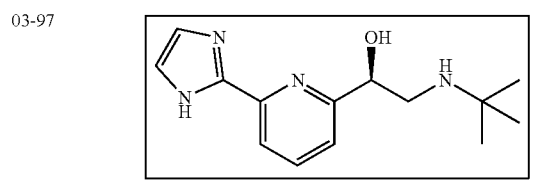 | |

TABLE 1-continued

The compound in the instant disclosure.

| Compound No. | Chemical Structure | MS (m/z) (M + 1) |
|---|---|---|
| 03-98 | 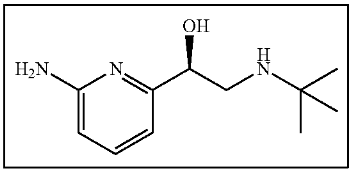 | 210.1 |
| 03-99 | 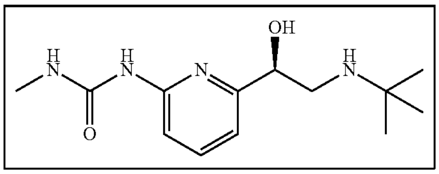 [SMILES: CNC(=O)Nc1cccc([C@@H](O)CNC(C)(C)C)n1] | |
| 03-100 | 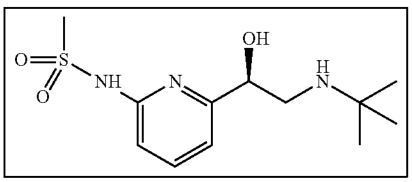 [SMILES: CC(C)(C)NC[C@H](O)c1cccc(NS(C)(=O)=O)n1] | |
| 03-101 | 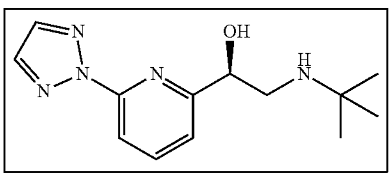 [SMILES: CC(C)(C)NC[C@H](O)c1cccc(-n2nccn2)n1] | 262.2 |
| 03-102 | 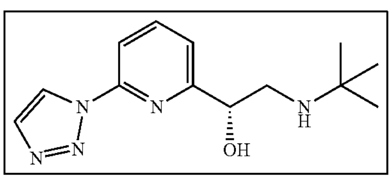 [SMILES: CC(C)(C)NC[C@H](O)c1cccc(-n2ccnn2)n1] | 262.2 |
| 03-103 | 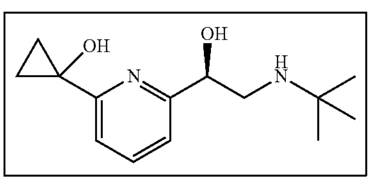 [SMILES: CC(C)(C)NC[C@H](O)c1cccc(C2(O)CC2)n1] | |
| 03-104 | 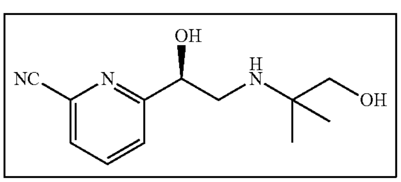 [SMILES: CC(C)(CO)NC[C@H](O)c1cccc(C#N)n1] | 236.2 |
| 03-105 | 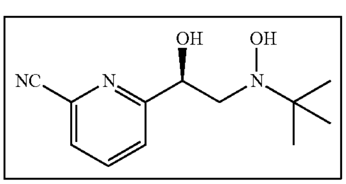 [SMILES: CC(C)(C)N(O)C[C@H](O)c1cccc(C#N)n1] | |

TABLE 1-continued
The compound in the instant disclosure.
| Compound No. | Chemical Structure | MS (m/z) (M + 1) |
|---|---|---|
| 03-106 | 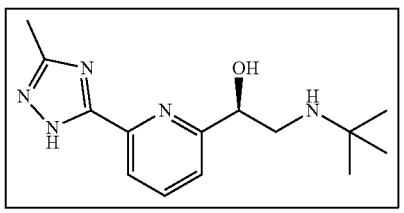 [SMILES: Cc1n[nH]c(-c2cccc([C@@H](O)CNC(C)(C)C)n2)n1] | |
| 03-107 | 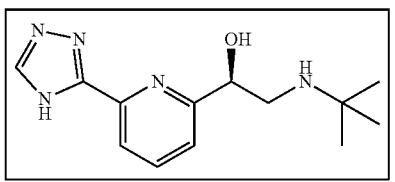 [SMILES: CC(C)(C)NC[C@H](O)c1cccc(-c2nnc[nH]2)n1] | |
| 03-108 | 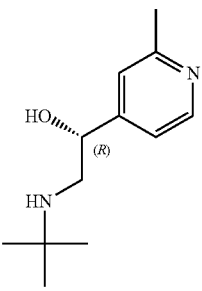 | 209.2 |
| 03-109 | 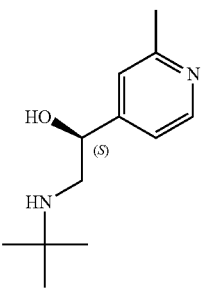 | 209.2 |
| 03-110 | 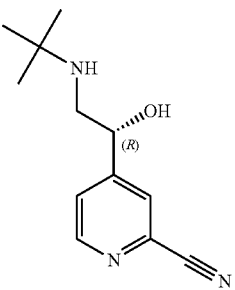 | 220.2 |

TABLE 1-continued
The compound in the instant disclosure.
| Compound No. | Chemical Structure | MS (m/z) (M + 1) |
|---|---|---|
| 03-111 | 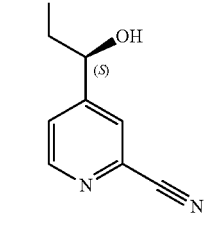 | 220.2 |
| 03-112 | 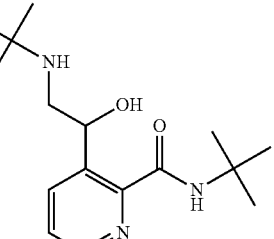 | 294.2 |
| 03-113 | 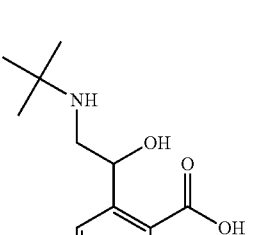 | 239.23 |
| 03-114 | 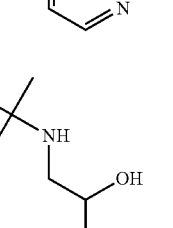 | 229.1 |
| 03-115 | 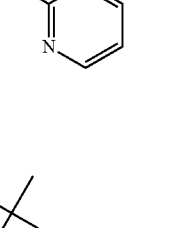 | 209.2 |

TABLE 1-continued

The compound in the instant disclosure.

| Compound No. | Chemical Structure | MS (m/z) (M + 1) |
|---|---|---|
| 03-116 | 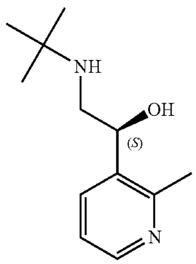 | 209.2 |
| 03-117 | 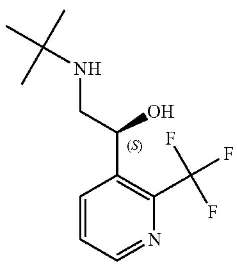 | 263.2 |
| 03-118 | 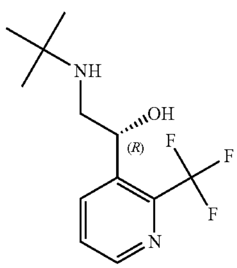 | 263.2 |
| 03-119 | 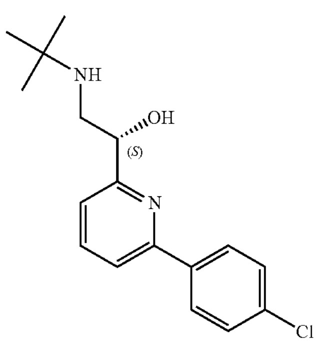 | 305.37 |
| 03-120 | 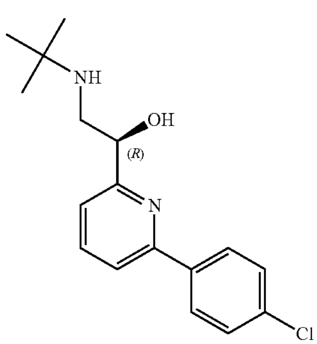 | 305.37 |

TABLE 1-continued

The compound in the instant disclosure.

| Compound No. | Chemical Structure | MS (m/z) (M + 1) |
|---|---|---|
| 03-121 | (S)-1-(6-(tetrahydro-2H-pyran-4-yl)pyridin-2-yl)-2-(tert-butylamino)ethanol | 279.3 |
| 03-122 | (R)-1-(6-(tetrahydro-2H-pyran-4-yl)pyridin-2-yl)-2-(tert-butylamino)ethanol | 279.3 |
| 03-123 | (S)-2-(tert-butylamino)-1-(6-(1H-pyrrol-1-yl)pyridin-2-yl)ethanol | 260.27 |
| 03-124 | (R)-2-(tert-butylamino)-1-(6-(1H-pyrrol-1-yl)pyridin-2-yl)ethanol | 260.23 |

TABLE 1-continued

The compound in the instant disclosure.

| Compound No. | Chemical Structure | MS (m/z) (M + 1) |
|---|---|---|
| 03-125 | (R)-1-(5-(trifluoromethyl)pyridin-2-yl)-2-(tert-butylamino)ethan-1-ol | 263.1 |
| 03-126 | (S)-1-(5-(trifluoromethyl)pyridin-2-yl)-2-(tert-butylamino)ethan-1-ol | 263.1 |
| 03-127 | (S)-2-(tert-butylamino)-1-(5-methylpyridin-2-yl)ethan-1-ol | 209.1 |
| 03-128 | (R)-2-(tert-butylamino)-1-(5-methylpyridin-2-yl)ethan-1-ol | 209.1 |

TABLE 1-continued
The compound in the instant disclosure.
| Compound No. | Chemical Structure | MS (m/z) (M + 1) |
|---|---|---|
| 03-129 | 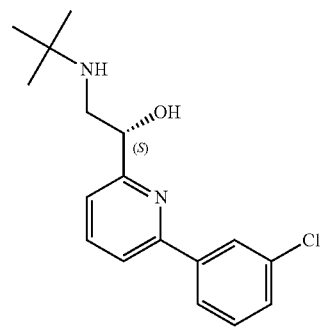 | 305.32 |
| 03-130 | 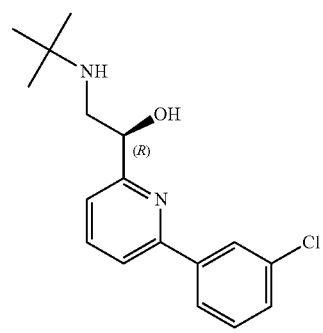 | 305.35 |
| 03-131 | 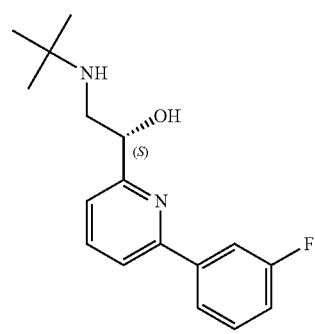 | 289.35 |
| 03-132 | 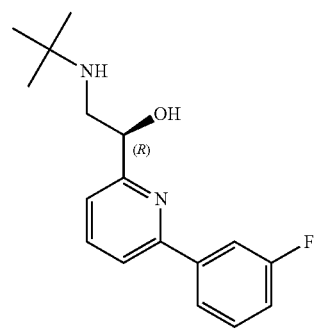 | 289.32 |

TABLE 1-continued

The compound in the instant disclosure.

| Compound No. | Chemical Structure | MS (m/z) (M + 1) |
|---|---|---|
| 03-133 | 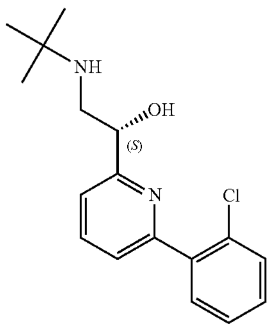 | 305.28 |
| 03-134 | 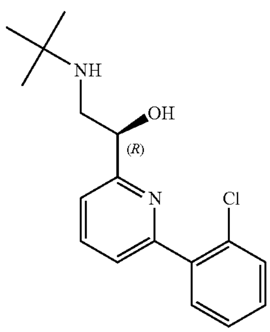 | 305.28 |
| 03-135 | 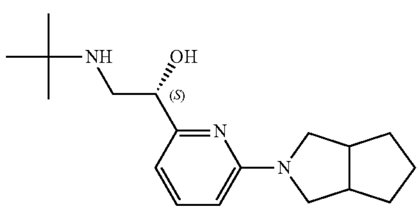 | 304.4 |
| 03-136 | 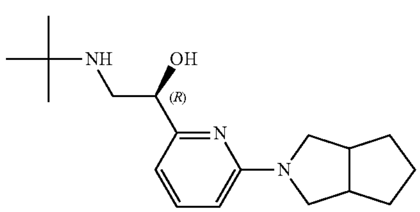 | 304.4 |
| 03-137 | 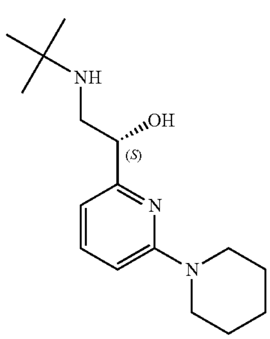 | 278.41 |

TABLE 1-continued
The compound in the instant disclosure.
| Compound No. | Chemical Structure | MS (m/z) (M + 1) |
|---|---|---|
| 03-138 | 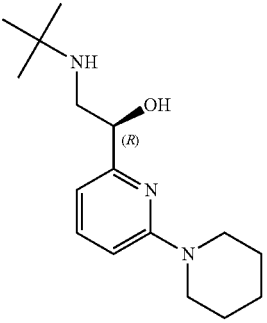 | 278.41 |
| 03-139 | 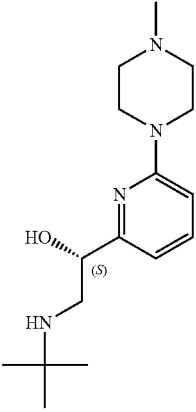 | 293.42 |
| 03-140 | 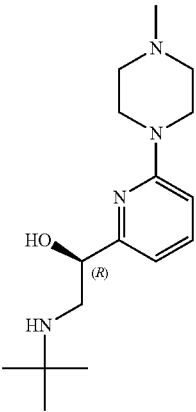 | 293.42 |
| 03-141 | 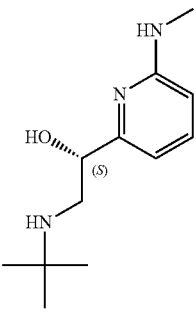 | 224.25 |

TABLE 1-continued

The compound in the instant disclosure.

| Compound No. | Chemical Structure | MS (m/z) (M + 1) |
|---|---|---|
| 03-142 | 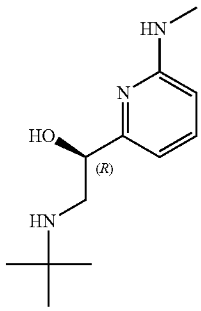 | 224.25 |
| 03-143 | 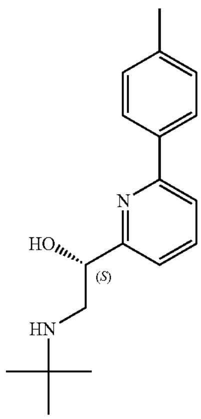 | 285.22 |
| 03-144 | 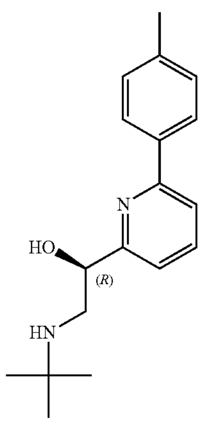 | 285.22 |
| 03-145 | 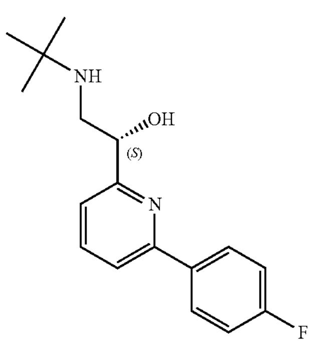 | 289.38 |

TABLE 1-continued

The compound in the instant disclosure.

| Compound No. | Chemical Structure | MS (m/z) (M + 1) |
|---|---|---|
| 03-146 | 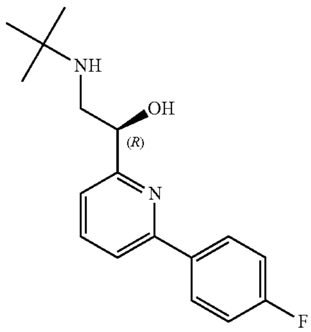 | 289.38 |
| 03-147 | 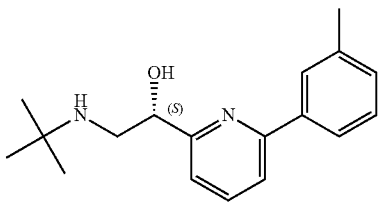 | 285.35 |
| 03-148 | 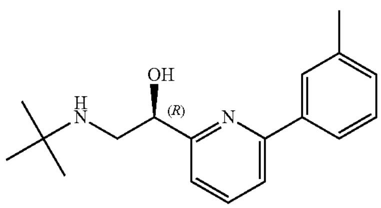 | 285.35 |
| 03-149 | 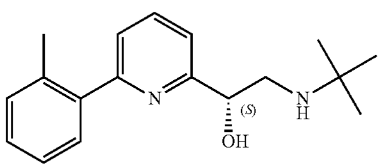 | 285.33 |
| 03-150 | 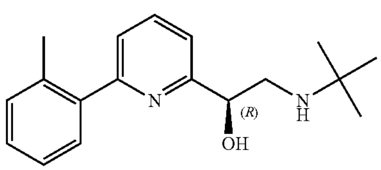 | 285.33 |
| 03-151 | 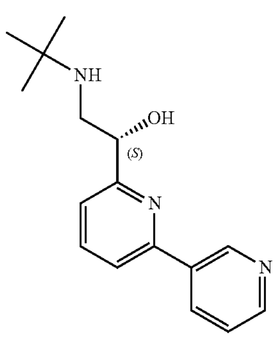 | 272.33 |

TABLE 1-continued

The compound in the instant disclosure.

| Compound No. | Chemical Structure | MS (m/z) (M + 1) |
|---|---|---|
| 03-152 | 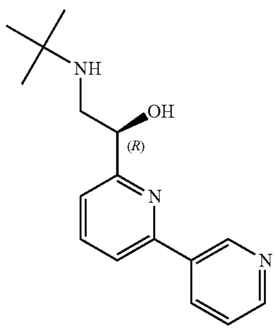 | 272.33 |
| 03-153 | 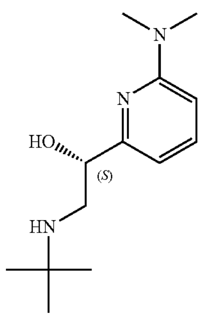 | 238.1 |
| 03-154 | 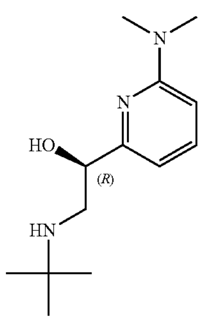 | 238.1 |
| 03-155 | 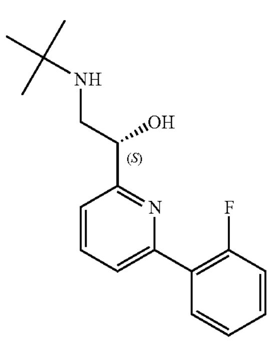 | 289.29 |

TABLE 1-continued

The compound in the instant disclosure.

| Compound No. | Chemical Structure | MS (m/z) (M + 1) |
|---|---|---|
| 03-156 | 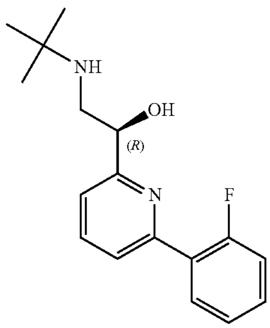 | 289.29 |
| 03-157 | 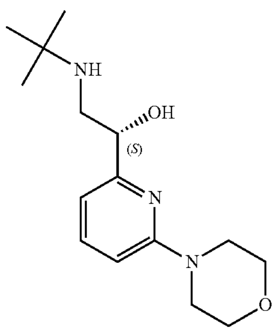 | 280.32 |
| 03-158 | 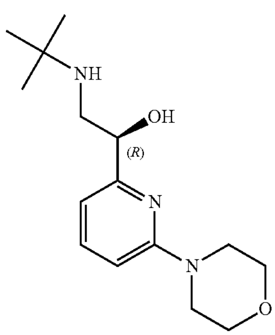 | 280.32 |
| 03-159 | 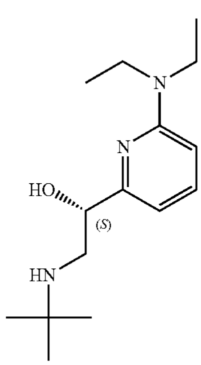 | 266.32 |

TABLE 1-continued

The compound in the instant disclosure.

| Compound No. | Chemical Structure | MS (m/z) (M + 1) |
|---|---|---|
| 03-160 | 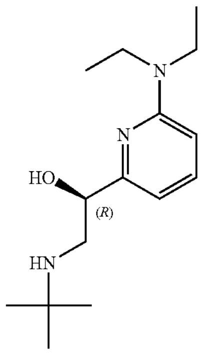 | 266.32 |
| 03-161 | 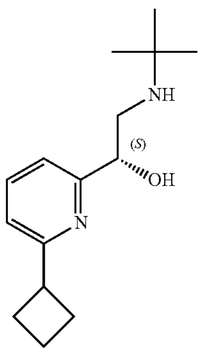 | 249.18 |
| 03-162 | 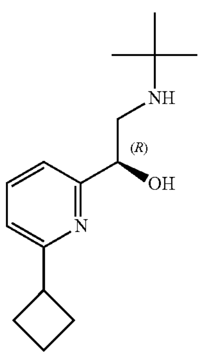 | 249.18 |
| 03-163 | 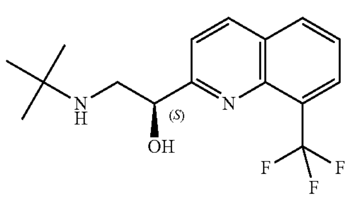 | 313.26 |
| 03-164 | 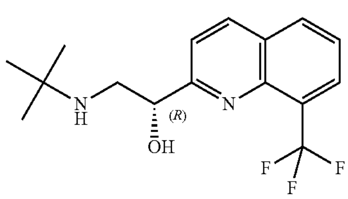 | 313.26 |

TABLE 1-continued

The compound in the instant disclosure.

| Compound No. | Chemical Structure | MS (m/z) (M + 1) |
|---|---|---|
| 03-165 | 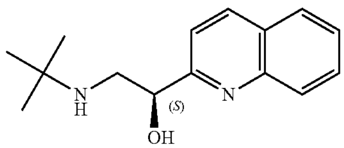 | 245.1 |
| 03-166 | 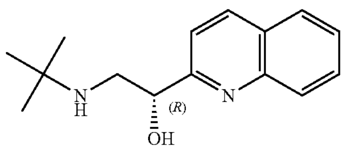 | 245.1 |
| 03-167 | 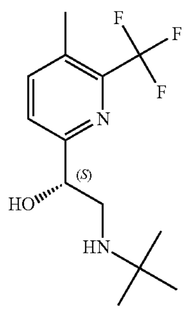 | 277.1 |
| 03-168 | 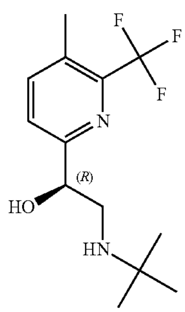 | 277.1 |
| 03-169 | 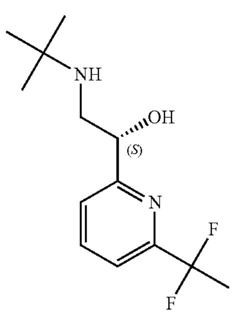 | 259.13 |
| 03-170 | 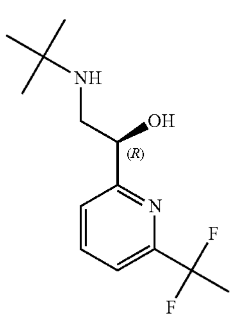 | 259.13 |

TABLE 1-continued

The compound in the instant disclosure.

| Compound No. | Chemical Structure | MS (m/z) (M + 1) |
|---|---|---|
| 03-171 | 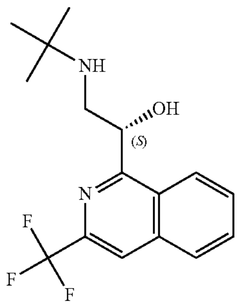 | 313.28 |
| 03-172 | 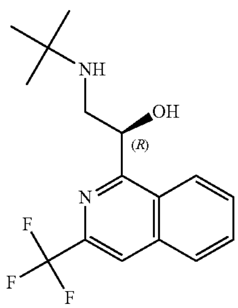 | 313.28 |
| 03-173 | 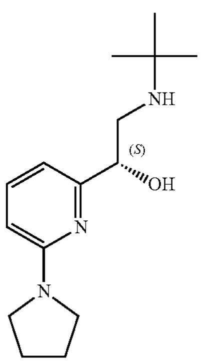 | 264.3 |
| 03-174 | 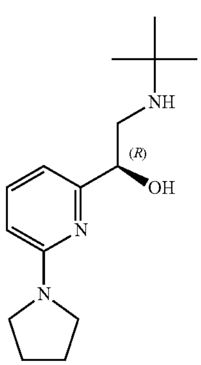 | 264.3 |

TABLE 1-continued
The compound in the instant disclosure.
| Compound No. | Chemical Structure | MS (m/z) (M + 1) |
|---|---|---|
| 03-175 | 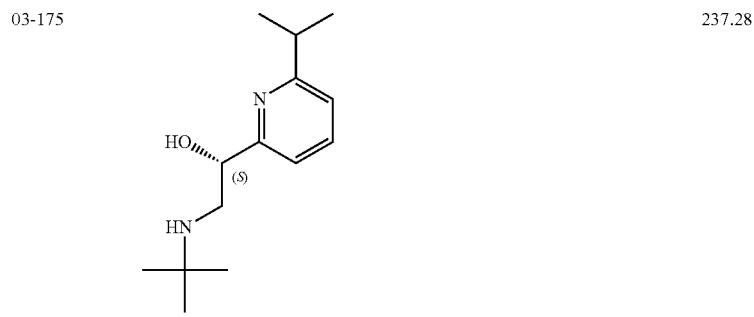 | 237.28 |
| 03-176 | 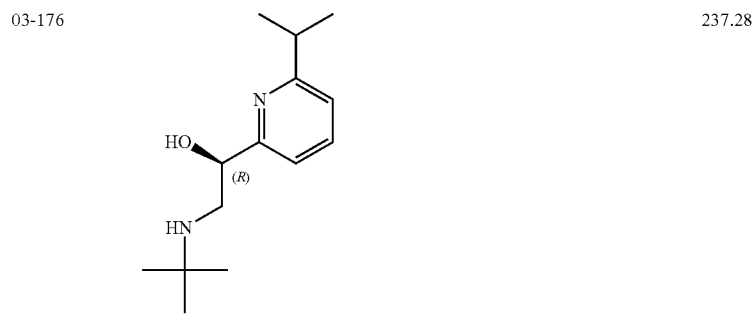 | 237.28 |
| 03-177 | 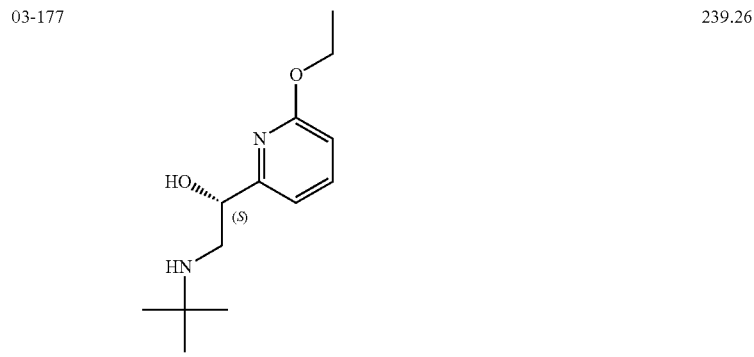 | 239.26 |
| 03-178 | 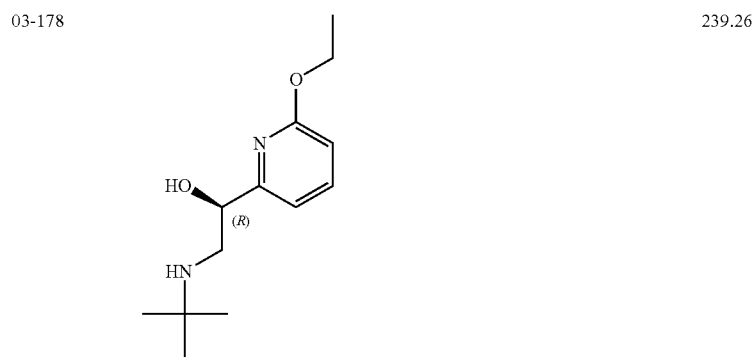 | 239.26 |

TABLE 1-continued

The compound in the instant disclosure.

| Compound No. | Chemical Structure | MS (m/z) (M + 1) |
|---|---|---|
| 03-179 | (S)-1-(6-isopropoxypyridin-2-yl)-2-(tert-butylamino)ethanol | 253.2 |
| 03-180 | (R)-1-(6-isopropoxypyridin-2-yl)-2-(tert-butylamino)ethanol | 253.2 |
| 03-181 | 2-(2-(tert-butylamino)-1-hydroxyethyl)-6-(trifluoromethyl)isonicotinonitrile | 288.23 |
| 03-182 | (S)-1-(6-(trifluoromethyl)pyridin-2-yl)-2-((2-(4-methoxyphenyl)propan-2-yl)amino)ethanol | 369.26 |

TABLE 1-continued
The compound in the instant disclosure.
| Compound No. | Chemical Structure | MS (m/z) (M + 1) |
|---|---|---|
| 03-183 | 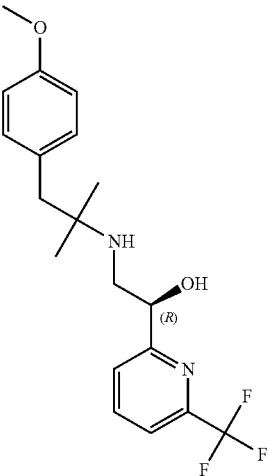 | 369.26 |
| 03-184 | 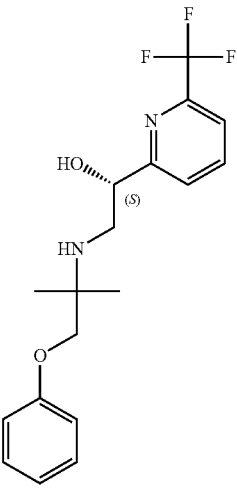 | 355.32 |
| 03-185 | 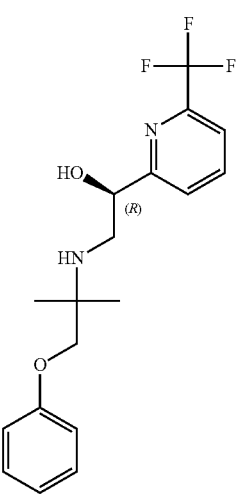 | 355.32 |

TABLE 1-continued

The compound in the instant disclosure.

| Compound No. | Chemical Structure | MS (m/z) (M + 1) |
|---|---|---|
| 03-186 | (R)-1-(6-(trifluoromethoxy)pyridin-2-yl)-2-(tert-butylamino)ethanol structure | 279.17 |
| 03-187 | (R)-1-(isoquinolin-1-yl)-2-(tert-butylamino)ethanol structure | 245.1 |
| 03-188 | (S)-1-(isoquinolin-1-yl)-2-(tert-butylamino)ethanol structure | 245.1 |
| 03-189 | 1-(6-(cyclopropylamino)pyridin-2-yl)-2-(tert-butylamino)ethanol structure | 250.2 |
| 03-190 | 1-(6-(cyclobutylamino)pyridin-2-yl)-2-(tert-butylamino)ethanol structure | 264.3 |
| 03-191 | 1-(6-(cyclopentylamino)pyridin-2-yl)-2-(tert-butylamino)ethanol structure | 278.4 |
| 03-192 | 1-(6-(isopropylamino)pyridin-2-yl)-2-(tert-butylamino)ethanol structure | 252.3 |

TABLE 1-continued

The compound in the instant disclosure.

| Compound No. | Chemical Structure | MS (m/z) (M + 1) |
|---|---|---|
| 03-193 | 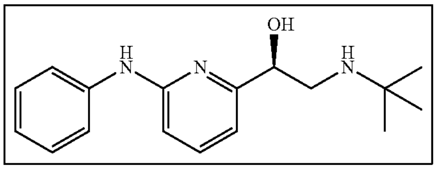 [SMILES: CC(C)(C)NC[C@H](O)c1cccc(Nc2ccccc2)n1] | 286.3 |
| 03-194 | 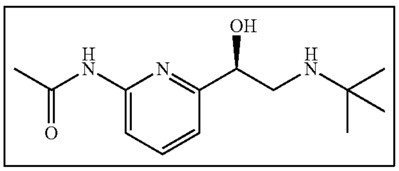 [SMILES: CC(=O)Nc1cccc([C@@H](O)CNC(C)(C)C)n1] | 252.3 |
| 03-195 | 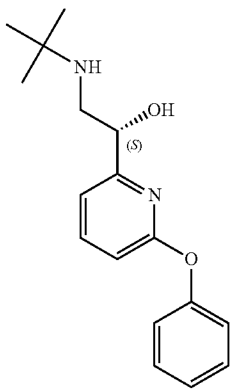 | 287.2 |
| 03-196 | 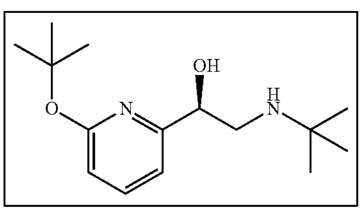 [SMILES: CC(C)(C)NC[C@H](O)c1cccc(OC(C)(C)C)n1] | 267.2 |
| 03-197 | 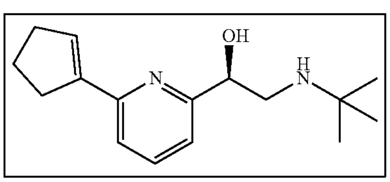 [SMILES: CC(C)(C)NC[C@H](O)c1cccc(C2=CCCC2)n1] | 261.3 |
| 03-198 | 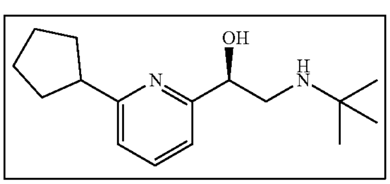 [SMILES: CC(C)(C)NC[C@H](O)c1cccc(C2CCCC2)n1] | 263.3 |
| 03-199 | 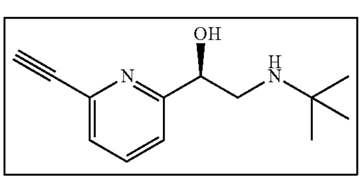 [SMILES: C#Cc1cccc([C@@H](O)CNC(C)(C)C)n1] | 219.2 |

TABLE 1-continued

The compound in the instant disclosure.

| Compound No. | Chemical Structure | MS (m/z) (M + 1) |
|---|---|---|
| 03-200 | 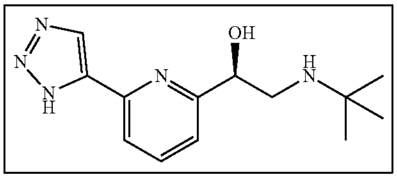 [SMILES: CC(C)(C)NC[C@H](O)c1cccc(-c2cnn[nH]2)n1] | 262.2 |
| 03-201 | 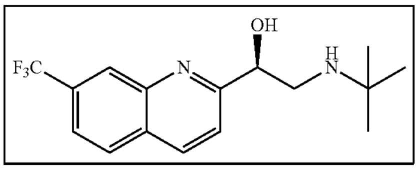 [SMILES: CC(C)(C)NC[C@H](O)c1ccc2ccc(C(F)(F)F)cc2n1] | |
| 03-202 | 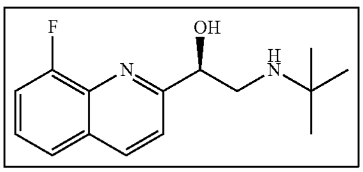 [SMILES: CC(C)(C)NC[C@H](O)c1ccc2cccc(F)c2n1] | |
| 03-203 | 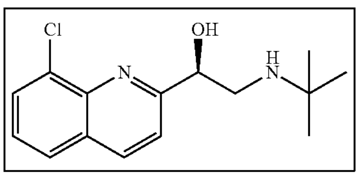 [SMILES: CC(C)(C)NC[C@H](O)c1ccc2cccc(Cl)c2n1] | |
| 03-204 | 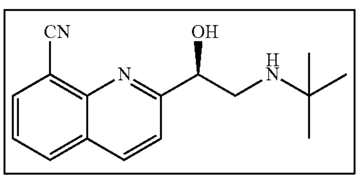 [SMILES: CC(C)(C)NC[C@H](O)c1ccc2cccc(C#N)c2n1] | |
| 03-205 | 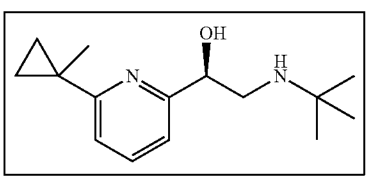 [SMILES: CC(C)(C)NC[C@H](O)c1cccc(C2(C)CC2)n1] | |
| 03-206 | 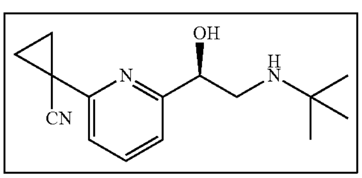 [SMILES: CC(C)(C)NC[C@H](O)c1cccc(C2(C#N)CC2)n1] | 260.4 |
| 03-207 | 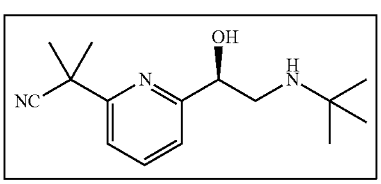 [SMILES: CC(C)(C)NC[C@H](O)c1cccc(C(C)(C)C#N)n1] | 262.3 |

TABLE 1-continued

The compound in the instant disclosure.

| Compound No. | Chemical Structure | MS (m/z) (M + 1) |
|---|---|---|
| 03-208 | 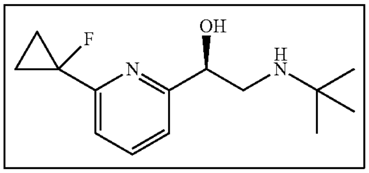 [SMILES: CC(C)(C)NC[C@H](O)c1cccc(C2(F)CC2)n1] | |
| 03-209 | 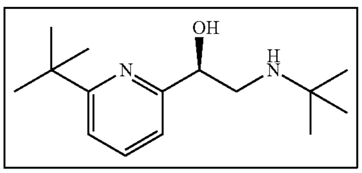 [SMILES: CC(C)(C)NC[C@H](O)c1cccc(C(C)(C)C)n1] | 251.2 |
| 03-210 | 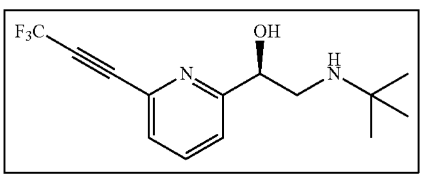 [SMILES: CC(C)(C)NC[C@H](O)c1cccc(C#CC(F)(F)F)n1] | |
| 03-211 | 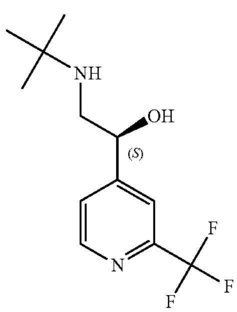 | 263.2 |
| 03-212 | 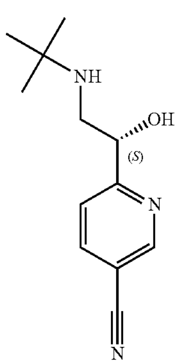 | 220.2 |

TABLE 1-continued
The compound in the instant disclosure.
| Compound No. | Chemical Structure | MS (m/z) (M + 1) |
|---|---|---|
| 03-213 | 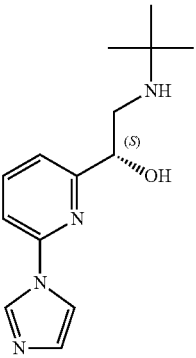 | 261.3 |
| 03-214 | 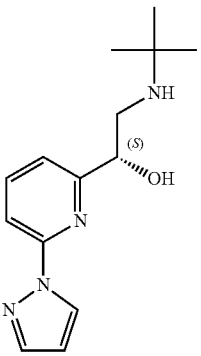 | 261.2 |
| 03-215 | 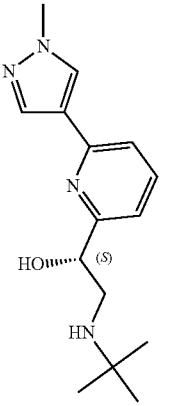 | 275.3 |
| 03-216 | 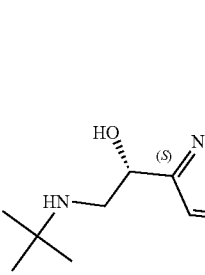 | 275.3 |

TABLE 1-continued

The compound in the instant disclosure.

| Compound No. | Chemical Structure | MS (m/z) (M + 1) |
|---|---|---|
| 03-217 | $F_5S$-pyridine-CH(OH)-CH$_2$-NH-tBu (6-SF$_5$ pyridin-2-yl) | |
| 03-218 | $F_3C$-pyridine-CH(OH)-CH$_2$-NH-C(cyclopropyl)(CF$_3$) | 315.2 |
| 03-219 | tBu-NH-CH$_2$-CH(OH)-(6-chloropyrazin-2-yl) | 230.4 |
| 03-220 | tBu-NH-CH$_2$-C(R)(H)(OH)-(6-(pyridin-4-yl)pyridin-2-yl) | 272.5 |
| 03-221 | tBu-NH-CH$_2$-C(S)(H)(OH)-(6-(pyridin-4-yl)pyridin-2-yl) | 272.5 |

TABLE 1-continued
The compound in the instant disclosure.
| Compound No. | Chemical Structure | MS (m/z) (M + 1) |
|---|---|---|
| 03-222 | 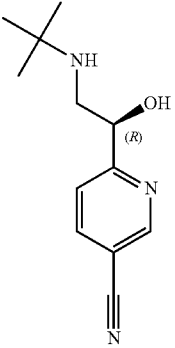 | 220:2 |
| 03-224 | 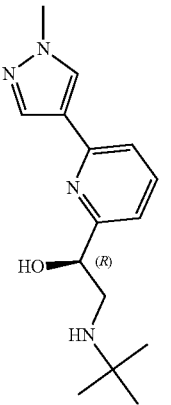 | 275.3 |
| 03-225 | 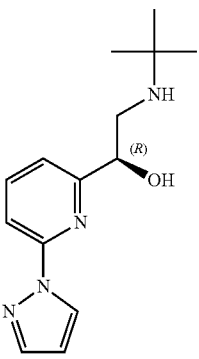 | 261.2 |
| 03-226 | 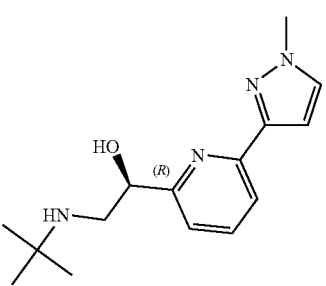 | 275.3 |

TABLE 1-continued

The compound in the instant disclosure.

| Compound No. | Chemical Structure | MS (m/z) (M + 1) |
|---|---|---|
| 03-227 | 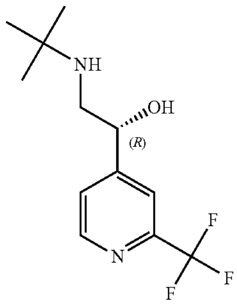 | 263.2 |
| 03-228 | 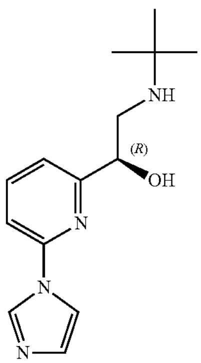 | 261.3 |
| 03-229 | 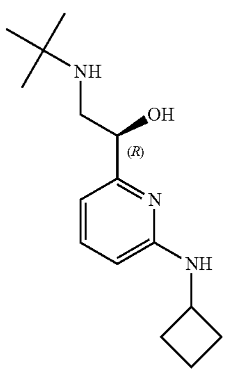 | 264.3 |
| 03-230 | 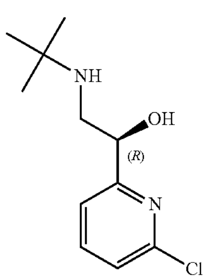 | 229.5 |

TABLE 1-continued

The compound in the instant disclosure.

| Compound No. | Chemical Structure | MS (m/z) (M + 1) |
|---|---|---|
| 03-231 | (S)-2-(tert-butylamino)-1-(6-chloropyridin-2-yl)ethan-1-ol | 229.5 |
| 03-232 | (R)-2-(tert-butylamino)-1-(6-(isopropylamino)pyridin-2-yl)ethan-1-ol | 252.3 |
| 03-233 | (R)-2-(tert-butylamino)-1-(6-(phenylamino)pyridin-2-yl)ethan-1-ol | 286.3 |
| 03-234 | (R)-2-(tert-butylamino)-1-(6-(cyclopent-1-en-1-yl)pyridin-2-yl)ethan-1-ol | 261.3 |

TABLE 1-continued

The compound in the instant disclosure.

| Compound No. | Chemical Structure | MS (m/z) (M + 1) |
|---|---|---|
| 03-235 | 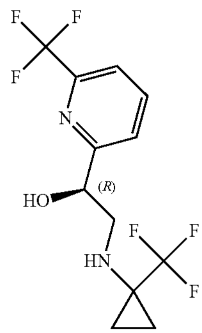 | 315.2 |
| 03-236 | 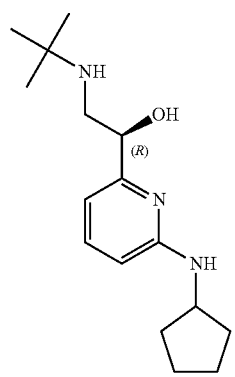 | 278.4 |
| 03-237 | 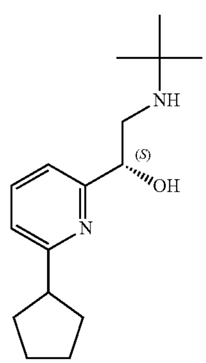 | 263.2 |
| 03-238 | 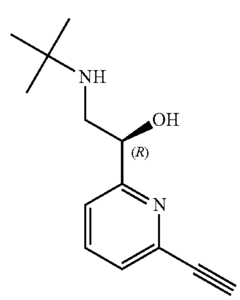 | 219.2 |

TABLE 1-continued

The compound in the instant disclosure.

| Compound No. | Chemical Structure | MS (m/z) (M + 1) |
|---|---|---|
| 03-239 | 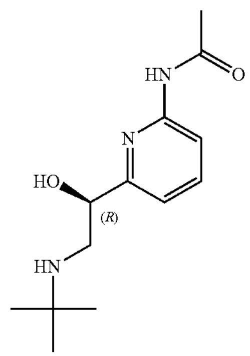 | 252.3 |
| 03-240 | 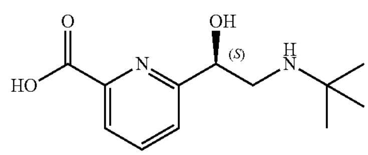 | 239.1 |
| 03-241 | 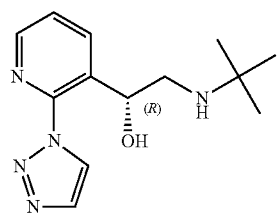 | 262.3 |
| 03-242 | 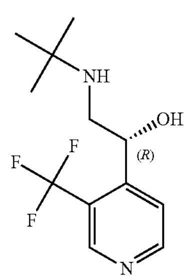 | 263.2 |
| 03-243 | 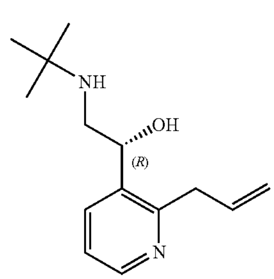 | 235.3 |

TABLE 1-continued

The compound in the instant disclosure.

| Compound No. | Chemical Structure | MS (m/z) (M + 1) |
|---|---|---|
| 03-244 | 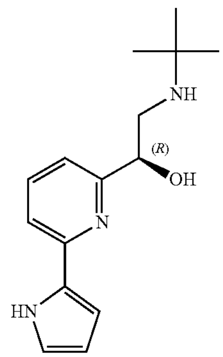 | 260.2 |
| 03-245 | 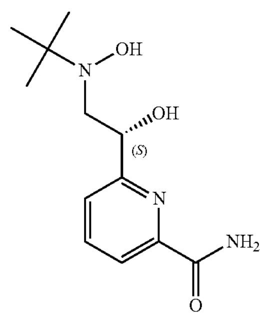 | 254.1 |
| 03-246 | 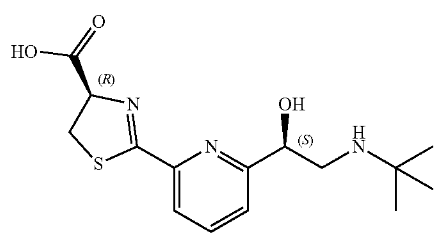 | 324.1 |
| 03-247 | 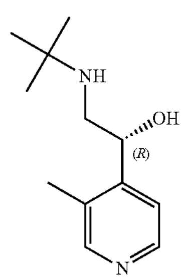 | 209.1 |
| 03-248 | 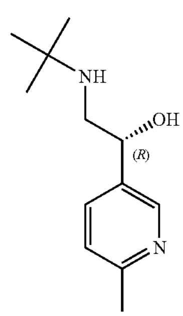 | 209.1 |

TABLE 1-continued

The compound in the instant disclosure.

| Compound No. | Chemical Structure | MS (m/z) (M + 1) |
|---|---|---|
| 03-249 | 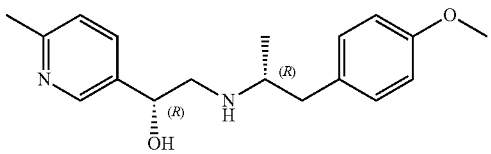 | 301.4 |
| 03-250 | 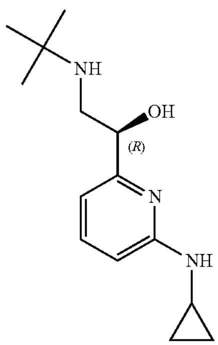 | 250.2 |
| 03-252 | 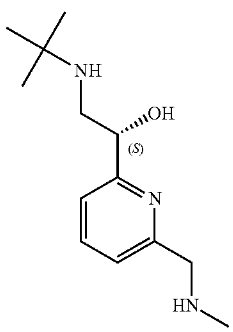 | 238.3 |
| 03-253 | 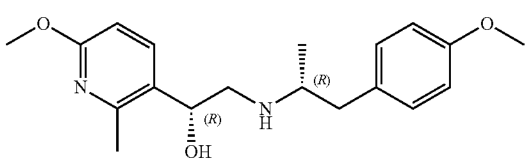 | 331.3 |
| 03-254 | 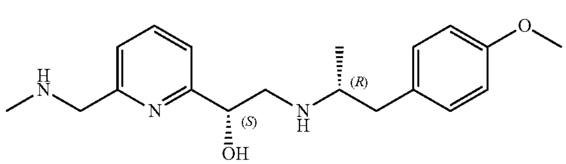 | 330.4 |
| 03-257 | 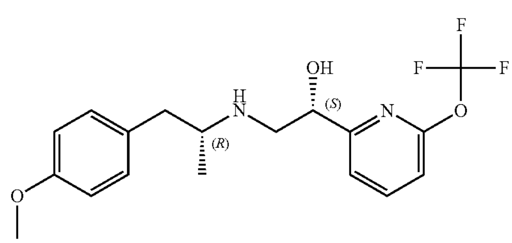 | 371.3 |

TABLE 1-continued

The compound in the instant disclosure.

| Compound No. | Chemical Structure | MS (m/z) (M + 1) |
|---|---|---|
| 03-258 | 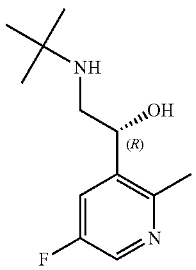 | 227.3 |
| 03-259 | 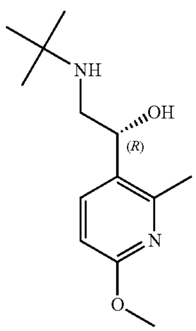 | 239.2 |
| 03-260 | 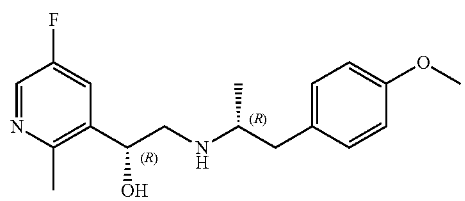 | 319.4 |
| 03-261 | 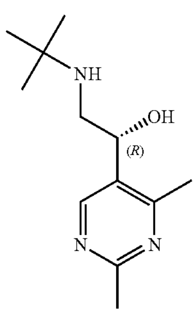 | 224.3 |
| 03-262 | 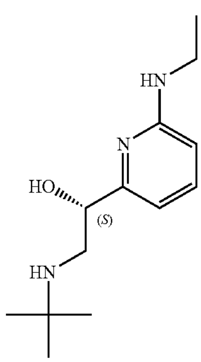 | 238.3 |

TABLE 1-continued

The compound in the instant disclosure.

| Compound No. | Chemical Structure | MS (m/z) (M + 1) |
|---|---|---|
| 03-263 | 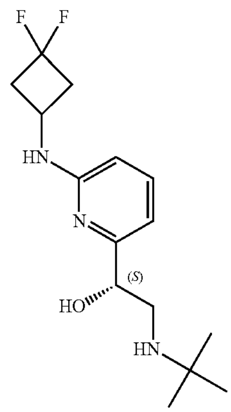 | 300.3 |
| 03-264 | 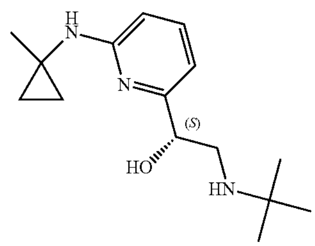 | 264.3 |
| 03-265 | 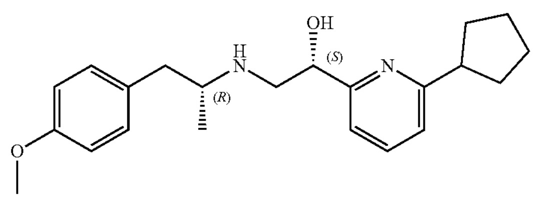 | 355.5 |
| 03-266 | 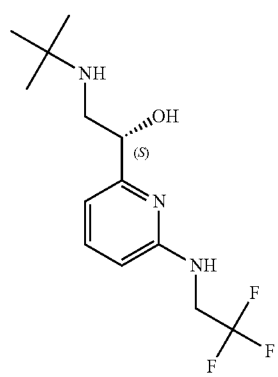 | 292.3 |
| 03-267 | 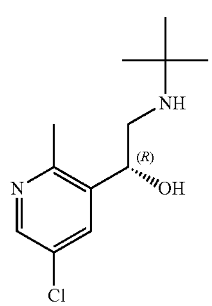 | 243.6 |

TABLE 1-continued

The compound in the instant disclosure.

| Compound No. | Chemical Structure | MS (m/z) (M + 1) |
|---|---|---|
| 03-268 | 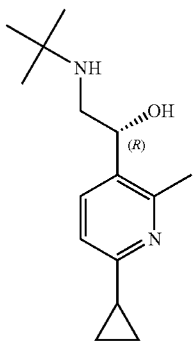 | 249.3 |
| 03-269 | 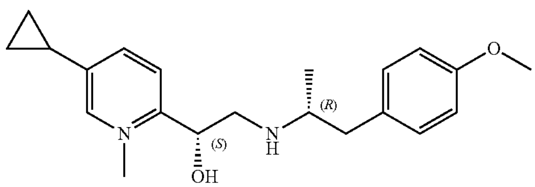 | 341.5 |
| 03-270 | 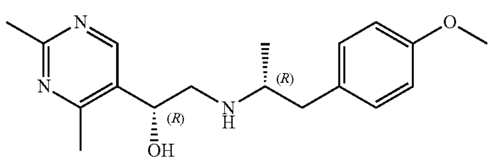 | 316.4 |
| 03-271 | 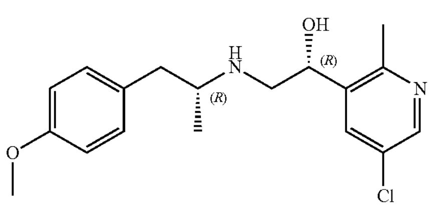 | 335.8 |
| 03-272 | 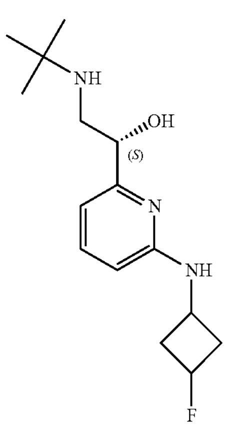 | 282.2 |

TABLE 1-continued

The compound in the instant disclosure.

| Compound No. | Chemical Structure | MS (m/z) (M + 1) |
|---|---|---|
| 03-273 | 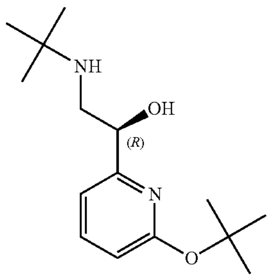 | 267.2 |
| 03-274 | 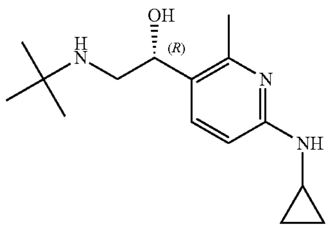 | 264.3 |
| 03-275 | 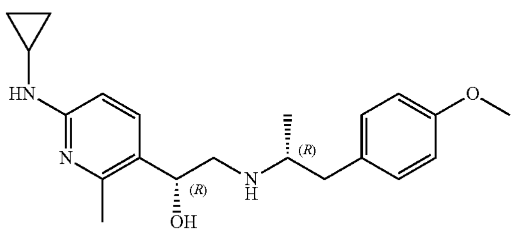 | 356.4 |
| 03-276 | 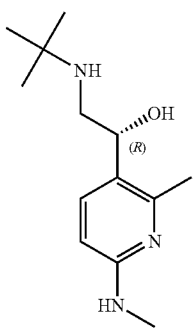 | 238.3 |
| 03-277 | 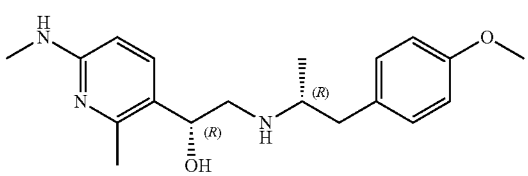 | 330.4 |
| 03-278 | 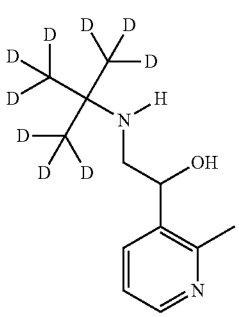 [SMILES: [2H]C([2H])([2H])C(NCC(O)c1cccnc1C)(C([2H])([2H])[2H])C([2H])([2H])[2H]] | 218.3 |

TABLE 1-continued

The compound in the instant disclosure.

| Compound No. | Chemical Structure | MS (m/z) (M + 1) |
|---|---|---|
| 03-279 | 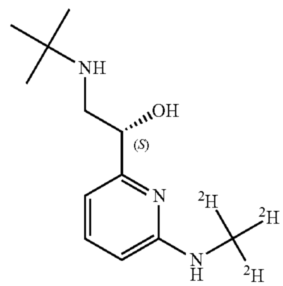 | 227.2 |
| 03-280 | 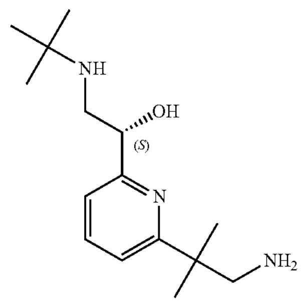 | 266.3 |
| 03-281 | 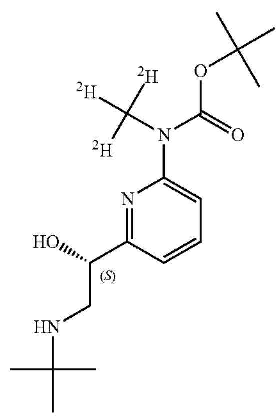 | 327.3 |

In some embodiments, the present disclosure provides a compound of Table 1, or pharmaceutically acceptable salt thereof.

Also disclosed herein is a pharmaceutical composition including a compound with a structure of Formula (I), Formula (II), Formula (III), Formula (I'), Formula (I''), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), or Formula (XXV'), and a pharmaceutically acceptable excipient. Further disclosed is a method of treating a subject with a disease associated with an adrenergic receptor, the method comprising administering to the subject a therapeutically effective amount of a compound with a structure of Formula (I), Formula (II), Formula (III), Formula (I'), Formula (I''), Formula (II'), Formula (III'), Formula (IV'), Formula (V'), Formula (VI'), Formula (VII'), Formula (VIII'), Formula (IX'), Formula (X'), Formula (XI'), Formula (XII'), Formula (XIII'), Formula (XIV'), Formula (XV'), Formula (XVI'), Formula (XVII'), Formula (XVIII'), Formula (XIX'), Formula (XX'), Formula (XXI'), Formula (XXII'), Formula (XXIII'), Formula (XXIV'), or Formula (XXV'), thereby treating the subject. In some embodiments, the disease is a neurodegenerative disease, the subject is a human.

In some embodiments, the disease is selected from the group consisting of myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies, and neuronal ceroid lipofuscinosis. In some embodiments, the compound is administered to the subject through oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route. In one embodiment, the compound is selected from those compounds set forth in Table 1.

The compounds of this invention may be prepared or isolated in general by synthetic and/or semi-synthetic methods known to those skilled in the art for analogous compounds and by methods described in detail in the Examples, herein. In one embodiment, the compounds selected from those compounds set forth in Table 1 were prepared by the methods illustrated in Scheme A.

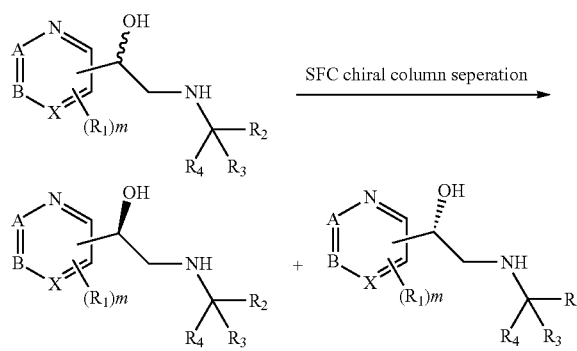

In one embodiment, the compounds selected from those compounds set forth in Table 1 were prepared by the methods illustrated in Scheme B.

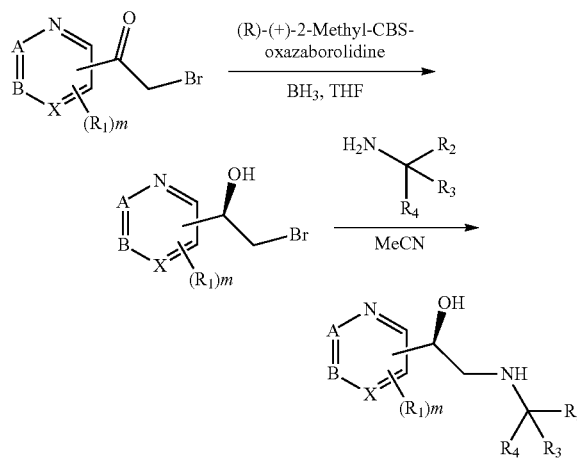

In one embodiment, the compounds selected from those compounds set forth in Table 1 were prepared by the methods illustrated in Scheme C.

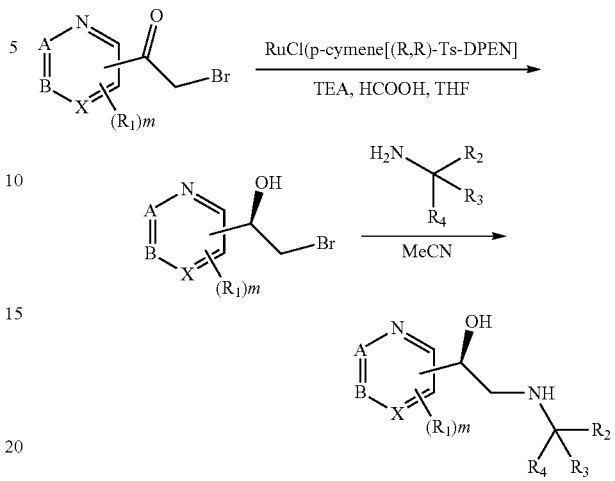

In one embodiment, the compounds selected from those compounds set forth in Table 1 were prepared by the methods illustrated in Scheme D.

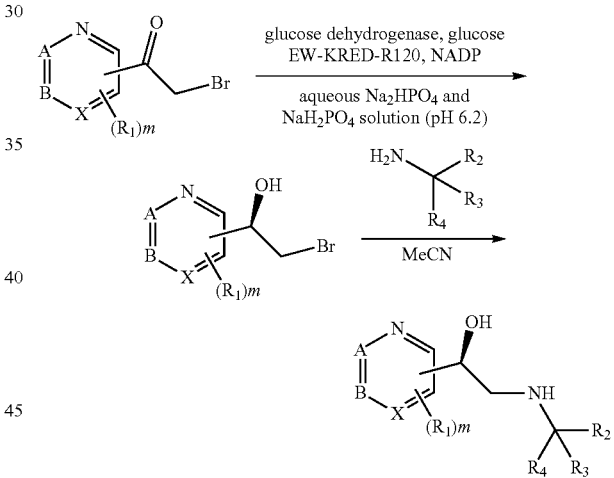

In one embodiment, the compounds selected from those compounds set forth in Table 1 were prepared by the methods illustrated in Scheme E.

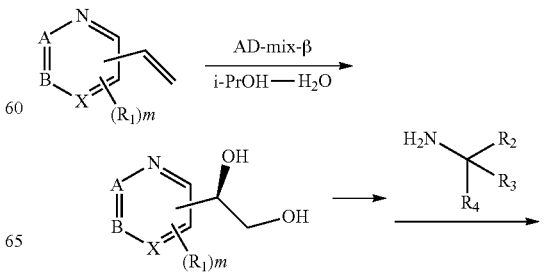

-continued

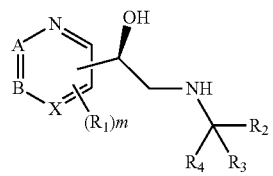

In one embodiment, the compounds selected from those compounds set forth in Table 1 were prepared by the methods illustrated in Scheme F.

Scheme F.

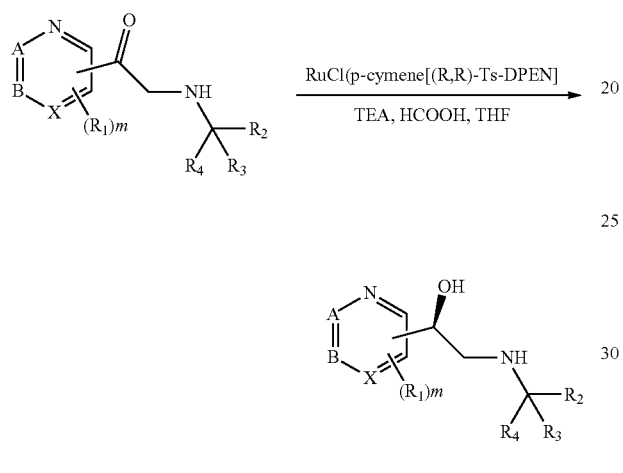

In one embodiment, the compounds selected from those compounds set forth in Table 1 were prepared by the methods illustrated in Scheme G.

Scheme G.

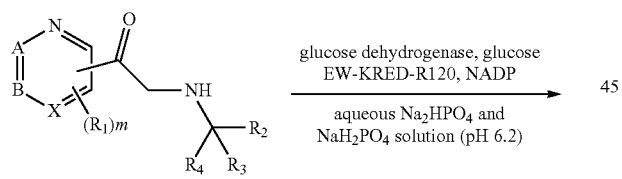

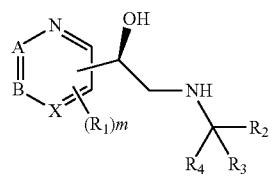

The following examples are provided to further illustrate the advantages and features of the present disclosure, but they are not intended to limit the scope of the disclosure. While the examples is typical of those that might be used, other procedures, methodologies, or techniques known to those skilled in the art may alternatively be used.

EXAMPLES

Example 1: Compound Synthesis

Scheme 1. Synthesis of Compound 03-1.

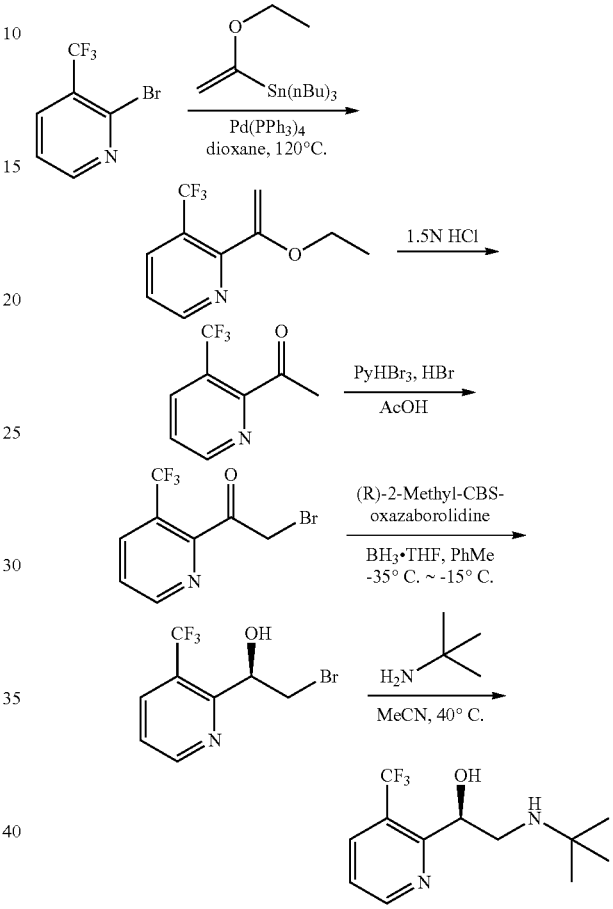

Scheme 1 illustrates the synthesis of compound 03-1.

Step 1: Synthesis of 1-(3-(trifluoromethyl)pyridin-2-yl)ethan-1-one

To a stirred solution of 2-bromo-3-(trifluoromethyl)pyridine (4.0 g, 17.7 mmol) and tributyl(1-ethoxyvinyl)tin (8.4 g, 23.0 mmol) in dioxane (50 mL) was added Pd(PPh$_3$)$_4$ (1.01 g, 0.88 mmol, 0.05 eq). The resulting mixture was purged with N2 (3×) before heating to 120° C. for 6 h. After cooling, aqueous 1.5N HCl was introduced to the flask and stirring was continued at RT overnight. The reaction mixture was quenched with aqueous saturated NaHCO$_3$ solution (30 mL) and then extracted with EtOAc (3×30 mL). The combined organic layers were washed with brine, dried over Na$_2$SO$_4$, filtered, and concentrated under reduced pressure. The residue was purified by flash chromatography eluting with Hexanes/EtOAc (silica, 30/1 to 5/1) to provide 1-(3-(trifluoromethyl)pyridin-2-yl)ethan-1-one as a yellow oil (2.4 g, 71%). MS (m/z): 190.1 (M+H)$^+$.

Step 2: Synthesis of 2-bromo-1-(3-(trifluoromethyl)pyridin-2-yl)ethan-1-one

To a stirred solution of 1-(3-(trifluoromethyl)pyridin-2-yl)ethan-1-one (0.5 g, 2.65 mmol) and HBr (40%, 0.5 mL) in AcOH (8 mL) was added pyridinium tribromide (0.85 g, 2.65 mmol). The resulting mixture was stirred at 40° C. overnight before cooling and quenching with aqueous saturated NaHCO$_3$ solution (100 mL). The reaction mixture was subsequently extracted with EtOAc (3×30 mL). The combined organic layers were washed with brine, dried over Na$_2$SO$_4$, filtered, and concentrated under reduced pressure. The residue was purified by flash chromatography eluting with Hexanes/EtOAc (silica, 30/1 to 3/1) to provide 2-bromo-1-(3-(trifluoromethyl)pyridin-2-yl)ethan-1-one as a yellow oil (0.37 g, 52%). MS (m/z): 267.9 (M+H)$^+$.

Step 3: Synthesis of (R)-2-bromo-1-(3-(trifluoromethyl)pyridin-2-yl)ethan-1-ol

To a stirred solution of 2-bromo-1-(3-(trifluoromethyl)pyridin-2-yl)ethan-1-one (0.37 g, 1.38 mmol) in toluene (4 mL) was added (R)-2-methyl-CBS-oxazaborolidine (0.3 mL, 1N in THF) at −35° C. The resulting mixture was stirred at −35° C. for 30 minutes. Borane-THF (2 mL, 1N in THF) was then added dropwise. The resulting solution was stirred at −15° C. for 2 hrs. and then quenched with aqueous saturated NaHCO$_3$ solution (10 mL) and extracted with EtOAc (3×10 mL). The combined organic layers were washed with brine, dried over Na$_2$SO$_4$, and concentrated under reduced pressure. The residue was purified by flash chromatography eluting with DCM/CH$_3$OH (silica, 50/1 to 15/1) to provide (R)-2-bromo-1-(3-(trifluoromethyl)pyridin-2-yl)ethan-1-ol as a yellow oil (0.12 g, 32%). MS (m/z): 269.9 (M+H)$^+$.

Step 4: Synthesis of (S)-2-(tert-butylamino)-1-(3-(trifluoromethyl)pyridin-2-yl)ethan-1-ol To a stirred solution of (R)-2-bromo-1-(3-(trifluoromethyl)pyridin-2-yl)ethan-1-ol (0.12 g, 0.44 mmol) in acetonitrile (3 mL) was added tert-butylamine (3 mL, 2.09 g, 28.6 mmol). The resulting mixture was stirred at 40° C. for 48 h and concentrated under reduced pressure. The residue was dissolved in EtOAc, washed with aqueous saturated NaHCO$_3$ solution and brine, dried over Na$_2$SO$_4$, and concentrated under reduced pressure. The residue was purified by HPLC [C18, MeCN/H$_2$O (0.1% formic acid), (1%~100%)] to provide compound 03-1 (S)-2-(tert-butylamino)-1-(3-(trifluoromethyl)pyridin-2-yl)ethan-1-ol as a white solid (0.045 g, 39%). $^1$H NMR (400 MHz, DMSO-d$_6$) δ 8.89 (dd, J=4.8, 1.5 Hz, 1H), 8.29 (s, 1H), 8.20 (dd, J=8.0, 1.6 Hz, 1H), 7.60 (ddd, J=8.0, 4.8, 0.9 Hz, 1H), 5.13-5.07 (m, 1H), 3.23-3.17 (m, 1H), 3.03 (dd, J=12.1, 3.6 Hz, 1H), 1.19 (s, 9H). MS (m/z): 263.2 (M+H)$^+$.

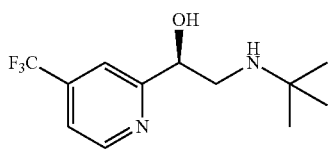

Compound 03-2. $^1$H NMR (400 MHz, DMSO-d$_6$) δ 8.82 (d, J=5.1 Hz, 1H), 8.31 (s, 1H), 7.84 (s, 1H), 7.69 (dd, J=5.1, 1.7 Hz, 1H), 4.87 (dd, J=8.8, 3.3 Hz, 1H), 3.13 (dd, J=11.9, 3.4 Hz, 1H), 2.85 (dd, J=11.9, 8.9 Hz, 1H), 1.14 (s, 9H).

Scheme 2. Synthesis of Compound 03-3.

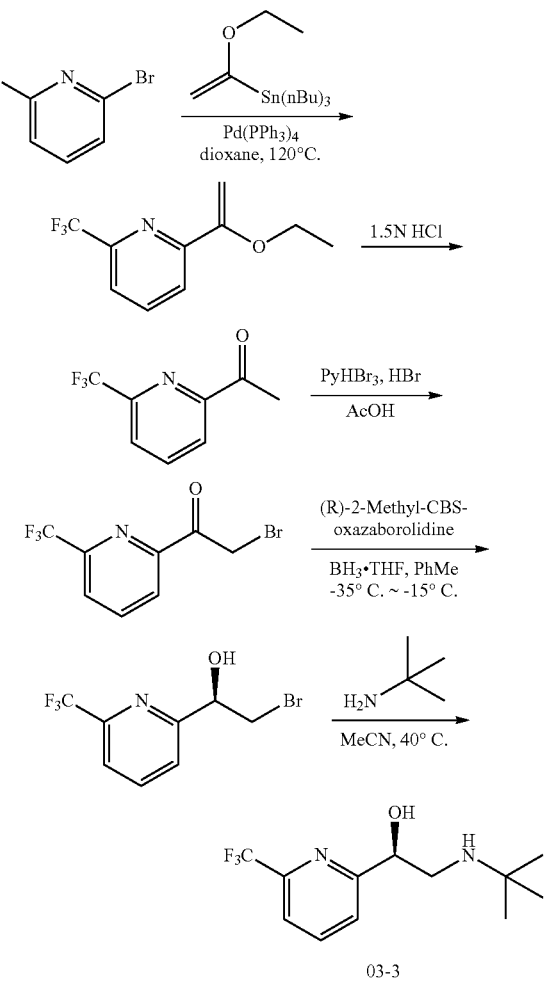

Scheme 2 illustrates the synthesis of compound 03-3. $^1$H NMR (400 MHz, DMSO-d$_6$) δ 8.29 (s, 1H), 8.13 (t, J=7.8 Hz, 1H), 7.88 (d, J=7.9 Hz, 1H), 7.82 (dd, J=7.8, 0.9 Hz, 1H), 4.84 (dd, J=8.7, 3.5 Hz, 1H), 3.08 (dd, J=11.9, 3.6 Hz, 1H), 2.89 (dd, J=11.9, 8.7 Hz, 1H), 1.15 (s, 9H).

Scheme 3. Synthesis of compound 03-4.

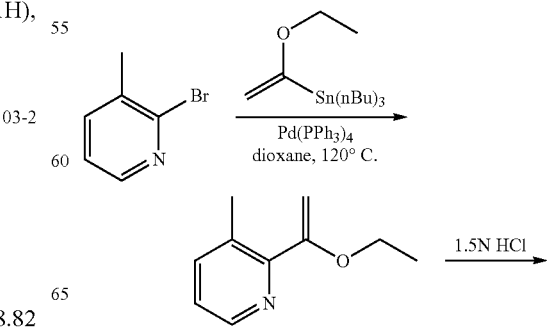

173

-continued

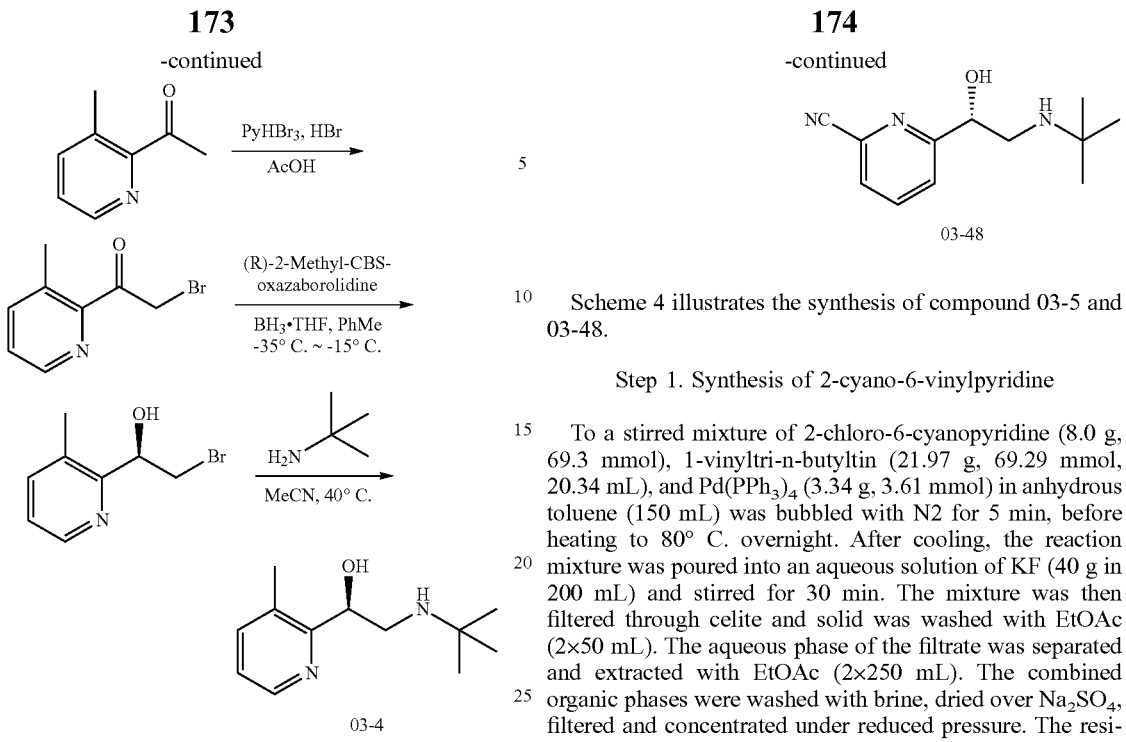

Scheme 3 illustrates the synthesis of compound 03-4. $^1$H NMR (400 MHz, DMSO-$d_6$) δ 8.42 (dd, J=4.8, 1.7 Hz, 1H), 7.67 (ddd, J=7.6, 1.8, 0.8 Hz, 1H), 7.31 (dd, J=7.7, 4.7 Hz, 1H), 5.92 (s, 1H), 5.06 (dd, J=8.5, 3.8 Hz, 1H), 3.26-3.18 (m, 2H), 2.41 (s, 3H), 1.30 (s, 9H).

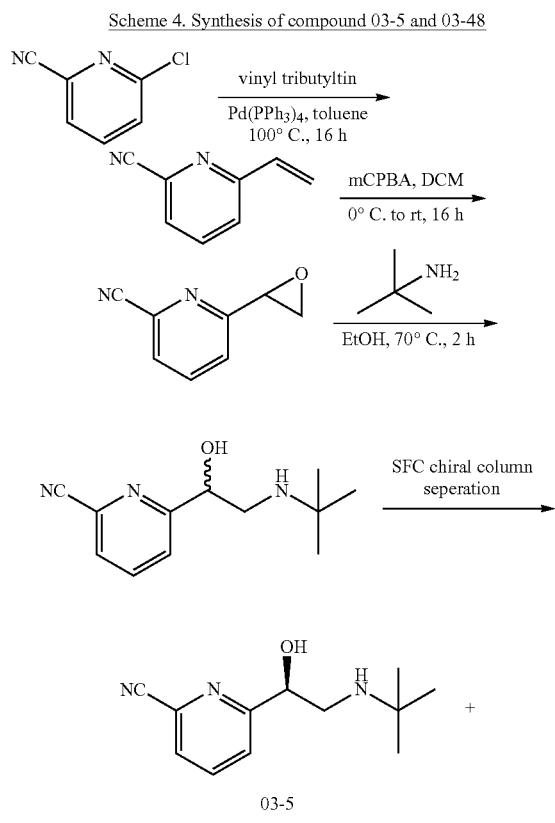

174

-continued

Scheme 4 illustrates the synthesis of compound 03-5 and 03-48.

Step 1. Synthesis of 2-cyano-6-vinylpyridine

To a stirred mixture of 2-chloro-6-cyanopyridine (8.0 g, 69.3 mmol), 1-vinyltri-n-butyltin (21.97 g, 69.29 mmol, 20.34 mL), and Pd(PPh$_3$)$_4$ (3.34 g, 3.61 mmol) in anhydrous toluene (150 mL) was bubbled with N2 for 5 min, before heating to 80° C. overnight. After cooling, the reaction mixture was poured into an aqueous solution of KF (40 g in 200 mL) and stirred for 30 min. The mixture was then filtered through celite and solid was washed with EtOAc (2×50 mL). The aqueous phase of the filtrate was separated and extracted with EtOAc (2×250 mL). The combined organic phases were washed with brine, dried over Na$_2$SO$_4$, filtered and concentrated under reduced pressure. The residue was purified by flash chromatography eluting with Hexanes/EtOAc (silica, 95/5 to 90/10) to provide 2-cyano-6-vinylpyridine as a pale yellow liquid (6.5 g, 86%). MS (m/z): 131.1 (M+H)$^+$.

Step 2: Synthesis of 6-(oxiran-2-yl)picolinonitrile

To a stirred solution of 2-cyano-6-vinylpyridine (6.5 g, 49.94 mmol) in DCM (300 mL) was added mCPBA (61.56 g, 249.72 mmol) at 0° C. slowly portion wise over a period of 30 min and stirred at RT for 24 h. After completion of reaction, reaction mixture was cooled to 5° C. and added aqueous saturated NaHCO$_3$ solution and extracted with DCM (200 mL×2). Organic layers were combined, dried over Na$_2$SO$_4$, filtered, and concentrated under reduced pressure. The residue was purified by flash chromatography eluting with Hexanes/EtOAc (silica, 90/10 to 80/20) to provide 6-(oxiran-2-yl)picolinonitrile as a colorless liquid (3.85 g, 52%). MS (m/z): 147.1 (M+H)$^+$.

Step 3: Synthesis of (S)-6-(2-(tert-butylamino)-1-hydroxyethyl)picolinonitrile and (R)-6-(2-(tert-butylamino)-1-hydroxyethyl)picolinonitrile To a stirred solution of 6-(oxiran-2-yl) picolinonitrile (3.5 g, 18.2 mmol) in ethanol (25 mL) was added tert-butylamine (6.66 g, 91.0 mmol). The reaction mixture was stirred at 80° C. for 3 h in a sealed tube, while monitoring reaction by TLC and LCMS. After completion of reaction, solvent was evaporated to get a residue, which was purified by reverse phase chromatography to provide desired products as a racemic mixture. A racemic mixture was separated by SFC (Chiralpak AS-H (30*250) mm, 5µ column, using CO$_2$: 80% Co-solvent: 20% (0.2% isopropylamine in IPA as eluent) to provide compound 03-5 (S)-6-(2-(tert-butylamino)-1-hydroxyethyl)picolinonitrile (1.05 g, 26.3%) and compound 03-48 (R)-6-(2-(tert-butylamino)-1-hydroxyethyl)picolinonitrile (0.98 g, 24.5%) as white solids. Compound 03-5: $^1$HNMR 400 MHz, DMSO-d6: δ 8.03 (t, J=8.00 Hz, 1H), 7.90 (dd, J=0.80 Hz, 7.60 Hz, 1H), 7.82 (d, J=8.00 Hz, 1H), 5.63 (s, 1H), 4.60 (q, J=4.40 Hz, 1H), 2.86-2.80 (m, 1H), 2.67-2.49 (m, 1H), 1.44-1.40 (m, 1H), 0.98 (s, 9H). Compound 03-48: $^1$HNMR 400 MHz, DMSO-d6: δ 8.03 (t, J=7.60 Hz, 1H), 7.90 (d, J=6.80 Hz, 1H), 7.82 (d, J=8.00 Hz, 1H), 5.62 (s, 1H), 4.60 (s, 1H), 2.81-2.82 (m, 1H), 2.62-2.64 (m, 1H), 1.44 (s, 1H), 0.98 (s, 9H)

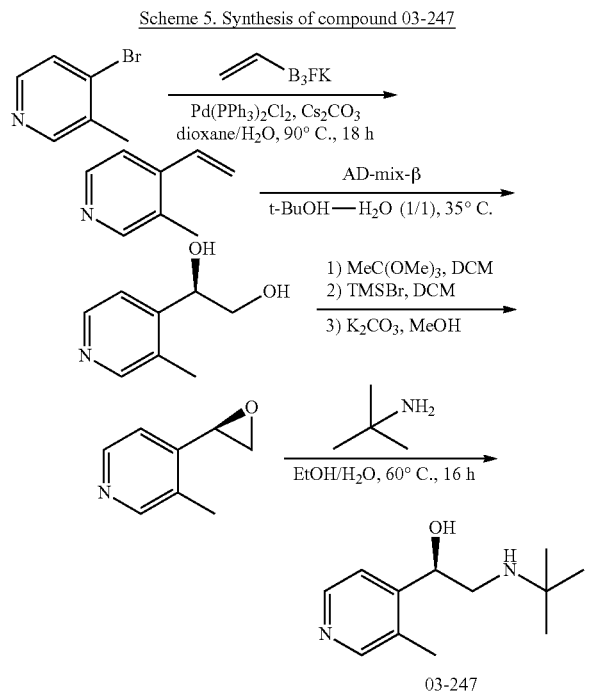

Scheme 5 illustrates the synthesis of compound 03-247.

Step 1: Synthesis of 3-methyl-4-vinylpyridine

To a solution of 4-bromo-3-methylpyridine (1.0 g, 4.80 mmol) in dioxane/H$_2$O (15 mL/1.5 mL) was added Cs$_2$CO$_3$ (4.69 g, 14.39 mmol), potassium vinyltrifluoroborate (0.96 g, 7.19 mmol) and Pd(PPh$_3$)$_2$Cl$_2$ (0.20 g, 0.27 mmol). The mixture was stirred at 85° C. for 15 h under N2 atmosphere. The resulting mixture was then filtered and washed with EtOAc (2×20 mL). The filtrate was dried over Na$_2$SO$_4$, filtered, concentrated under reduced pressure. The residue was purified by column chromatography eluting with Hexanes/EtOAc (silica, 90/10 to 75/25) to provide 3-methyl-4-vinylpyridine as yellow oil (0.45 g, 79%). MS (m/z): 120 (M+H)$^+$.

Step 2: Synthesis of (R)-1-(3-methylpyridin-4-yl)ethane-1,2-diol

To a solution of (R)-1-(3-methylpyridin-4-yl)ethane-1,2-diol (0.125 g, 0.82 mmol) in CH$_2$C12 (4 mL) was added MeC(OCH$_3$)$_3$ (0.30 g, 2.46 mmol) and p-toluenesulfonic acid (0.008 g, 0.048 mmol) and stirred at RT for 6 h. The mixture was then concentrated in vacuo. The residue was re-dissolved in anhydrous CH$_2$Cl$_2$ (4 mL) followed by adding TMSBr (0.26 g, 1.71 mmol) dropwise at 0° C. The resulting mixture was stirred at RT for 15 h. The reaction mixture was concentrated under reduced pressure. To the residue in anhydrous CH$_3$OH (4 mL) was added K$_2$CO$_3$ (0.33 g, 2.40 mmol) and the reaction mixture was stirred at 30° C. for 4 h. The reaction mixture was filtered. The filtrate was concentrated under reduced pressure to provide crude (R)-3-methyl-4-(oxiran-2-yl)pyridine as an oil (0.08 g, 72%). MS (m/z): 136 (M+H)$^+$.

Step 4: Synthesis of (R)-2-(tert-butylamino)-1-(3-methylpyridin-4-yl)ethan-1-ol

To a solution of (R)-3-methyl-4-(oxiran-2-yl)pyridine (0.08 g, 0.60 mmol) in EtOH/H$_2$O (2 mL/1 mL) was added tert-BuNH$_2$ (0.24 g, 3.30 mmol). The resulting mixture was stirred at 60° C. for 15 h and concentrated under reduced pressure. The residue was purified by HPLC [C18, MeCN/H$_2$O (0.1% trifluoroacetic acid), (1%~100%)] to provide compound 03-247 (R)-2-(tert-butylamino)-1-(3-methylpyridin-4-yl)ethan-1-ol which was then converted to 2HCl salt as a white solid (0.044 g, 26%). $^1$H NMR (400 MHz, CD$_3$OD) δ 8.77 (d, J=6.0 Hz, 1H), 8.74 (s, 1H), 8.29 (d, J=6.0 Hz, 1H), 5.38 (d, J=8.6 Hz, 1H), 3.27-3.26 (m, 1H), 3.09-3.01 (m, 1H), 2.59 (s, 3H), 1.41 (s, 9H).

One of skill in the art will appreciate that the above synthetic schemes are representative of methods of making compounds of the present disclosure and that numerous other compounds can be synthesized using similar such methods.

Example 2: Evaluation of Synthesized Adrenergic Receptor Agonists cAMP homogeneous time-resolved fluorescence (HTRF). Compound efficacy was determined using the cAMP Gs dynamic HTRF assay (Cisbio, catalog #62AM4PEC) largely following the manufacturer's instructions, also detailed below.

Compound preparation. Candidate beta-adrenergic compounds, dissolved to 10 mM in DMSO, were diluted in 1× stimulation buffer 1 (Cisbio Part #64SB1FDD) containing 1 mM 3-Isobutyl-1-methylxanthene (IBMX; Cayman Chemical Company, catalog #13347). Serial dilutions were made in a 96 well V-bottom polypropylene compound microplate (Corning, catalog #3363) in stimulation buffer containing 1 mM IBMX, to 2× of the final desired concentration. Standard serial dilution curves were 10-point, 5-fold dilutions starting from a highest concentration of 10 μM. Controls present on every assay plate were 0.1% DMSO (vehicle control), 1 μM isoproterenol (full beta-adrenergic agonist control) and 15 μM xamoterol (partial beta-adrenergic agonist control). 5 μL from the 2× compound plate was stamped into a white 384 round well small volume HiBase assay plate (Greiner Bio-One; catalog #784075) to provide 4 technical replicates per concentration, per compound. Assay plates were centrifuged at 500×g for 10 seconds. Compounds and IBMX were prepared at 2× final dose to compensate for addition of cells.

Cell preparation. 1× stimulation buffer, washing PBS (Dulbecco's phosphate-buffered saline, –Mg –Ca; Caisson Labs, catalog #PBL01), assay PBS (Dulbecco's phosphate-buffered saline, +Mg, +Ca; Caisson Labs, catalog #PBL02) and Versene (0.02% EDTA disodium salt solution in PBS without calcium or magnesium; Caisson Labs, catalog #EDL01) were pre-warmed to 37° C. Cells expressing beta-adrenergic receptor were washed in washing PBS to remove growth medium and then released from the surface by incubating with Versene for 5-10 minutes at 37° C. Cells were harvested using assay PBS, counted manually by hemocytometer or by an automated cell counter, pelleted by centrifugation (200×g, 5 minutes) and resuspended in 37° C. 1× stimulation buffer to a final density of 1.5×10$^6$ cells/mL.

5 μL of the suspended cell solution (7500 cell total) were added to all wells of the 384 well assay plate, the assay plate was covered with an Axygen® plate seal (Corning PCR-SP) and incubated in a humidified 37° C. environment supplemented with 5% $CO_2$ for 30 minutes.

HTRF reagent addition, reading and data analysis. After 30 minutes of cell stimulation with test compound, the assay plates were centrifuged at 500×g for 10 seconds, and incubation was stopped with the addition of 5 μL cAMP-D2 acceptor, diluted 1:21 in detection and lysis buffer 2 (Cisbio 62CL2FDF) was added to all cells. Subsequently, 5 μL Anti-cAMP-Eu Donor, diluted 1:21 in detection and lysis buffer 2, was added to cells. Plates were sealed and reactions gently 'vortexed' at 900 rpm on a Heidolph Titramax 1000 for at least 30 minutes at room temperature. Plates were centrifuged again at 500×g for 10 seconds, and HTRF was measured using a Tecan Spark plate reader at 50 flashes per well. HTRF ratios (665 nm/620 nm×10,000) were determined and plotted in GraphPad Prism to generate a concentration-effect curve. Potency estimates ($EC_{50}$) were derived from the four-parameter nonlinear regression of the concentration-effect curve and an estimate of relative efficacy was determined by comparing the magnitude of the test compound HTRF signal window (min–max dose) with the signal window of the full agonist control, isoproterenol.

The potency data for select compounds is summarized in Table 2, below.

TABLE 2

The pharmacological data of the chemical compounds disclosed herein.

| Compound | β1 $EC_{50}$ (nM) | β2 $EC_{50}$ (nM) |
| --- | --- | --- |
| 03-1 | D | D |
| 03-2 | D | C |
| 03-3 | B | A |
| 03-4 | D | D |

$EC_{50}$ (nM): A < 10 nM; B = 10-100 nM; C = 100 nM-1 μM; D > 1 μM

Figure 2:
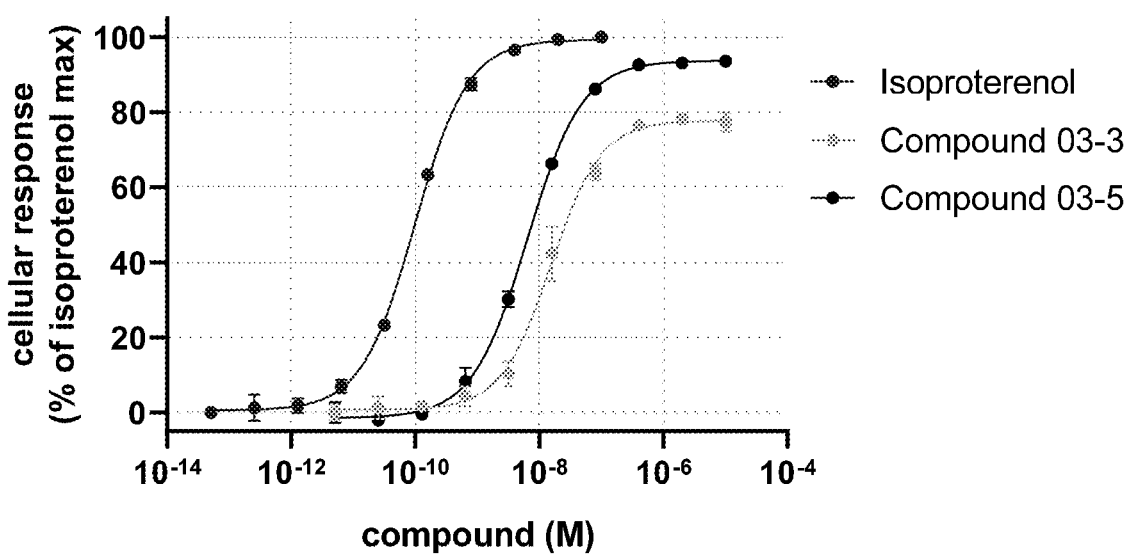
FIG. 2 summarizes the concentration dependent inhibition of Compounds 03-3 and 03-5 in β2 expressing CHO cells with isoproterenol as control.
Figure 3:
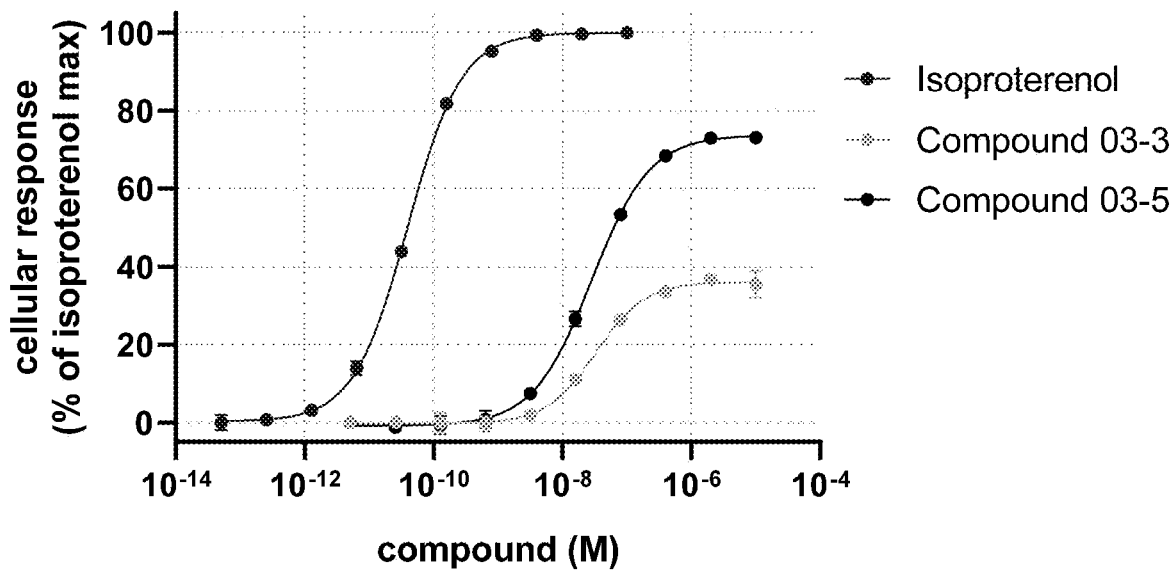
FIG. 3 summarizes the concentration dependent inhibition of Compounds 03-3 and 03-5 in human astrocytoma cells (1321N1) with isoproterenol as control.

It has been surprisingly found that certain compounds of the present disclosure are partial agonists of β2 adrenergic receptors, particularly in human astrocytoma cells (e.g., 1321N1). The inhibition curves for select compounds are further summarized in FIG. 1, FIG. 2, and FIG. 3. Potency data for further compounds of the invention is found in Example 8.

Example 3: In Vitro Absorption, Distribution, Metabolism, Excretion and Toxicity (ADMET) Studies As described above and herein, compounds of the present disclosure exhibit unexpectedly good properties. For instance, as described above, it was surprisingly found that compounds of the present disclosure act as low nM (<10 nM) partial agonists of the (32 adrenergic receptor. Furthermore, and as the following examples demonstrate, compounds of the present disclosure exhibit an unexpectedly high ability to cross the blood brain barrier and accumulate in the cerebral spinal fluid. Additionally, compounds of the present disclosure exhibit excellent oral bioavailability and stability, while simultaneously exhibiting low toxicity and a low potential for drug-drug interactions. The following examples are illustrative of certain of the unexpected results achieved with compounds of the present disclosure.

Plasma Protein and Brain Tissue Binding
Brain Tissue Binding Measurements

Thawing of the frozen brain tissue homogenate (stored at −80° C.). Frozen brain tissue homogenate was thawed immediately in a room temperature bath. Note: Only use brain tissue homogenate that has been thawed no more than once.

Preparation of working solutions. The working solutions of test compound and control compound propranolol were prepared in DMSO at the concentration of 200 μM. And then 4 μL of working solution was removed to mix with 796 μL of rat brain tissue homogenate to achieve a final concentration of 1 μM (0.5% DMSO). Brain tissue homogenate samples were vortexed thoroughly.

Preparation of dialysis membranes. The dialysis membranes were soaked in ultrapure water for 60 minutes to separate strips, then in 20% ethanol for 20 minutes, finally in dialysis buffer for 20 minutes.

Procedure for equilibrium dialysis. The dialysis apparatus was assembled according to the manufacturer's instruction. Each cell was filled with 150 μL of brain tissue homogenate sample and dialyzed against equal volume of dialysis buffer (PBS). The assay was performed in duplicate. The dialysis plate was sealed and incubated in an incubator at 37° C. with 5% $CO_2$ at approximately 100 rpm for 6 hours. At the end of dialysis, seal was removed and 50 μL of samples from both buffer and brain tissue homogenate chambers were transferred into separate tubes in plate.

Procedure for sample analysis. 50 μL of brain tissue homogenate was added to each buffer samples and an equal volume of PBS was supplemented to the collected brain tissue homogenate sample. 400 μL of room temperature quench solution (acetonitrile containing internal standards (IS, 100 nM Alprazolam, 500 nM Labetalol and 2 μM Ketoprofen)) was added to precipitate protein. Samples in plate were vortexed for 5 minutes and centrifuged at 3,220 g for 30 minutes at room temperature. And then 100 μL of the supernatant was transferred to a new 96-well plate with 100 μL water for LC-MS/MS analysis.

Data analysis. All calculations were carried out using Microsoft Excel. Determine the concentrations of test compound and control compound in the buffer and brain tissue homogenate chambers from peak area ratios. Calculate the percentages of test compound and control compound bound as follows:

$$Fu_{means} = (\text{Peak Area Ratio}_{buffer\ chamber}/\text{Peak Area Ratio}_{brain\ tissue\ homogenate\ chamber}) + 1/D$$

$$\text{Undiluted } fu = ((1/Fu_{means}) - 1) + 1/D$$

$$\% \text{ Bound} = (1 - \text{Undiluted } fu) * 100\%$$

$$\text{Recovery} = (\text{Peak Area Ratio}_{buffer\ chamber} + \text{Peak Area Ratio}_{brain\ tissue\ homogenate\ chamber})/\text{Peak Area Ratio}_{total\ sample} * 100$$

$Fu_{means}$=unbound fraction measured with brain tissue homogenate

D=the dilution factor of brain tissue

% Bound=Brain tissue binding %

Plasma Protein Binding Measurements

Preparation of 100 mM sodium phosphate and 150 mM NaCl buffer (PBS). A basic solution was prepared by dissolving 14.2 g/L $Na_2HPO_4$ and 8.77 g/L NaCl in deionized water and the solution could be stored at 4° C. for up to 7 days. An acidic solution was prepared by dissolving 12.0 g/L $NaH_2PO_4$ and 8.77 g/L NaCl in deionized water and the solution could be stored at 4° C. for up to 7 days. The basic solution was titrated with the acidic solution to pH 7.4 and store at 4° C. for up to 7 days. pH was checked on the day of experiment and was adjusted if outside specification of 7.4±0.1.

Thawing of the frozen plasma (stored at −80° C.). Frozen plasma was thawed immediately at room temperature. The plasma was centrifuged at 3,220 g for 10 minutes to remove clots and supernatant was collected into a fresh tube. The pH of the plasma was checked and recorded. Note: a). Only use plasma that has been thawed no more than twice since arrival. b). Only use plasma within the range of pH 7 to pH 8.

Preparation of working solutions. The working solutions of test compound and control compound ketoconazole were prepared in DMSO at the concentration of 200 µM. And then 3 µL of working solutions was removed to mix with 597 µL of rat plasma to achieve a final concentration of 1 µM (0.5% DMSO). Plasma samples were vortexed thoroughly.

Preparation of dialysis membranes. The dialysis membranes were soaked in ultrapure water for 60 minutes to separate strips, then in 20% ethanol for 20 minutes, finally in dialysis buffer for 20 minutes.

Procedure for equilibrium dialysis. The dialysis apparatus was assembled according to the manufacturer's instruction. Each Cell was filled with 120 µL of spiked plasma sample and dialyzed against equal volume of dialysis buffer (PBS). The assay was performed in duplicate. The dialysis plate was sealed and incubated in an incubator at 37° C. with 5% $CO_2$ at 100 rpm for 6 hours. At the end of incubation, seal was removed and 50 µL of samples from both buffer and plasma chambers were transferred to wells of a 96-well plate.

Procedure for sample preparation. 50 µL of blank plasma was added to each buffer samples and an equal volume of PBS was supplemented to the collected plasma sample. 300 µL of room temperature quench solution (acetonitrile containing internal standards (IS, 100 nM Alprazolam, 500 nM Labetalol and 2 µM Ketoprofen)) was added to precipitate protein. Samples in plate were vortexed for 5 minutes and centrifuged at 3,220 g for 30 minutes at 4° C. And then 100 µL of the supernatant was transferred to a new 96-well plate with 100 µL water for LC-MS/MS analysis.

Data analysis. All calculations were carried out using Microsoft Excel. Determine the concentrations of test compound and control compound in the buffer and plasma chambers from peak area ratios. Calculate the percentages of test compound and control compound bound as follows:

% $Fu$=(Peak Area Ratio$_{buffer\ chamber}$/Peak Area Ratio$_{plasma\ chamber}$)*100

Bound=100−% $Fu$

% Recovery=(Peak Area Ratio$_{buffer\ chamber}$+Peak Area Ratio$_{plasma\ chamber}$)/Peak Area Ratio$_{total\ sample}$*100

Peak Area Ratio$_{buffer\ chamber}$ means the conc. for free fraction; Peak Area Ratio$_{plasma\ chamber}$ means the conc for both free and bound fraction; Peak Area Ratio total sample means the conc for starting sample before incubation Percent plasma protein binding (PPB) and brain tissue binding (BTB) for select compounds are summarized in Table 3, below.

It has been found that certain compounds of the present disclosure exhibit a high propensity to bind to and accumulate in the central nervous system.

TABLE 3

Percent of Unbound Fractions of PPB and Brain Tissue binding.

| Compound | PPB (rat) | PPB (human) | BTB (rat) |
|---|---|---|---|
| 03-3 | 90% | 89 | 48% |
| 03-5 | 100% | 100% | 95% |
| 03-115 | 97% | 100% | 100% |

MDCK-MDR1 Permeability Assay

Preparation of MDCK-MDR1 Cells. Cell culture medium of was added to each well of the Transwell insert (50 µL) and reservoir (25 mL). The HTS transwell plates were then incubated at 37° C., 5% $CO_2$ for 1 hour before cell seeding. MDCK-MDR1 cells were diluted to 1.56×10$^6$ cells/mL with culture medium and 50 µL of cell suspension were dispensed into the filter well of the 96-well HTS Transwell plate. Cells were cultivated for 4-8 days in a cell culture incubator at 37° C., 5% $CO_2$, 95% relative humidity. Cell culture medium was replaced every other day, beginning no later than 24 hours after initial plating.

Preparation of Stock Solutions. 10 mM stock solutions of test compounds were prepared in DMSO. The stock solutions of positive controls were prepared in DMSO at the concentration of 10 mM. Metoprolol, prazosin and imatinib were used as control compounds in this assay.

Assessment of Cell Monolayer Integrity. Medium was removed from the reservoir and each Transwell insert and replaced with prewarmed fresh culture medium. Transepithelial electrical resistance (TEER) across the monolayer was measured using Millicell Epithelial Volt-Ohm measuring system (Millipore, USA). The Plate was returned to the incubator once the measurement was done. TEER value should be greater than 42 ohm·cm2, which indicates the well-qualified MDCK-MDR1 monolayer. The TEER value was calculated according to the following equation:

TEER measurement (ohms)×Area of membrane ($cm^2$)=TEER value(ohm·$cm^2$)

Assay Procedures. The MDCK-MDR1 plate was removed from the incubator and washed twice with pre-warmed HBSS (10 mM HEPES, pH 7.4), and then incubated at 37° C. for 30 minutes. The stock solutions of test compounds and controls were diluted in DMSO to get 1 mM solutions and then diluted with HBSS (10 mM HEPES, pH 7.4) to get 5 µM working solutions. The final concentration of DMSO in the incubation system was 0.5%.

To determine the rate of drug transport in the apical to basolateral direction, 125 µL of 5 µM working solution of test compound and control compound were added to the Transwell insert (apical compartment), and transfer 50 µL sample (DO sample) immediately from the apical compartment to a new 96-well plate. The wells in the receiver plate (basolateral compartment) were filled with 235 µL of HBSS (10 mM HEPES, pH 7.4). The assay was performed in duplicate.

To determine the rate of drug transport in the basolateral to apical direction, 285 µL of 5 µM working solution of test compound and control compound were to the receiver plate wells (basolateral compartment), and transfer 50 µL sample (DO sample) immediately from the basolateral compartment to a new 96-well plate. The wells in the Transwell insert (apical compartment) were filled with 75 µL of HBSS (10 mM HEPES, pH 7.4). The plates were incubated at 37° C. for 2 hours. At the end of the incubation, 50 µL samples from donor sides (apical compartment for Ap→Bl flux, and basolateral compartment for Bl→Ap) and receiver sides (basolateral compartment for Ap→Bl flux, and apical compartment for Bl→Ap) were transferred to wells of a new 96-well plate, followed by the addition of 4 volume of cold methanol containing appropriate internal standards (IS). Samples were Vortexed for 5 minutes and then centrifuged at 3,220 g for 40 minutes. An aliquot of 100 µL of the supernatant was mixed with an appropriate volume of ultrapure water before LC-MS/MS analysis.

To determine the Lucifer Yellow leakage after 2 hour transport period, stock solution of Lucifer yellow was prepared in DMSO and diluted with HBSS (10 mM HEPES, pH 7.4) to reach a final concentration of 100 µM. Lucifer yellow solution (100 µL) was added to each Transwell insert (apical compartment), followed by filling the wells in the receiver plate (basolateral compartment) with 300 µL of HBSS (10 mM HEPES, pH 7.4). The plates were Incubated at 37° C. for 30 mins then 80 µL samples were removed directly from the apical and basolateral wells (using the basolateral access holes) and transferred to wells of new 96 well plates. The Lucifer Yellow fluorescence (to monitor monolayer integrity) signal was measured in a fluorescence plate reader at 480 nM excitation and 530 nM emission.

Data Analysis. The apparent permeability coefficient (Papp), in units of centimeter per second, was calculated for MDCK-MDR1 drug transport assays using the following equation:

$$P_{app}=(V_A \times [drug]acceptor)/(Area \times Time \times [drug]_{initial,donor})$$

VA is the volume (in mL) in the acceptor well, Area is the surface area of the membrane (0.143 cm$^2$ for Transwell-96 Well Permeable Supports), and time is the total transport time in seconds.

The efflux ratio was determined using the following equation:

$$\text{Efflux Ratio } P=P_{app(B-A)}/P_{app(A-B)}$$

WP$_{app\,(B-A)}$ indicates the apparent permeability coefficient in basolateral to apical direction, and P$_{app\,(A-B)}$ indicates the apparent permeability coefficient in apical to basolateral direction.

The recovery can be determined using the following equation:

$$\text{Recovery \%}=(V_A \times [drug]_{acceptor}+V_D \times [drug]_{donor})/(V_D \times [drug]_{initial,donor})$$

V$_A$ is the volume (in mL) in the acceptor well (0.235 mL for Ap→Bl flux, and 0.075 mL for Bl→Ap), V$_D$ is the volume (in mL) in the donor well (0.075 mL for Ap→Bl flux, and 0.235 mL for Bl→Ap).

The leakage of Lucifer Yellow, in unit of percentage (%), was calculated using the following equation:

$$\%\text{ LY leakage}=100 \times [LY]_{acceptor}/([LY]_{donor}+[LY]_{acceptor})$$

LY leakage of <1% is acceptable to indicate the well-qualified MDCK-MDR1 monolayer.

Efflux rates and the ratio for select compounds are summarized in Table 4, below.

TABLE 4

MDCK-MDR1 Efflux Rates and Ratio

| Compound | A-B (10$^{-6}$, cm) | B-A (10$^{-6}$, cm) | Efflux Ratio |
|---|---|---|---|
| 03-3 | 25.34 | 19.76 | 0.78 |
| 03-5 | 15.24 | 16.21 | 1.06 |
| 03-115 | 6.96 | 10.98 | 1.58 |

Microsomal and Hepatocyte Stability

Microsomal Stability Protocol:

The master solution was prepared as follows.

| Reagent | Stock Concentration | Volume | Final Concentration |
|---|---|---|---|
| Phosphate buffer | 200 mM | 200 µL | 100 mM |
| Ultra-pure H$_2$O | — | 106 µL | — |
| MgCl$_2$ solution | 50 mM | 40 µL | 5 mM |

Two separate experiments were performed as follows:

With NADPH: 10 µL of 20 mg/mL liver microsomes and 40 µL of 10 mM NADPH were added to the incubations. The final concentrations of microsomes and NADPH were 0.5 mg/mL and 1 mM, respectively.

Without NADPH: 10 µL of 20 mg/mL liver microsomes and 40 µL of ultra-pure H$_2$O were added to the incubations. The final concentration of microsomes was 0.5 mg/mL.

The reaction was started with the addition of 4 µL of 3, 10, 30 and 100 µM test compound solution or control compound solution at the final concentration of 0.03, 0.1, 0.3 and 1 µM and carried out at 37° C.

Aliquots of 50 µL were taken from the reaction solution at 0, 15, 30, 45 and 60 min. The reaction was stopped by the addition of 4 volumes of cold acetonitrile with IS (100 nM alprazolam, 200 nM labetalol, 200 nM caffeine and 2 µM ketoprofen). Samples were centrifuged at 3, 220 g for 40 minutes. Aliquot of 100 µL of the supernatant was mixed with 100 µL of ultra-pure H$_2$O and then used for LC-MS/MS analysis.

Data Analysis:

All calculations were carried out using Microsoft Excel.

Peak areas were determined from extracted ion chromatograms. The slope value, k, was determined by linear regression of the natural logarithm of the remaining percentage of the parent drug vs. incubation time curve.

The in vitro half-life (in vitro t$_{1/2}$) was determined from the slope value:

$$\text{in vitro } t_{1/2}=-(0.693/k)$$

Conversion of the in vitro t$_{1/2}$ (min) into the in vitro intrinsic clearance (in vitro CL$_{int}$, in µL/min/mg protein) was done using the following equation (mean of duplicate determinations):

$$\text{in vitro } CL_{int} = \frac{0.693}{t_{1/2}} \times \frac{\text{volume of incubation (µL)}}{\text{amount of proteins (mg)}}$$

Conversion of the in vitro $t_{1/2}$ (mM) into the scale-up unbound intrinsic clearance (Scale-up $CL_{int}$, in mL/min/kg) was done using the following equation (mean of duplicate determinations):

$$\text{Scale up } CL_{int} = \frac{0.693}{t_{1/2}} \times \frac{\text{volume of incubation (μL)}}{\text{amount of proteins (mg)}} \times \text{Scaling Factor}$$

Scaling Factors for Intrinsic Clearance Prediction in Liver Microsomes:

| Species | Liver Weight (g liver/kg body weight)[a] | Microsomal Concentration (mg/g liver)[b] | Liver blood flow (Q, mL/min/kg)[a] | Scaling Factor |
|---|---|---|---|---|
| Human | 25.7 | 48.8 | 20.7 | 1254.2 |
| Monkey | 30.0 | 50.0 | 43.6 | 1500.0 |
| Dog | 32.0 | 77.9 | 30.9 | 2492.8 |
| Rat | 40.0 | 44.8 | 55.2 | 1792.0 |
| Mouse | 88.0 | 50.0 | 90.0 | 4400.0 |

[a]Iwatsubo et al, Davies and Morris, 1993, 10 (7) pp 1093-1095.
[b]Barter et al, 2007, Curr Drug Metab, 8(1), pp 33-45; Iwatsubo et al, 1997, JPET, 283 pp 462-469.

Microsomal stability results (pL/min/mg protein) for select compounds are summarized in Table 5, below.

TABLE 5

Microsomal Stability Results.

| Compound | Rat | Human | Dog |
|---|---|---|---|
| 03-3 | 3.48 | 3.49 | 7.99 |
| 03-5 | 2.53 | 2.96 | 4.32 |

Hepatocyte Stability Protocol:
Preparation of Working Solutions 10 mM and 100 μM stock solutions of test compound(s) and a positive control were prepared in appropriate solvent (DMSO). In separate conical tubes, the 10 mM test compound and the positive control were diluted to 100 μM by combining 198 μL of 50% acetonitrile/50% water and 2 μL of 10 mM stock. The 100 μM test compound and the positive control were diluted to 30 μM by combining 140 μL of 50% acetonitrile/50% water and 60 μL of 100 μM stock solution. The 100 μM test compound and the positive control were diluted to 10 μM by combining 180 μL of 50% acetonitrile/50% water and 20 μL of 100 μM stock solution. The 100 μM test compound and the positive control were diluted to 3 μM by combining 194 μL of 50% acetonitrile/50% water and 6 μL of 100 μM stock solution.

Preparation of Hepatocytes

Incubation medium (William's E Medium supplemented with GlutaMAX) and hepatocyte thawing medium was placed in a 37° C. water bath, and allowed to warm for at least 15 minutes prior to use. A vial of cryopreserved hepatocytes from storage was then removed, ensuring that the vial remains at cryogenic temperatures until thawing process ensues. Cells were thawed by placing the vial in a 37° C. water bath and gently shaking the vial for 2 minutes. After thawing was completed, the vial was sprayed with 70% ethanol and transferred to a biosafety cabinet.

A wide-bore pipette tip was used to transfer hepatocytes into 50 mL conical tube containing thawing medium. The 50 mL conical tube was placed into a centrifuge and spun at 100 g for 10 minutes. Upon completion of spin, the thawing medium was aspirated and the hepatocytes were resuspended in enough incubation medium to yield ~$1.5 \times 10^6$ cells/mL.

Using AOPI staining solution, cells were counted and the viable cell density was determined. Cells with poor viability (<75% viability) are not acceptable for use. Cells were then diluted with incubation medium to a working cell density of $0.5 \times 10^6$ viable cells/mL. A portion of the hepatocytes at $0.5 \times 10^6$ viable cells/mL were boiled for 5 min prior to adding to the plate as representative of a negative control, in order to eliminate the enzymatic activity so that little or no substrate turnover should be observed.

Procedure for Stability Determination

198 μL of hepatocytes were pipetted into each wells of a 96-well non-coated plate. The plate was placed in the incubator on an orbital shaker to allow the hepatocytes to warm for 10 minutes. 2 μL of the 3, 10, 30 and 100 μM test compound or positive control were pipeted into respective wells of the 96-well non-coated plate to start the reaction. The final concentration of test compound or control compounds was 0.03, 0.1, 0.3 and 1 μM. The plate was returned to the incubator and placed on an orbital shaker.

Well contents were removed in 25 μL aliquots at time points of 0, 15, 30, 60, 90 and 120 minutes. The aliquots were then mixed with 6 volumes (150 μL) of acetonitrile containing internal standards (IS: 100 nM alprazolam, 200 nM labetalol, 200 nM caffeine and 2 μM ketoprofen) to terminate the reaction. The plate was centrifuged for 20 minutes at 3,220 g. An aliquot of 100 μL of the supernatant was mixed with 100 μL of ultra-pure $H_2O$ and then used for LC-MS/MS analysis. All incubations were performed in duplicate. Hepatocyte stability results (μL/min/$10^6$ cells) for select compounds are summarized in Table 6, below.

Data Analysis

All calculations were carried out using Microsoft Excel. Peak areas were determined from extracted ion chromatograms. Determine the in vitro half-life ($t_{1/2}$) of parent compound by regression analysis of the percent parent disappearance vs. time curve.

The in vitro half-life (in vitro $t_{1/2}$) was determined from the slope value: in vitro $t_{1/2}=0.693/k$ Conversion of the in vitro $t_{1/2}$ (in min) into the scale-up intrinsic clearance (Scaled-up $CL_{int}$, in mL/min/kg) was done using the following equation (mean of duplicate determinations): Scaled-up $CL_{int}=kV/N$ x scaling factor; V=incubation volume (0.2 mL); N=number of hepatocytes per well ($0.1 \times 10^6$ cells).

Scaling factors for in vivo intrinsic clearance prediction using different species of hepatocytes are listed below:

| Species | Liver Weight (g liver/kg body weight) | Hepatocyte Concentration ($10^6$ cells/g liver) | Scaling Factor |
|---|---|---|---|
| Human | 25.7 | 99 | 2544.3 |
| Monkey | 30 | 120 | 3600.0 |
| Dog | 32 | 215 | 6880.0 |
| Rat | 40 | 117 | 4680.0 |
| Mouse | 87.5 | 135 | 11812.5 |

TABLE 6

Hepatocyte Stability Results.

| Compound | Rat | Human | Dog | Monkey | Mouse |
| --- | --- | --- | --- | --- | --- |
| 03-3 | 4.59 | 0.9 | 5.3 | — | — |
| 03-5 | 3.54-4.62 | 0.36-0.59 | 5.94-7.63 | 1.88 | 1.46 |
| 03-115 | 20.61 | 0.32 | 8.13 | 1.26 | 1.08 | hERG Cardiotoxicity

TABLE 7

Materials and Instrumentation

| Materials | Vendor (Cat #) |
| --- | --- |
| 6 cm cell culture dish | Nunc (Cat. 150288) |
| 3.5 cm cell culture dish | Nunc (Cat# 153066) |
| Fetal Bovine Serum Dialyzed | Invitrogen (Cat# 30067334) |
| DMSO | Merck (Cat. 102952) |
| DMEM medium | Gibco (Cat. 10569) |
| 1XPBS without $Ca^{2+}/Mg^{2+}$ | Gibco (Cat. 14190) |
| TrypLE ™ Express | Invitrogen (Cat. 12604) |
| HEPES 1M Buffer(100 mL) | Invitrogen (Cat. 15630-080) |
| Penicillin-Streptomycin(10000 U/mL) | Invitrogen (Cat. 15140122) |
| MEM + NEAA | Invitrogen (Cat. 11140) |
| G418 | Invitrogen (Cat. 11811031) |
| Blasticidin | Invitrogen (Cat. R21001) |
| Doxycycline | Sigma (Cat. D9891) |
| Instrumentation | Vendor |
| Steri-Cycle $CO_2$ Incubator | Thermo(Cat. 371) |
| Micropipette Puller | Sutter P-97 Model |
| Micro manipulators | Siskiyou MC1000e Controller |
| Multiclamp 700B Amplifier | AXON |
| EPC10 Amplifier | HEKA |
| Microscope | Olympus IX51/71/73 |
| Perfusion system | ALA VM8 gravity-flow delivery system |

Cell lines and cell culture. HEK 293 cell line stably expressing hERG channel (Cat #K1236) was purchased from Invitrogen. The cells are cultured in 85% DMEM, 10% dialyzed FBS, 0.1 mM NEAA, 25 mM HEPES, 100 U/mL Penicillin-Streptomycin and 5 µg/mL Blasticidin and 400 µg/mL Geneticin. Cells were split using TrypLE™ Express about three times a week, and maintained between ~40% to −80% confluence. Before the assay, the cells were transferred onto the coverslips at $5 \times 10^5$ cells/per 6 cm cell culture dish and induced with doxycycline at 1 µg/mL for 48 hours.

Solution preparations. Extracellular solution (in mM): 132 NaCl, 4 KCl, 3 $CaCl_2$, 0.5 $MgCl_2$, 11.1 glucose, and 10 HEPES (pH adjusted to 7.35 with NaOH) Intracellular solution (in mM): 140 KCl, 2 $MgCl_2$, 10 EGTA, 10 HEPES and 5 MgATP (pH adjusted to 7.35 with KOH).

Working solution preparation for test compounds. Test compounds were initially prepared in DMSO with final stock solution concentrations of 10 or 30 mM. Stock solutions of test compounds were then serial-diluted with DMSO (1:3) to prepare additional intermediate solutions including 10, 3.33, 1.11 and 0.37 mM. Before hERG assay, the working solutions were prepared by dilution of 30, 10, 3.33, 1.11 and 0.37 mM intermediate solutions in 1000 folds using extracellular solution, so that the final concentration of working solution was 30, 10, 3.33, 1.11 and 0.37 µM. The final DMSO concentration in working solutions was 0.1-0.3% (v/v). Human ERG current in presence of 5 doses was tested for $IC_{50}$ determination.

Experimental procedure. The coverslip was removed from the cell culture dish and placed on the microscope stage in bath chamber. A desirable cell was located using the ×10 objective. The tip of the electrode was located under the microscope using the ×10 objective by focusing above the plane of the cells. Once the tip was in focus, the electrode downwards was advanted towards the cell using the coarse controls of the manipulator, while simultaneously moving the objective to keep the tip in focus. The fine controls of the manipulator were then used to approach the cell in small steps. Gentle suction was applied through the side-port of the electrode holder to form a gigaohm seal. The $C_{fast}$ was used to remove the capacity current that was in coincidence with the voltage step. The whole cell configuration was obtained by applying repetitive, brief, strong suction until the membrane patch ruptured. The membrane potential was then set to −60 mV to ensure that hERG channels was not open. The spikes of capacity current were then be cancelled using the $G_{low}$ on the amplifier. The holding potential was set to −90 mV for 500 ms and the current was recorded at 50 kHz and filtered at 10 kHz. The leaking current was tested at −80 mV for 500 ms.

The hERG current was elicited by depolarizing at +30 mV for 4.8 seconds and then the voltage was taken back to −50 mV for 5.2 seconds to remove the inactivation and observe the deactivating tail current. The maximum amount of tail current size was used to determine hERG current amplitude. The current was recorded for 120 seconds to assess the current stability. Only stable cells with recording parameters above threshold were applied for the drug administrations.

Vehicle control was applied to the cells to establish the baseline. Once the hERG current was found to be stabilized for 3 minutes, test compound was applied. hERG current in the presence of test compound was recorded for approximately 5 minutes to reach steady state and then 5 sweeps were captured. For dose response testing, 5 doses of compound were applied to the cells cumulatively from low to high concentrations. To ensure the good performance of cultured cells and operations, 5 dose concentrations of the positive control, Dofetilide, were also used to test the same batch of cells.

Data analysis. The following criteria were used to determine data acceptability.
1) Initial seal resistance >1 GΩ;
2) Stable leakage current <100 pA at a test potential;
3) The peak tail amplitude >250 pA;
4) Membrane resistance Rm >500 MΩ;
5) Access resistance (Ra) <10 MΩ;
6) Apparent run-down of peak current <2.5% per min Data that met the above criteria for hERG current quality were further analyzed. Percent hERG current inhibition was calculated using the following equation.

Peak current inhibition=(1−)×100

Peak Tail Current Vehicle

The dose response curve of test compounds was plotted with percentage of hERG current inhibition against the concentration of test compounds using Graphpad Prism 6.0, and fit to a sigmoid dose-response curve with a variable slope. PatchMaster software was used to extract the peak current from the original data. Roche et al. A Virtual Screening Method for Prediction of the hERG Potassium Channel Liability of Compound Libraries. (2002) *ChemBioChem*. 3, 455-459; Glenn E. Kirsch et al. Variability in the measurement of hERG potassium channel inhibition: effects of temperature and stimulus patter. (2004) *Journal of Pharmacological and Toxicological Methods* 50, 93-101; Roger Marrannes et al. Computer programs to facilitate the estimation of time-dependent drug effects on ion channels. (2004) *Computer Methods and Programs in Biomedicine* 74, 167-181; SOP-ADMET-MAN-007: The Standard Operating Procedure for Compound Management.

hERG manual patch clamp $IC_{50}$ results (μM) for select compounds are summarized in Table 8, below.

It has been surprisingly found that certain compounds of the present disclosure exhibit unexpectedly low cardiac toxicity.

TABLE 8 hERG $IC_{50}$ Results.

| Compound | $IC_{50}$ |
|---|---|
| 03-3 | >30 |
| 03-5 | >30 |

Cytochrome P450 Inhibition Evaluation

TABLE 9

Preparation of Master Solution.

| Reagent | Stock Concentration | Volume | Final Concentration |
|---|---|---|---|
| MgCl$_2$ solution | 50 mM | 20 μL | 5 mM |
| Phosphate buffer | 200 mM | 100 μL | 100 mM |
| Ultra-pure H$_2$O | — | 56 μL | — |
| Human liver microsomes | 20 mg/mL | 2 μL | 0.2 mg/mL |

Stock compound solution (1 μL at 2 mM) or DMSO (1 μL) of was added to the master solution. The final concentration of test compound or control compounds was 10 μM.

For CYP1A2 inhibition, 1 μL of specific drug substrate (Phenacetin: 8 mM) was added at the final concentration of 40 μM to the master solution.

For CYP2B6 inhibition, 1 μL of specific drug substrate (Bupropion: 10 mM) was added at the final concentration of 50 μM to the master solution.

For CYP2C9 inhibition, 1 μL of specific drug substrate (Tolbutamide: 40 mM) was added at the final concentration of 200 μM to the master solution.

For CYP2C19 inhibition, 1 μL of specific drug substrate ((s)-Mephenytoin: 10 mM) was added at the final concentration of 50 μM to the master solution.

For CYP3A4 inhibition, 1 μL of specific drug substrate (Midazolam: 1 mM) was added at the final concentration of 5 μM to the master solution.

For CYP3A4 inhibition, 1 μL of specific drug substrate (Testosterone: 10 mM) was added at the final concentration of 50 μM to the master solution.

The mixtures were pre-warmed at 37° C. for 5 min. The reactions were started by the addition of 20 μL of 10 mM NADPH solution at the final concentration of 1 mM and carried out at 37° C. The reaction was stopped by addition of 400 μL of cold quench solution (methanol containing internal standards (IS: 100 nM alprazolam, 500 nM labetalol and 2 μM ketoprofen)) at the designated time points (Phenacetin: 20 mM; Bupropion: 20 mM; Tolbutamide: 20 mM; (s)-Mephenytoin: 20 mM; Midazolam: 5 mM; Testosterone: 10 min). Samples were vortexed for 5 minutes and centrifuged at 3220 g for 40 minutes at 4° C. And then 100 μL of the supernatant was transferred to a new 96-well plate with 100 μL water for LC-MS/MS analysis. All experiments were performed in duplicate.

Percent CYP450 isoform inhibition results (10 μM) for select compounds are summarized in Table 10, below.

It has been surprisingly found that certain compounds of the present disclosure exhibit unexpectedly low inhibition of CYP450 enzymes, and as such have a low potential for drug-drug interactions.

TABLE 10

Percent CYP450 Isoform Inhibition.

| Compound | 1A2 | 2B6 | 2C9 | 2C19 | 2D6 | 3A4M | 3A4T |
|---|---|---|---|---|---|---|---|
| C3-3 | 6% | 11% | 1% | 1% | 19% | 0% | −10% |
| C3-5 | 16% | N/A | −8% | 1% | 23% | −2% | −3% |

Example 4: Rat Pharmacokinetic Studies

The rat pharmacokinetics studies of exemplary compounds 03-3, 03-5, and 03-115 were conducted with male SD rats. These rats were typically about 6-8 weeks old, weighing 200 g to 300 g. Animals were fasted overnight and free access to food 4 hours after dosing. A required volume of vehicle was added to reach the target concentration of the test article and vehicle component to prepare for the dosing. The dosing vehicle was PEG400 or 30% PEG400 in saline for IV, or 0.5% methylcellulose in water for PO. For IV dosing, the animals were administered intravenously via tail vein. For PO dosing, the animals were administered via oral gavage. After dosing, blood sample was collected (~0.2 mL per time point) through jugular vein or heart puncture. Blood of each sample was transferred into plastic micro centrifuge tubes containing EDTA-K2. Collection tubes with blood samples and anticoagulant were inverted several times for proper mixing of the tube contents and then placed on wet ice. The blood samples were centrifuged at 2000 g for 5 minutes at 4° C. to obtain plasma which was stored in a freezer at −75±15° C. prior to analysis. Samples were analyzed using LC-MS/MS. WinNonlin were used for pharmacokinetic calculations.

For CSF sampling, after anesthesia, the foramen magnum was exposed, and a syringe was used with a venoclysis needle to sample the CSF. The CSF samples were stored in polypropylene tubes, then stored in a freezer at −75±15° C. prior to analysis.

For brain sampling, the rats were fully exsanguinated by using a risen of carbon dioxide prior to brain collection. Brain samples were then collected at adopted time point, quick frozen and kept at −75±15° C. All brain samples were weighted and homogenated with PBS by brain weight (g) to PBS volume (mL) ratio 1:3 before analysis. The actual concentration is the detected value multiplied by the dilution factor.

Exemplar PK results for IV dosing are summarized in Tables 11-13, below. Exemplar PK results for PO dosing are summarized in Tables 14-16, below.

Exemplar CNS exposure results for IV and SC dosing are summarized in Tables 17-19, below. Exemplar CNS exposure results for PO dosing are summarized in Table 20, below.

Figure 4:
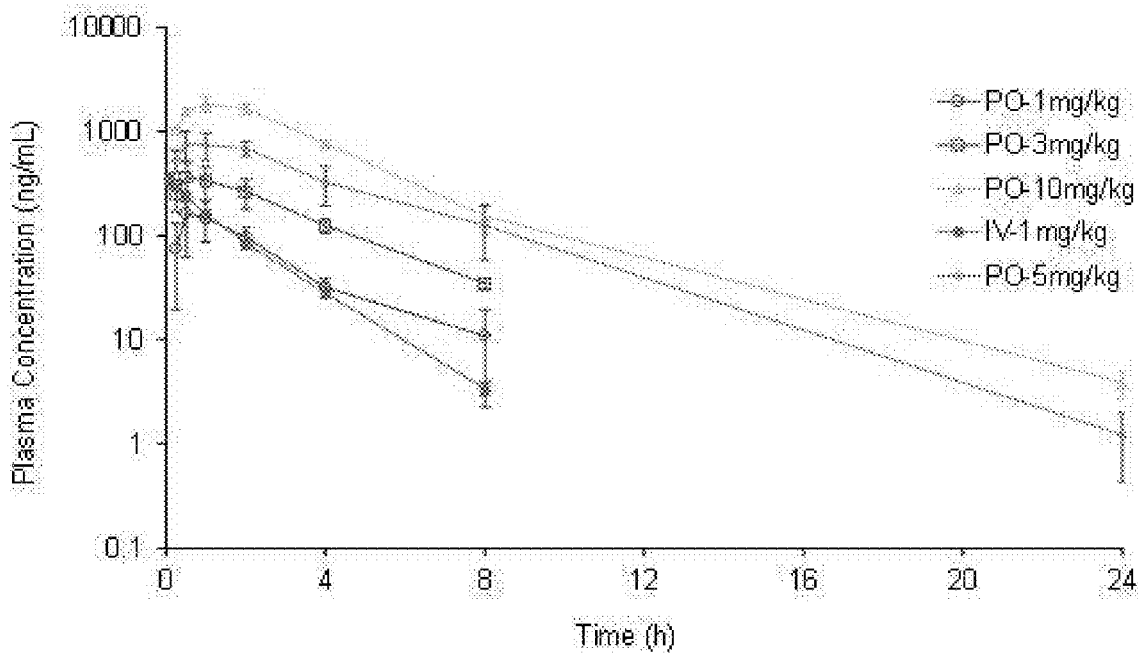
FIG. 4 summarizes the pharmacokinetic properties of Compound 03-3 in male SD rats following oral (1, 3, 5, and 10 mg/kg) and intravenous (1 mg/kg) administration.
Figure 5:
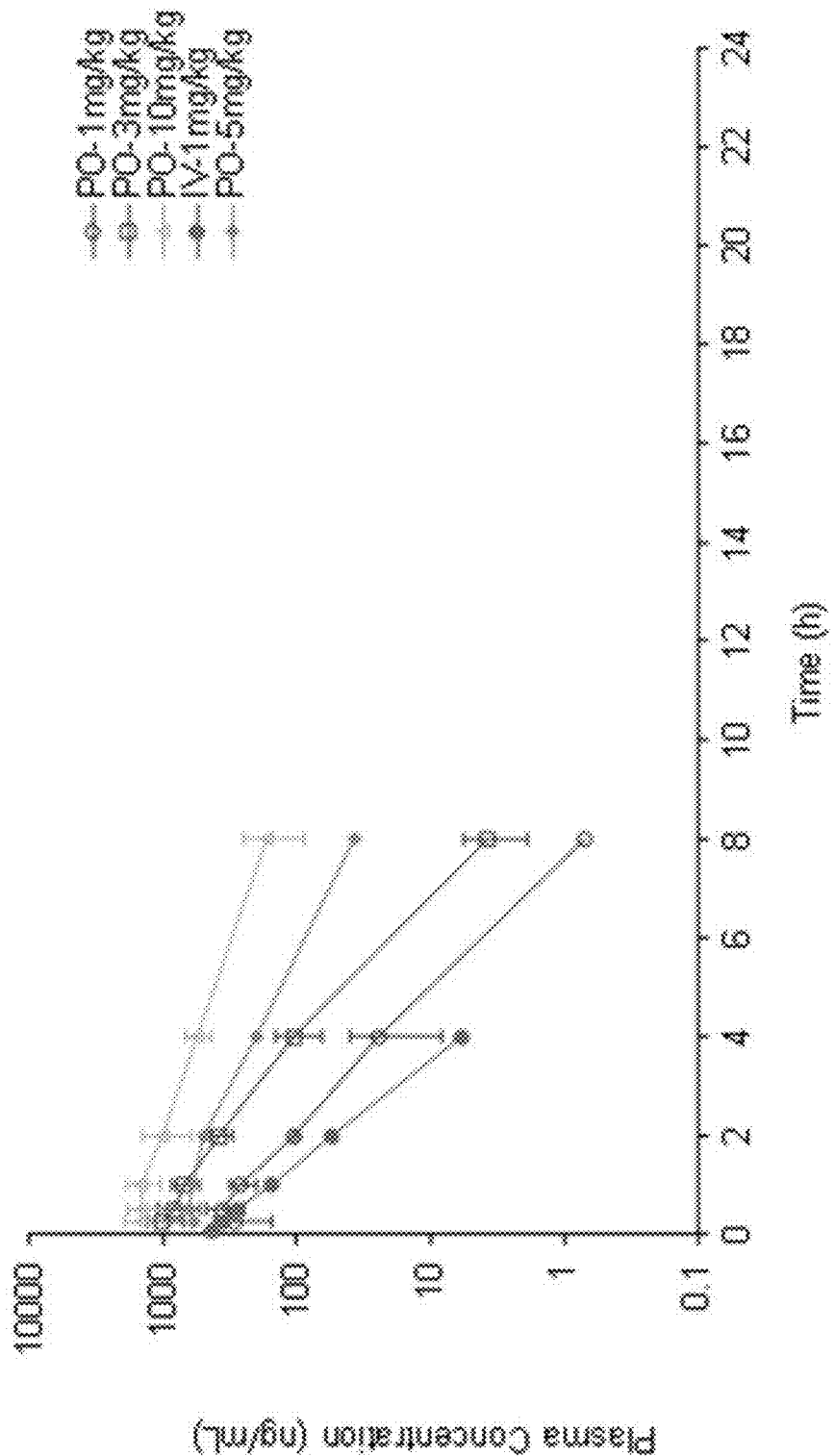
FIG. 5 summarizes the pharmacokinetic properties of Compound 03-5 in male SD rats following oral (1, 3, 5, and 10 mg/kg) and intravenous (1 mg/kg) administration.
Figure 12:
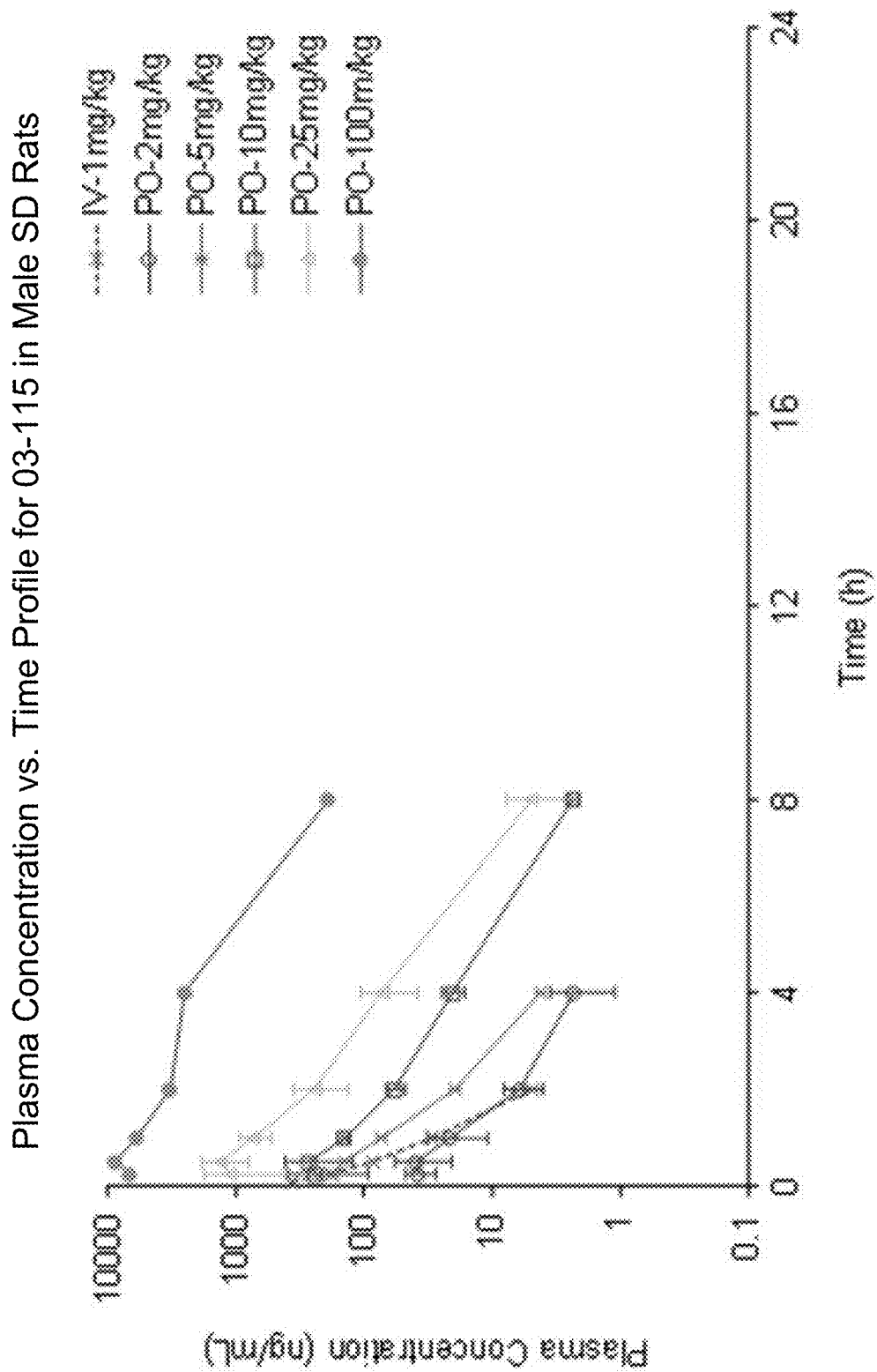
FIG. 12 summarizes the pharmacokinetic properties of Compound 03-115 in male SD rats following oral (1, 2, 5, 10, 25 and 100 mg/kg) and intravenous (1 mg/kg) administration.

PK results in male SD rats are further summarized in FIGS. 4-5, and 12.

It has been surprisingly found that compounds of the present disclosure have excellent absorption and overall exposure characteristics. Furthermore, it has been surprisingly found that compounds of the present disclosure exhibit excellent CNS exposure and accumulation.

TABLE 11

Rat IV Pharmacokinetic results for Compound 03-3.

| PK parameters | Unit | IV dose 1 mg/kg |
|---|---|---|
| Cl_obs | mL/min/kg | 30.2 |
| $T_{1/2}$ | h | 1.28 |
| $C_0$ | ng/mL | 388 |
| $AUC_{last}$ | h*ng/mL | 546 |
| $AUC_{Inf}$ | h*ng/mL | 552 |
| $AUC\_\%_{Extrap}\_obs$ | % | 1.14 |
| $MRT_{Inf}\_obs$ | h | 1.61 |
| $AUC_{last}/D$ | h*mg/mL | 546 |
| $V_{ss}\_obs$ | L/kg | 2.92 |

TABLE 12

Rat IV Pharmacokinetic results for Compound 03-5.

| PK parameters | Unit | IV Dose 1 mg/kg |
|---|---|---|
| Cl_obs | mL/min/kg | 37.3 |
| $T_{1/2}$ | h | 0.644 |
| $C_0$ | ng/mL | 468 |
| $AUC_{last}$ | h*ng/mL | 461 |
| $AUC_{Inf}$ | h*ng/mL | 463 |
| $AUC\_\%_{Extrap}\_obs$ | % | 0.457 |
| $MRT_{Inf}\_obs$ | h | 0.873 |
| $AUC_{last}/D$ | h*mg/mL | 461 |
| $V_{ss}\_obs$ | L/kg | 1.89 |

TABLE 13

Rat IV Pharmacokinetic results for Compound 03-115.

| PK parameters | Unit | IV Dose 1 mg/kg |
|---|---|---|
| Cl_obs | mL/min/kg | 103 |
| $T_{1/2}$ | h | 0.36 |
| $C_0$ | ng/mL | 512 |
| $AUC_{Inf}$ | h*ng/mL | 164 |
| $V_{ss}\_obs$ | L/kg | 2.4 |

TABLE 14

Rat PO Pharmacokinetic results for Compound 03-3.

| PK parameters | Unit | PO Dose 5 mg/kg |
|---|---|---|
| $T_{1/2}$ | h | 2.44 |
| $T_{max}$ | h | 1.17 |
| $C_{max}$ | ng/mL | 818 |
| $AUC_{last}$ | h*ng/mL | 4224 |
| $AUC_{Inf}$ | h*ng/mL | 4228 |
| $AUC\_\%_{Extrap}\_obs$ | % | 0.0970 |
| $MRT_{Inf}\_obs$ | h | 3.93 |
| $AUC_{last}/D$ | h*mg/mL | 845 |
| F | % | 153 |

TABLE 15

Rat PO Pharmacokinetic results for Compound 03-5.

| PK parameters | Unit | PO Dose 5 mg/kg |
|---|---|---|
| $T_{1/2}$ | h | 1.61 |
| $T_{max}$ | h | 0.750 |
| $C_{max}$ | ng/mL | 717 |
| $AUC_{last}$ | h*ng/mL | 2248 |
| $AUC_{Inf}$ | h*ng/mL | 2339 |
| $AUC\_\%_{Extrap}\_obs$ | % | 4.10 |
| $MRT_{Inf}\_obs$ | h | 2.62 |
| $AUC_{last}/D$ | h*mg/mL | 450 |
| F | % | 101 |

TABLE 16

Rat PO Pharmacokinetic results for Compound 03-115.

| PK parameters | Unit | PO Dose 5 mg/kg |
|---|---|---|
| $T_{1/2}$ | h | 1.61 |
| $T_{max}$ | h | 0.25 |
| $C_{max}$ | ng/mL | 174 |
| $AUC_{Inf}$ | h*ng/mL | 192 |
| $MRT_{Inf}\_obs$ | h | 1.06 |
| F | % | 23 |

TABLE 17

Rat IV CNS exposure measurement for Compound 03-3.

| | IV Dose | | |
|---|---|---|---|
| | 1 | mg/kg Concentration | |
| Time (h) | Plasma (ng/mL) | CSF (ng/mL) | Brain (ng/g) |
| 1.00 | 199 | 142 | 680 |

TABLE 18

Rat IV CNS exposure measurement for Compound 03-5.

| | IV Dose | | |
|---|---|---|---|
| | 1 | mg/kg Concentration | |
| Time (h) | Plasma (ng/mL) | CSF (ng/mL) | Brain (ng/g) |
| 1.00 | 184 | 113 | 267 |

TABLE 19

Rat SC CNS exposure measurement for Compound 03-115.

| | SC Dose | | |
|---|---|---|---|
| | 1 | mg/kg Concentration | |
| Time (h) | Plasma (ng/mL) | CSF (ng/mL) | Brain (ng/g) |
| 1.00 | 149 | 56.2 | 142 |

TABLE 20

Rat PO CNS exposure measurement for Compound 03-5.

| | PO Dose | | |
|---|---|---|---|
| | 5 | mg/kg Concentration | |
| Time (h) | Plasma (ng/mL) | CSF (ng/mL) | Brain (ng/g) |
| 1.00 | 642 | 242 | 497 |

Example 5: Mouse Pharmacokinetic Studies

Mouse pharmacokinetics studies of exemplar compounds 03-3 and 03-5 were conducted substantially similarly to the rat pharmacokinetic studies, instead using male C57BL/6J mice. These mice were typically about 6-8 weeks old, weighing 20 g to 30 g. Animals were free access to food before dosing. Sample amount was ~0.03 mL per time point and sample site was dorsal metatarsal or heart puncture.

Exemplar PK results for PO dosing are summarized in Tables 21-23, below.

Exemplar CNS exposure results for PO and SC dosing are summarized in Tables 24-26, below.

Figure 6:
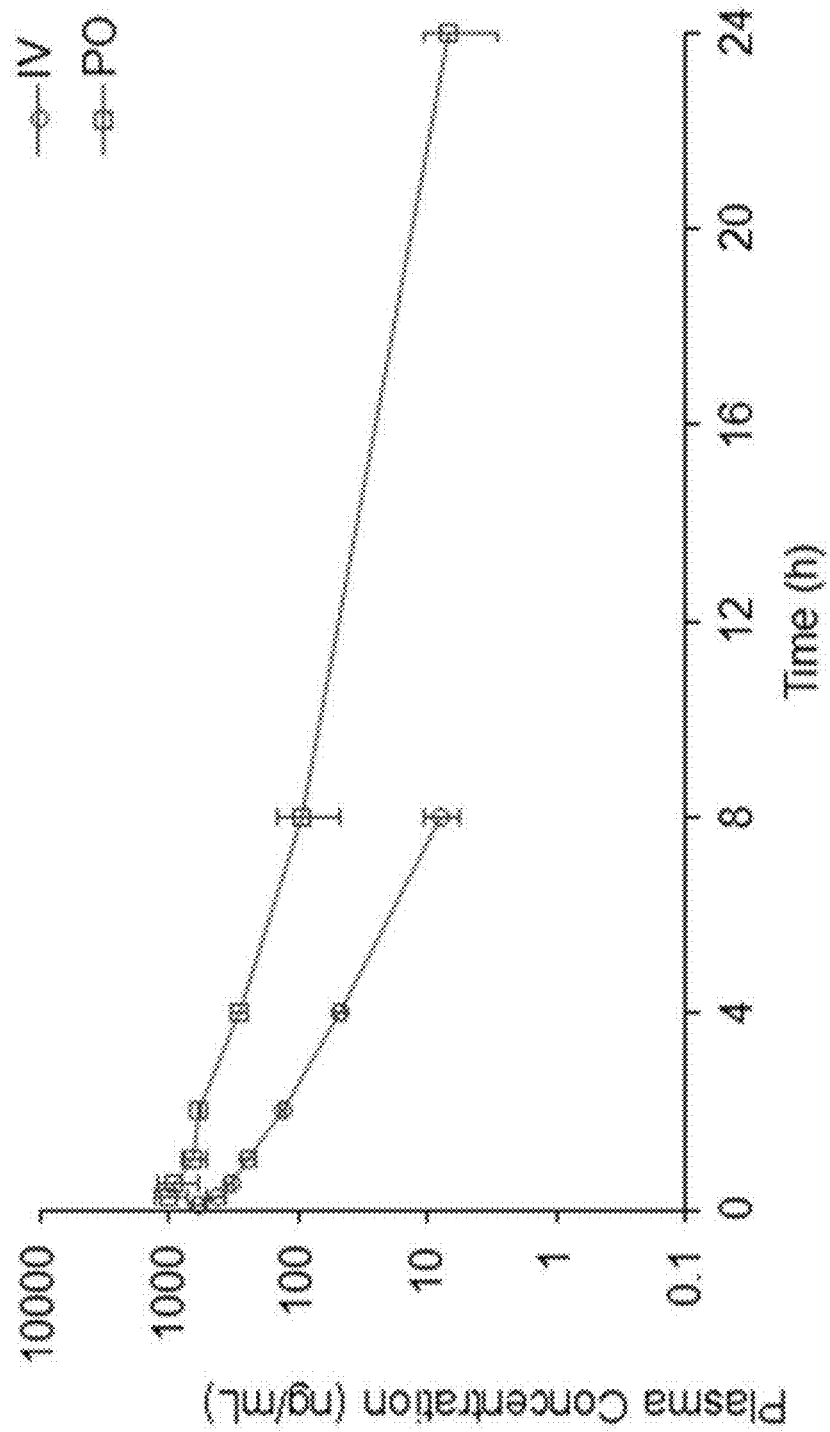
FIG. 6 summarizes the pharmacokinetic properties of Compound 03-3 in male C57BL/6J mice following oral (5 mg/kg) and intravenous (1 mg/kg) administration. The trend line containing squares denotes oral (PO) administration.
Figure 7:
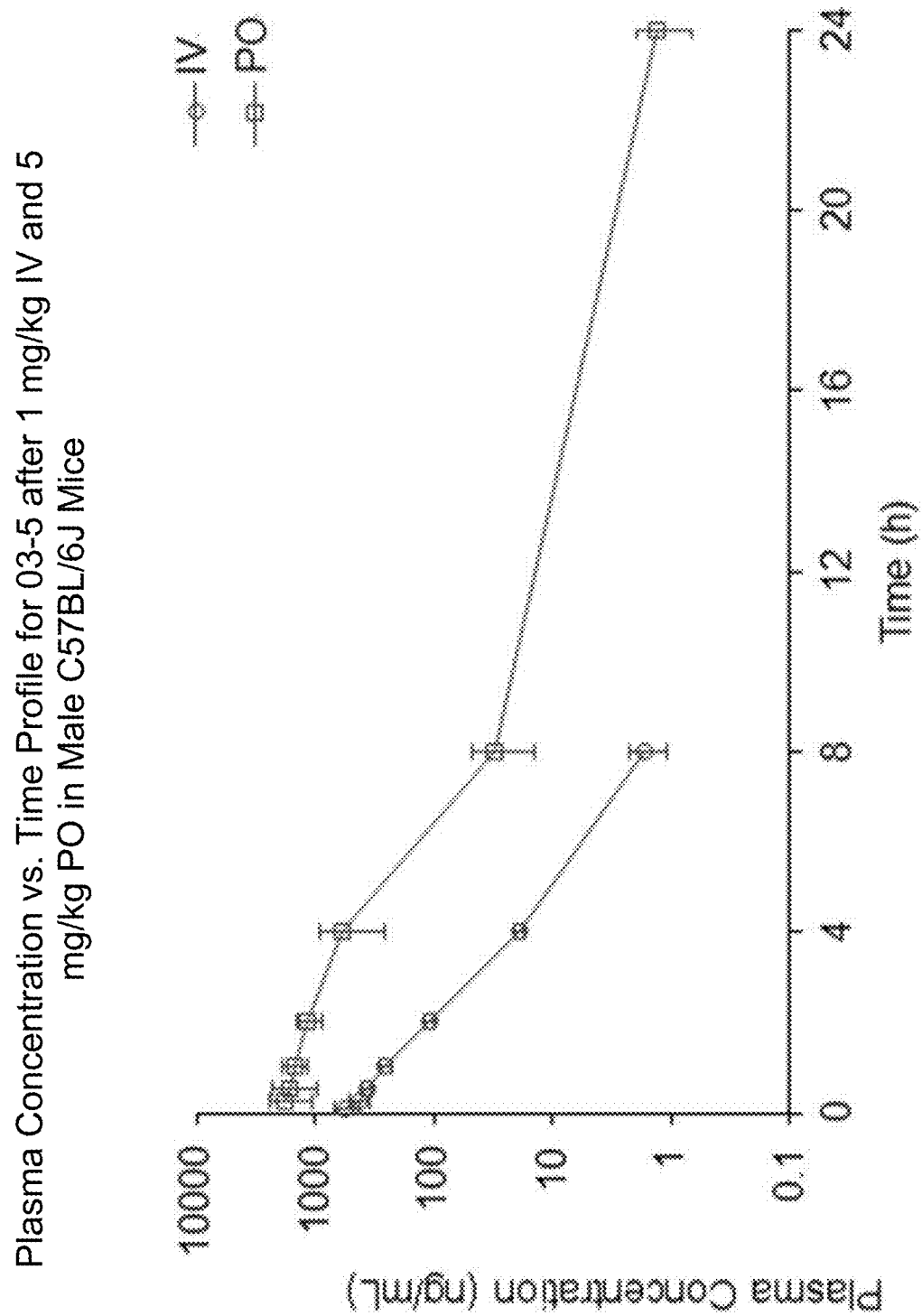
FIG. 7 summarizes the pharmacokinetic properties of Compound 03-5 in male C57BL/6J mice following oral (5 mg/kg) and intravenous (1 mg/kg) administration. The trend line containing squares denotes oral (PO) administration.
Figure 14:
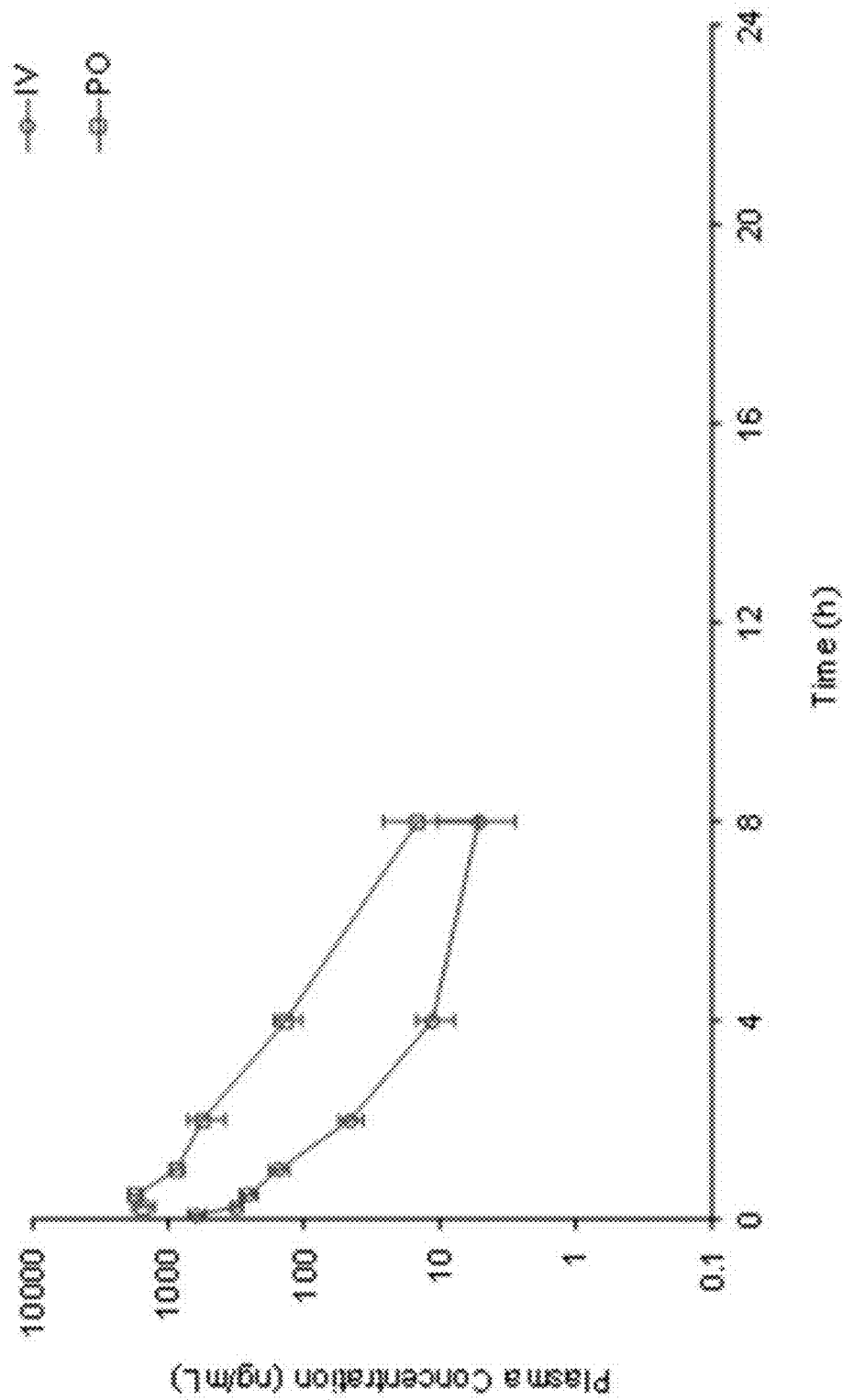
FIG. 14 summarizes the pharmacokinetic properties of Compound 03-115 in male C57BL/6J mice following oral (5 mg/kg) and intravenous (1 mg/kg) administration. The trend line containing squares denotes oral (PO) administration.

PK results in male C57BL/6J mice are further summarized in FIGS. 6-7, and 14.

It has been surprisingly found that compounds of the present disclosure have excellent absorption and overall exposure characteristics. Furthermore, it has been surprisingly found that compounds of the present disclosure exhibit excellent CNS exposure and accumulation.

TABLE 21

Mouse PO PK results for Compound 03-3.

| | | PO Dose |
|---|---|---|
| PK parameters | Unit | 5 mg/kg |
| $T_{1/2}$ | h | 3.78 |
| $T_{max}$ | h | 0.250 |
| $C_{max}$ | ng/mL | 1015 |
| $AUC_{last}$ | h*ng/mL | 3870 |
| $AUC_{Inf}$ | h*ng/mL | 3909 |
| $AUC\_\%_{Extrap}\_obs$ | % | 0.958 |
| $MRT_{Inf}\_obs$ | h | 4.08 |
| $AUC_{last}/D$ | h*mg/mL | 774 |
| F | % | 85.1 |

TABLE 22

Mouse PO PK results for Compound 03-5.

| | | PO Dose |
|---|---|---|
| PK parameters | Unit | 5 mg/kg |
| $T_{1/2}$ | h | 2.51 |
| $T_{max}$ | h | 0.917 |
| $C_{max}$ | ng/mL | 1937 |
| $AUC_{last}$ | h*ng/mL | 6071 |
| $AUC_{Inf}$ | h*ng/mL | 6076 |
| $AUC\_\%_{Extrap}\_obs$ | % | 0.0845 |
| $MRT_{Inf}\_obs$ | h | 2.43 |
| $AUC_{last}/D$ | h*mg/mL | 1214 |
| F | % | 163 |

TABLE 23

Mouse PO PK results for Compound 03-115.

| | | PO Dose |
|---|---|---|
| PK parameters | Unit | 5 mg/kg |
| $T_{max}$ | h | 0.5 |
| $C_{max}$ | ng/mL | 1751 |
| $AUC_{Inf}$ | h*ng/mL | 3018 |
| $MRT_{Inf}\_obs$ | h | 1.8 |
| F | % | 112 |

TABLE 24

Mouse PO CNS exposure measurement for Compound 03-3.

| | PO dose | | |
|---|---|---|---|
| | 5 | mg/kg Concentration | |
| Time (min) | Plasma (ng/mL) | CSF (ng/mL) | Brain (ng/g) |
| 100 | 557 | 302 | 988 |

TABLE 25

Mouse PO CNS exposure measurement for Compound 03-5.

| | PO Dose | | |
|---|---|---|---|
| | 5 | mg/kg | |
| | | Concentration | |
| Time (min) | Plasma (ng/mL) | CSF (ng/mL) | Brain (ng/g) |
| 100 | 1340 | 621 | 989 |

TABLE 26

Mouse SC CNS exposure measurement for Compound 03-115.

| | SC Dose | | |
|---|---|---|---|
| | 1 | mg/kg | |
| | | Concentration | |
| Time (min) | Plasma (ng/mL) | CSF (ng/mL) | Brain (ng/g) |
| 60 | 270 | 157 | 280 |

Example 6: Dog Pharmacokinetic Studies

Dog pharmacokinetics studies of exemplary compounds 03-3, 03-5, and 03-115 were conducted substantially similarly to the rat pharmacokinetic studies, instead using male Beagle dogs. Animals for PO studies were food fasted overnight prior to dosing and were fed approximately 2 hours after dosing. Animals for IV studies had free access to food and water. Blood samples were collected through venipuncture of peripheral veins except the dosing vein.

Exemplar PK results for PO dosing are summarized in Tables 27-32, below.

Figure 8:
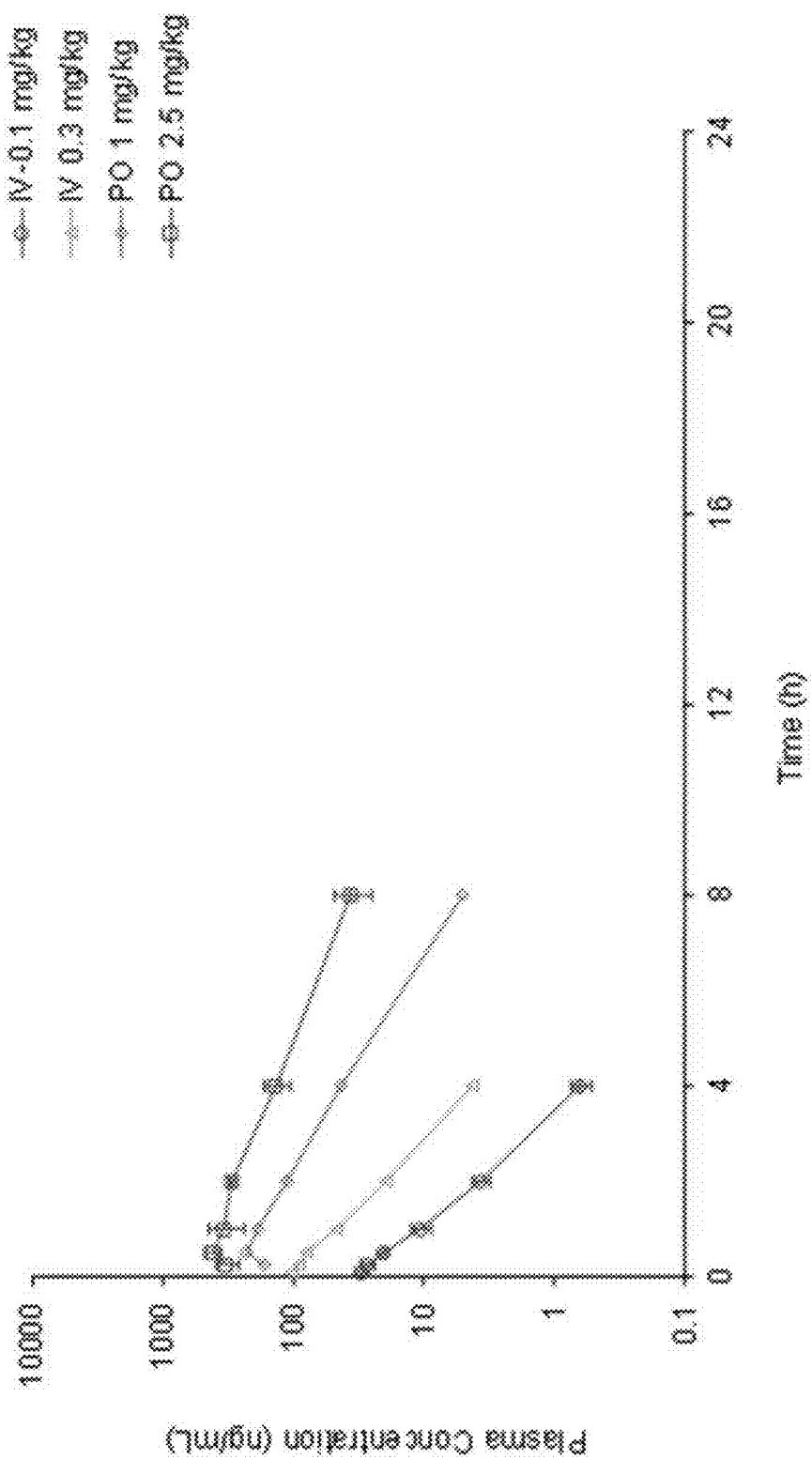
FIG. 8 summarizes the pharmacokinetic properties of Compound 03-3 in male Beagle dogs following oral (1 and 2.5 mg/kg) and intravenous (0.1 and 0.3 mg/kg) administration.
Figure 9:
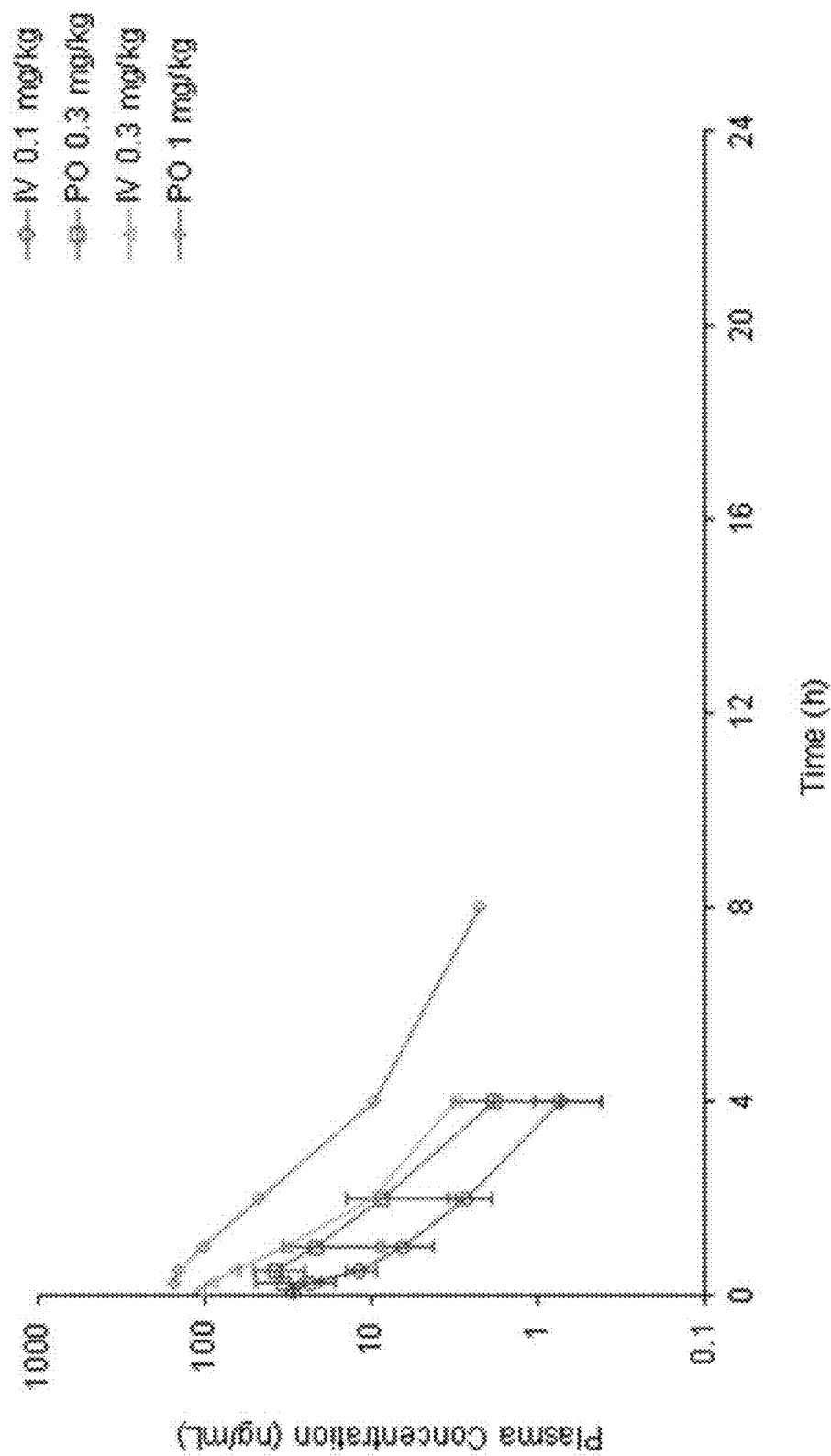
FIG. 9 summarizes the pharmacokinetic properties of Compound 03-5 in male Beagle dogs following oral (0.3 and 1 mg/kg) and intravenous (0.1 and 0.3 mg/kg) administration.
Figure 13:
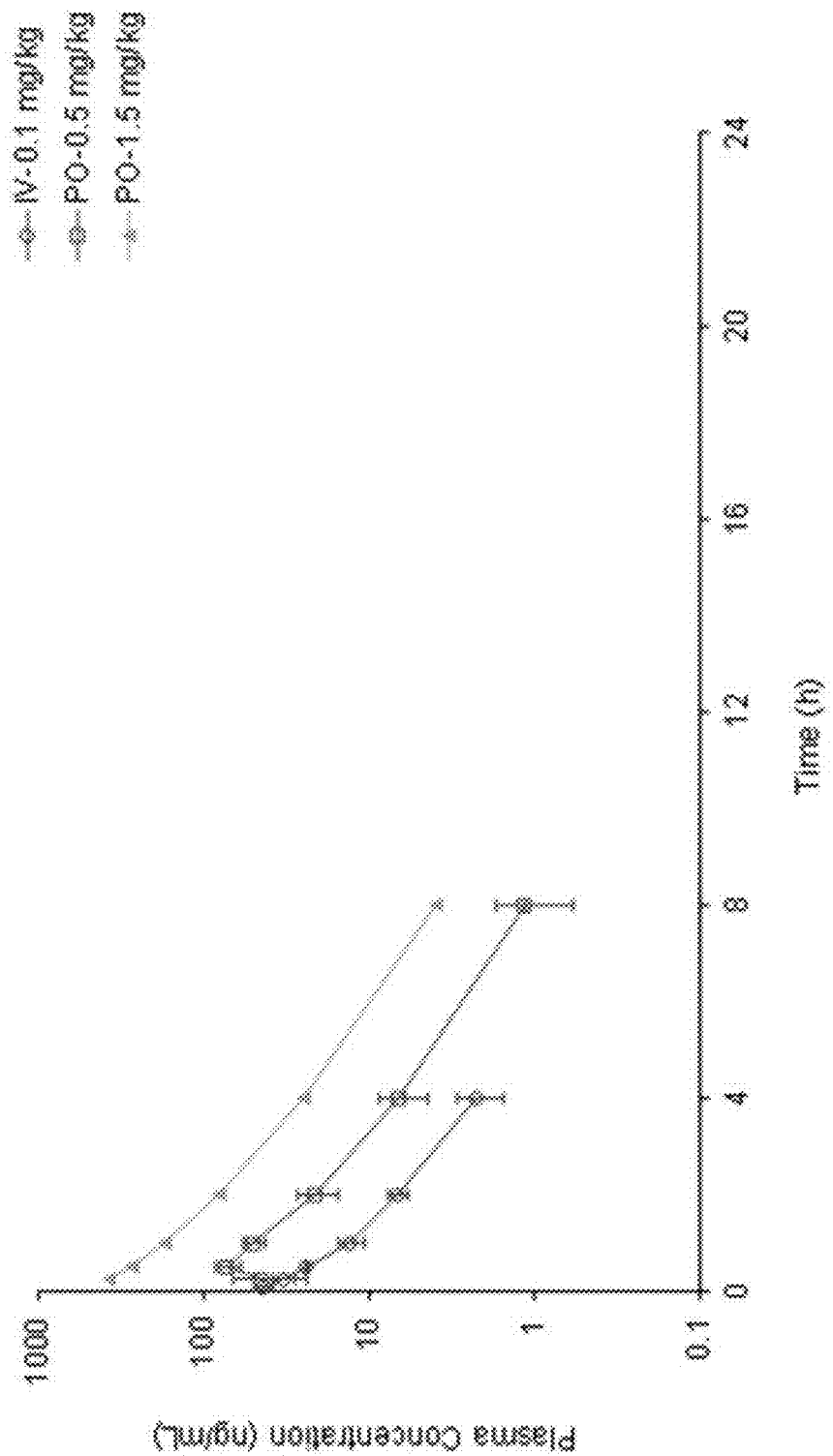
FIG. 13 summarizes the pharmacokinetic properties of Compound 03-115 in male Beagle dogs following oral (0.5 and 1.5 mg/kg) and intravenous (0.1 mg/kg) administration.

PK results in male Beagle dogs are further summarized in FIGS. 8-9, and 13.

TABLE 27

Dog PO PK results for Compound 03-3.

| | PO Dose | |
|---|---|---|
| PK parameters | Unit | 1 mg/kg |
| $T_{max}$ | h | 0.5 |
| $C_{max}$ | ng/mL | 227 |
| $AUC_{Inf}$ | h*ng/mL | 584 |
| MRT | h | 1.93 |
| F | % | 111 |

TABLE 28

Dog PO PK results for Compound 03-3.

| | PO Dose | |
|---|---|---|
| PK parameters | Unit | 2.5 mg/kg |
| $T_{max}$ | h | 0.5 |
| $C_{max}$ | ng/mL | 413 |

TABLE 28-continued

Dog PO PK results for Compound 03-3.

| | PO Dose | |
|---|---|---|
| PK parameters | Unit | 2.5 mg/kg |
| $AUC_{Inf}$ | h*ng/mL | 1591 |
| MRT | h | 3.19 |
| F | % | 194 |

TABLE 29

Dog PO PK results for Compound 03-5.

| | PO Dose | |
|---|---|---|
| PK parameters | Unit | 0.3 mg/kg |
| $T_{max}$ | h | 0.42 |
| $C_{max}$ | ng/mL | 43.2 |
| $AUC_{Inf}$ | h*ng/mL | 55.4 |
| MRT | h | 1.22 |
| F | % | 72 |

TABLE 30

Dog PO PK results for Compound 03-5.

| | PO Dose | |
|---|---|---|
| PK parameters | Unit | 1.0 mg/kg |
| $T_{max}$ | h | 0.33 |
| $C_{max}$ | ng/mL | 164 |
| $AUC_{Inf}$ | h*ng/mL | 273 |
| MRT | h | 1.37 |
| F | % | 70 |

TABLE 31

Dog PO PK results for Compound 03-115.

| | PO Dose | |
|---|---|---|
| PK parameters | Unit | 0.5 mg/kg |
| $T_{max}$ | h | 0.5 |
| $C_{max}$ | ng/mL | 72.3 |
| $AUC_{Inf}$ | h*ng/mL | 132 |
| MRT | h | 1.82 |
| F | % | 53 |

TABLE 32

Dog PO PK results for Compound 03-115.

| | PO Dose | |
|---|---|---|
| PK parameters | Unit | 1.5 mg/kg |
| $T_{max}$ | h | 0.33 |
| $C_{max}$ | ng/mL | 387 |
| $AUC_{Inf}$ | h*ng/mL | 537 |
| MRT | h | 1.69 |
| F | % | 71 |

Example 7: Monkey Pharmacokinetic Studies

Monkey pharmacokinetics studies of exemplary compounds 03-3, 03-5, and 03-115 were conducted substantially similarly to the rat pharmacokinetic studies, instead using male Non-Naïve Cynomolgus Monkeys. Animals for PO studies were food fasted overnight prior to dosing and were fed approximately 2 hours after dosing. Animals for IV studies had free access to food and water. Blood samples were collected through venipuncture of peripheral veins except the dosing vein.

Exemplar PK results for PO dosing are summarized in Tables 33-35, below.

Figure 10:
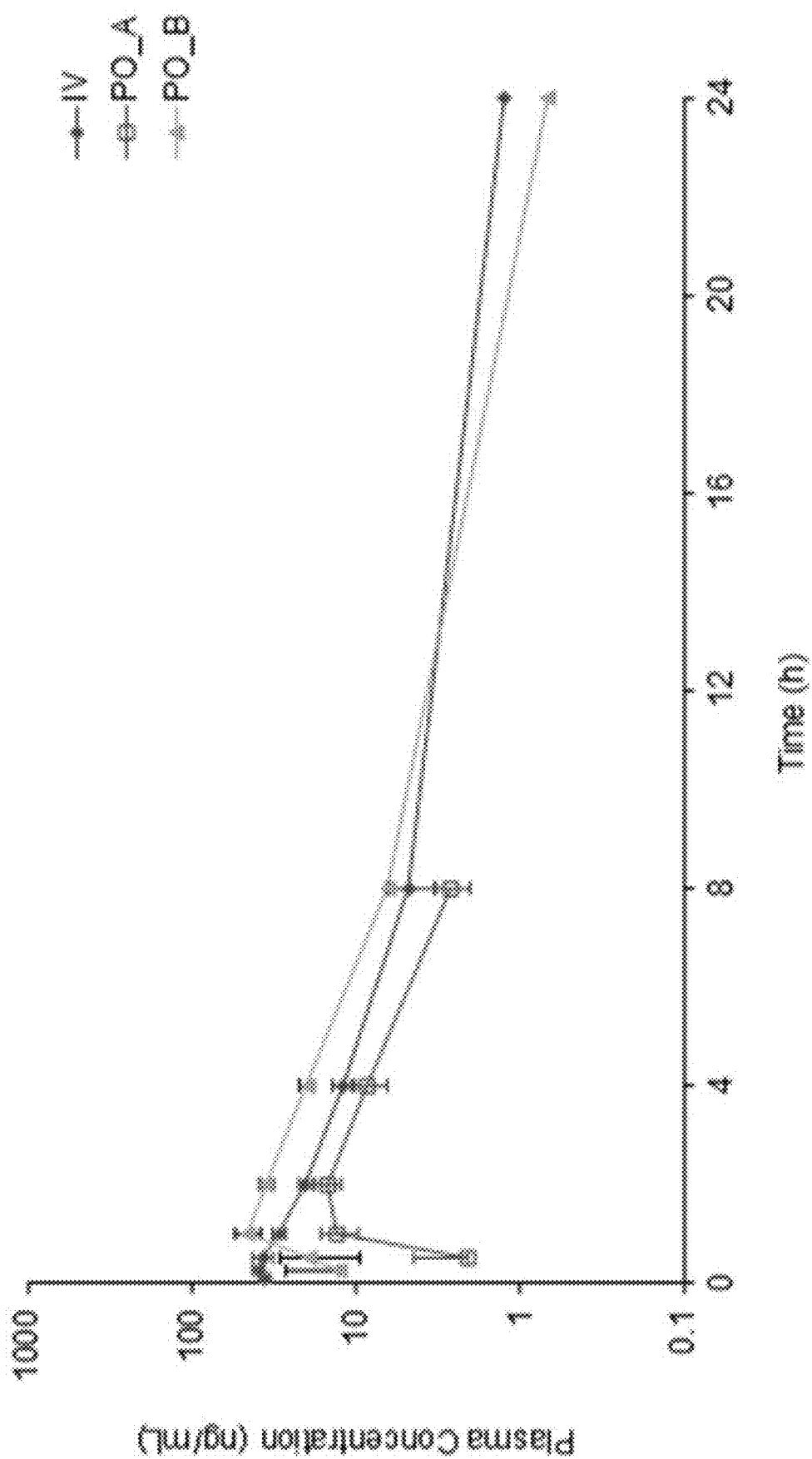
FIG. 10 summarizes the pharmacokinetic properties of Compound 03-3 in male Cynomolgus monkeys following oral (0.1 and 0.3 mg/kg; "PO_A" and "PO_B", respectively) and intravenous (0.1 mg/kg) administration.
Figure 11:
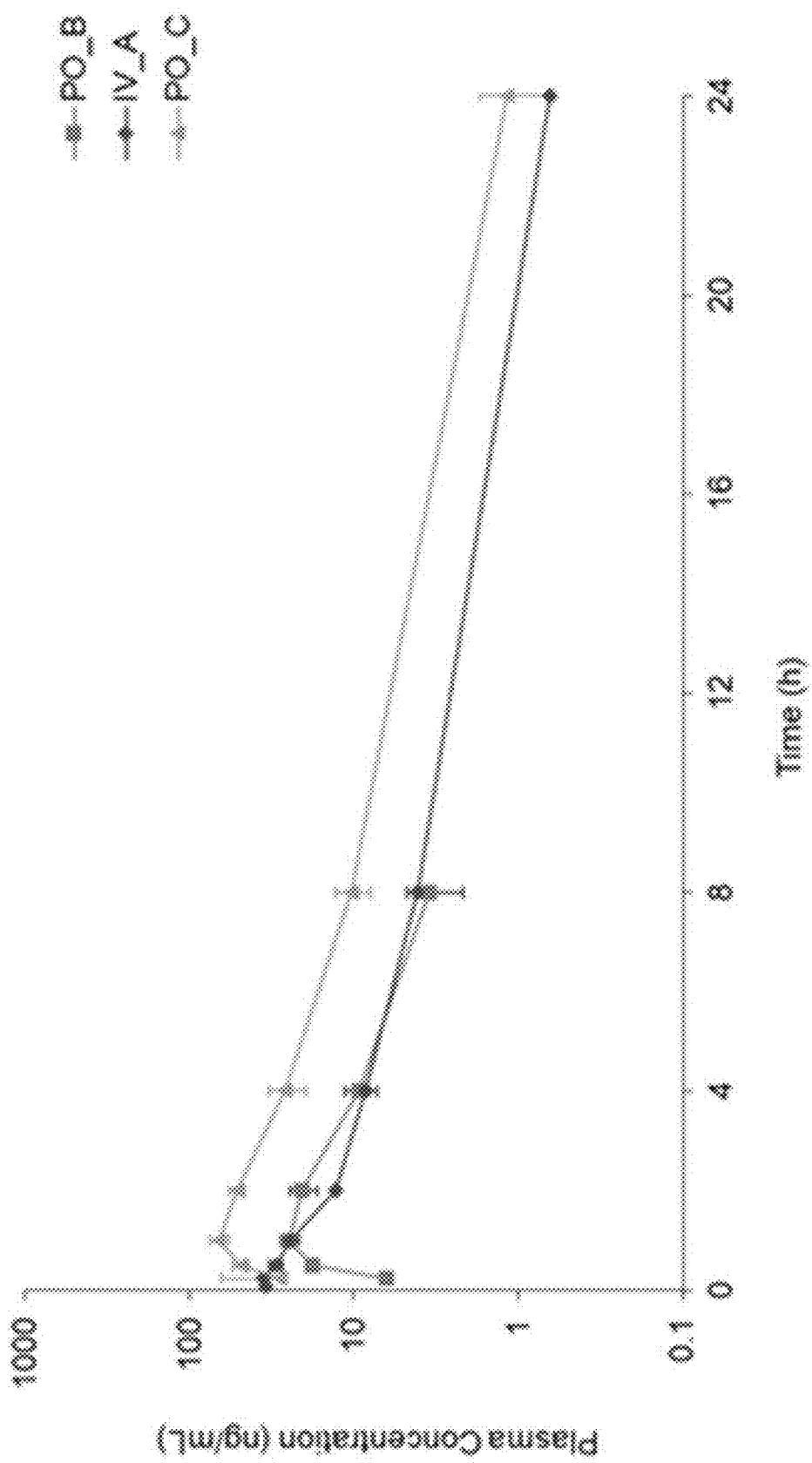
FIG. 11 summarizes the pharmacokinetic properties of Compound 03-5 in male Cynomolgus monkeys following oral (0.1 and 0.3 mg/kg; "PO_B" and "PO_C", respectively) and intra venous (0.1 mg/kg) administration.
Figure 15:
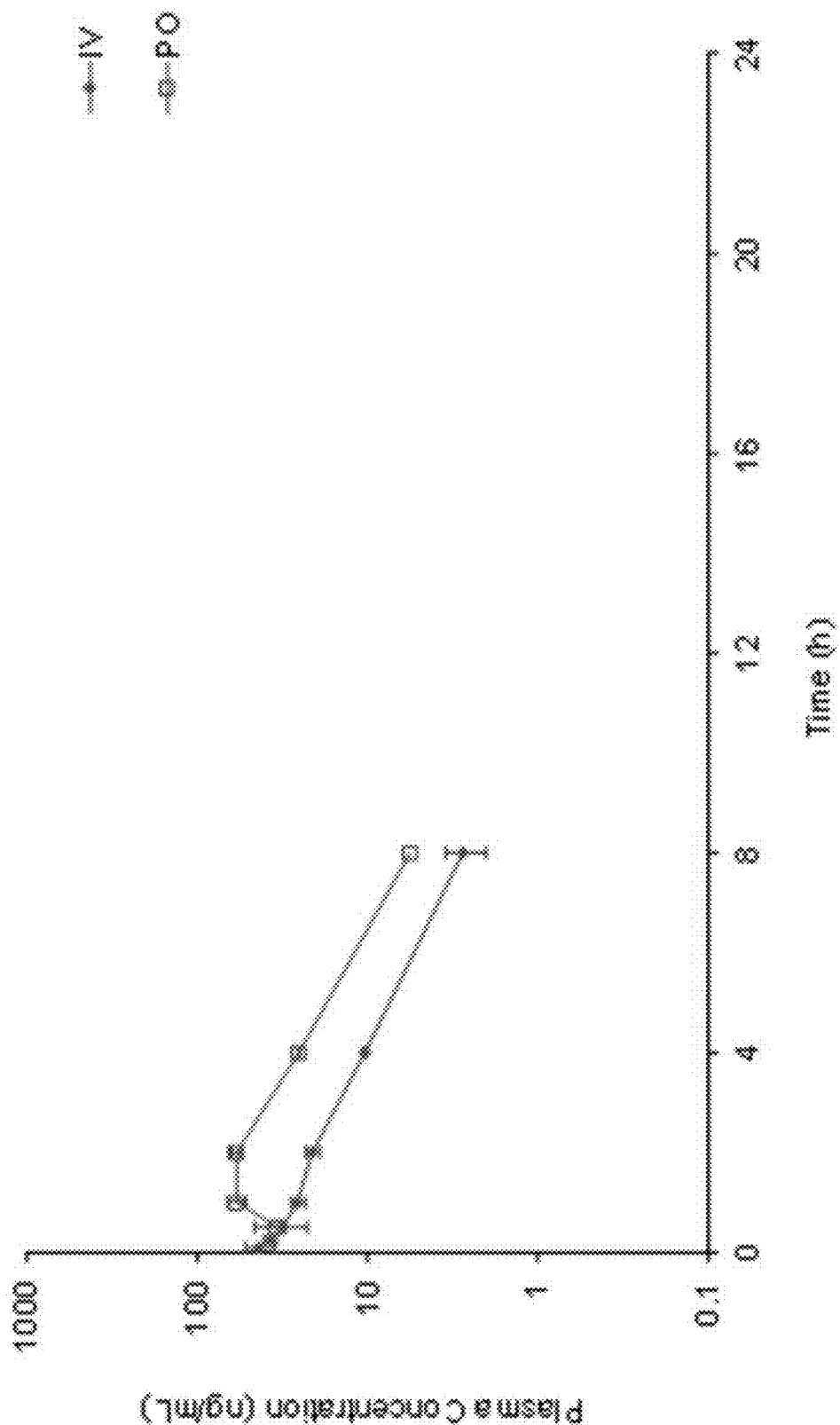
FIG. 15 summarizes the pharmacokinetic properties of Compound 03-115 in male Cynomolgus monkeys following oral (0.3 mg/kg) and intravenous (0.1 mg/kg) administration.

PK results in male Cynomolgus monkeys are further summarized in FIGS. 10-11, and 15.

It has been surprisingly found that compounds of the present disclosure have excellent absorption and overall exposure characteristics. Furthermore, it has been surprisingly found that the oral bioavailability of compounds of the present near their respective intravenous bioavailabilities.

TABLE 33

Monkey PO PK results for Compound 03-3.

| PK parameters | Unit | PO Dose 0.3 mg/kg |
|---|---|---|
| $T_{1/2}$ | h | 4.32 |
| $T_{max}$ | h | 1.00 |
| $C_{max}$ | ng/mL | 46.6 |
| $AUC_{last}$ | h*ng/mL | 228 |
| $AUC_{Inf}$ | h*ng/mL | 232 |
| $AUC_{\_\%\ Extrap\_}obs$ | % | 1.87 |
| $MRT_{Inf\_}obs$ | h | 4.99 |
| $AUC_{last}/D$ | h*mg/mL | 761 |
| F | % | 44.6 |

TABLE 34

Monkey PO PK results for Compound 03-5.

| PK parameters | Unit | PO Dose 0.3 mg/kg |
|---|---|---|
| $T_{1/2}$ | h | 4.53 |
| $T_{max}$ | h | 1.00 |
| $C_{max}$ | ng/mL | 66.2 |
| $AUC_{last}$ | h*ng/mL | 343 |
| $AUC_{Inf}$ | h*ng/mL | 351 |
| $AUC_{\_\%\ Extrap\_}obs$ | % | 2.13 |
| $MRT_{Inf\_}obs$ | h | 5.11 |
| $AUC_{last}/D$ | h*mg/mL | 1144 |
| F | % | 88.3 |

TABLE 35

Monkey PO PK results for Compound 03-115.

| PK parameters | Unit | PO Dose 0.3 mg/kg |
|---|---|---|
| $T_{max}$ | h | 1.17 |
| $C_{max}$ | ng/mL | 67 |
| $AUC_{Inf}$ | h*ng/mL | 261 |
| $MRT_{Inf\_}obs$ | h | 3.46 |
| F | % | 71 |

Example 8: Evaluation of Additional Synthesized Adrenergic Receptor Agonists

Potency of the following additional compounds was measured using methods described in Example 2. The potency data for select compounds is summarized in Table 36A ($EC_{50}$) and Table 36B ($pEC_{50}$), below.

TABLE 36A

The pharmacological data of certain additional chemical compounds disclosed herein.

| Compound | Average $EC_{50}$ [Receptor subtype: B1-AR; Cell type: CHO-K] | Average $EC_{50}$ [Receptor subtype: B2-AR; Cell type: CHO-K] | Average $EC_{50}$ [Receptor subtype: Endogenous; Cell type: 1321N1] | Average $EC_{50}$ [Receptor subtype: B3-AR; Cell type: CHO-K1] |
|---|---|---|---|---|
| 03-5 | C | A | B | C |
| 03-6 | B | B | — | — |
| 03-7 | D | C | — | — |
| 03-8 | D | C | — | — |
| 03-9 | B | A | — | — |
| 03-10 | B | A | B | D |
| 03-11 | B | A | — | — |
| 03-12 | D | C | — | — |
| 03-13 | D | D | — | — |
| 03-14 | B | B | — | — |
| 03-15 | A | A | — | — |
| 03-16 | C | B | — | — |
| 03-17 | D | D | — | — |
| 03-18 | D | — | — | — |
| 03-19 | C | B | — | — |
| 03-20 | D | C | — | — |
| 03-21 | C | B | — | — |
| 03-22 | D | D | — | — |
| 03-23 | C | C | — | — |
| 03-25 | D | D | — | — |
| 03-28 | B | A | — | — |
| 03-29 | A | A | A | D |
| 03-30 | C | B | — | — |
| 03-31 | — | D | — | — |
| 03-32 | A | B | — | — |
| 03-33 | A | A | — | — |
| 03-34 | D | D | — | — |
| 03-35 | A | B | — | — |
| 03-36 | D | D | — | — |
| 03-37 | B | A | — | — |
| 03-38 | C | B | C | D |
| 03-43 | D | D | — | — |
| 03-44 | B | B | C | D |
| 03-45 | B | C | A | A |
| 03-47 | D | D | — | — |
| 03-48 | D | D | — | — |
| 03-49 | D | C | D | D |
| 03-51 | D | D | — | — |
| 03-53 | D | B | C | D |
| 03-54 | C | B | C | — |
| 03-56 | — | D | — | — |
| 03-57 | C | B | C | D |
| 03-58 | B | B | B | D |
| 03-59 | A | A | A | C |

TABLE 36A-continued

The pharmacological data of certain additional chemical compounds disclosed herein.

| Compound | Average EC$_{50}$ [Receptor subtype: B1-AR; Cell type: CHO-K] | Average EC$_{50}$ [Receptor subtype: B2-AR; Cell type: CHO-K] | Average EC$_{50}$ [Receptor subtype: Endogenous; Cell type: 1321N1] | Average EC$_{50}$ [Receptor subtype: B3-AR; Cell type: CHO-K1] |
|---|---|---|---|---|
| 03-60 | D | D | — | — |
| 03-61 | — | D | — | — |
| 03-112 | — | D | — | — |
| 03-113 | — | D | — | — |
| 03-114 | C | B | — | — |
| 03-115 | D | B | — | — |
| 03-116 | — | D | — | — |
| 03-118 | — | C | — | — |
| 03-119 | C | — | — | — |
| 03-121 | B | A | — | — |
| 03-122 | D | C | — | — |
| 03-123 | A | A | — | — |
| 03-124 | C | B | — | — |
| 03-125 | C | C | — | — |
| 03-126 | B | B | — | — |
| 03-127 | B | B | — | — |
| 03-128 | D | D | — | — |
| 03-129 | B | A | — | — |
| 03-130 | C | B | — | — |
| 03-131 | B | A | — | — |
| 03-132 | D | — | — | — |
| 03-133 | C | A | — | — |
| 03-135 | C | A | — | — |
| 03-136 | — | B | — | — |
| 03-137 | C | A | — | — |
| 03-138 | D | — | — | — |
| 03-139 | D | — | — | — |
| 03-141 | C | A | — | — |
| 03-142 | D | C | — | — |
| 03-143 | D | — | — | — |
| 03-145 | B | A | — | — |
| 03-146 | C | — | — | — |
| 03-147 | B | A | — | — |
| 03-148 | C | C | — | — |
| 03-149 | C | A | — | — |
| 03-150 | D | — | — | — |
| 03-151 | B | A | — | — |
| 03-152 | D | C | — | — |
| 03-153 | B | A | — | — |
| 03-154 | D | D | — | — |
| 03-155 | B | A | — | — |
| 03-156 | D | B | — | — |
| 03-157 | A | A | — | — |
| 03-158 | D | B | — | — |
| 03-159 | B | — | — | — |
| 03-160 | C | — | — | — |
| 03-161 | A | A | — | — |
| 03-162 | D | B | — | — |
| 03-163 | A | A | — | — |
| 03-164 | C | A | — | — |
| 03-165 | A | A | — | — |
| 03-166 | C | C | — | — |
| 03-167 | A | A | — | — |
| 03-168 | B | B | — | — |
| 03-169 | B | A | — | — |
| 03-170 | D | C | — | — |
| 03-171 | — | D | — | — |
| 03-172 | D | D | — | — |
| 03-173 | C | A | — | — |
| 03-175 | B | A | — | — |
| 03-176 | D | C | — | — |
| 03-177 | B | A | — | — |
| 03-178 | — | C | — | — |
| 03-179 | C | A | — | — |
| 03-180 | — | C | — | — |
| 03-181 | D | C | — | — |
| 03-182 | B | A | — | — |
| 03-183 | D | C | — | — |
| 03-184 | B | B | — | — |
| 03-185 | D | D | — | — |
| 03-186 | D | C | — | — |
| 03-187 | — | D | — | — |

EC$_{50}$ (nM): A < 10 nM; B = 10-100 nM; C = 100 nM-1 μM; D > 1 μM

TABLE 36B

The pharmacological data of certain additional chemical compounds disclosed herein.

| Compound | Average pEC$_{50}$ [Receptor subtype: B1-AR; Cell type: CHO-K1 (HitHunter)] | Average pEC$_{50}$ [Receptor subtype: B2-AR; Cell type: CHO-K1 (HitHunter)] | Average pEC$_{50}$ [Receptor subtype: Endogenous; Cell type: 1321N1] | Average pEC$_{50}$ [Receptor subtype: B3-AR; Cell type: CHO-K1] |
|---|---|---|---|---|
| 03-5 | C | B-A | C-B | D |
| 03-6 | B | B | C | — |
| 03-7 | D | C | — | — |
| 03-8 | D | C | D | D |
| 03-9 | B | A | B | C |
| 03-10 | B | A | B | D |
| 03-11 | B | A | C | D |
| 03-12 | D | C | — | — |
| 03-13 | D | D | — | — |
| 03-14 | B | B | C | D |
| 03-15 | A | A | A | C |
| 03-16 | C | B | — | — |
| 03-17 | D | D | — | — |
| 03-18 | D | — | — | — |
| 03-19 | C | B | C | D |
| 03-20 | D | C | — | — |
| 03-21 | C | B | B | D |
| 03-22 | D | D | — | — |
| 03-23 | C | C | — | — |
| 03-25 | D | D | — | — |
| 03-28 | B | A | — | — |
| 03-29 | A | A | A | D |
| 03-30 | C | B | — | — |
| 03-31 | — | D | — | — |
| 03-32 | A | B | — | — |
| 03-33 | A | A | B | D |
| 03-34 | D | D | — | — |
| 03-35 | A | B | B | D |
| 03-36 | D | D | — | — |
| 03-37 | B | A | A | C |
| 03-38 | C | B | C | D |
| 03-43 | D | C | — | — |
| 03-44 | B | B | C | D |
| 03-45 | B | C | — | — |
| 03-47 | D | D | — | — |
| 03-48 | D | C-D | — | — |
| 03-49 | D | — | — | — |
| 03-51 | D | D | — | — |
| 03-52 | D | C | D | D |
| 03-53 | D | B | C | D |
| 03-54 | C | B | C | — |
| 03-56 | — | D | — | — |
| 03-57 | C | B | C | D |
| 03-58 | B | B | B | D |
| 03-59 | A | A | A | C |
| 03-60 | D | D | — | — |
| 03-61 | — | D | — | — |

TABLE 36B-continued

The pharmacological data of certain additional chemical compounds disclosed herein.

| Compound | Average pEC$_{50}$ [Receptor subtype: B1-AR; Cell type: CHO-K1 (HitHunter)] | Average pEC$_{50}$ [Receptor subtype: B2-AR; Cell type: CHO-K1 (HitHunter)] | Average pEC$_{50}$ [Receptor subtype: Endogenous; Cell type: 1321N1] | Average pEC$_{50}$ [Receptor subtype: B3-AR; Cell type: CHO-K1] |
|---|---|---|---|---|
| 03-62 | — | D | — | — |
| 03-63 | D | C | D | — |
| 03-64 | D | C | C | — |
| 03-65 | D | B | — | — |
| 03-66 | B | A | C | — |
| 03-67 | C | A | B | — |
| 03-68 | C | B | — | — |
| 03-70 | C | B | B | — |
| 03-71 | C | B | B | — |
| 03-72 | B | A | B | — |
| 03-73 | — | D | — | — |
| 03-74 | D | D | — | — |
| 03-75 | D | D | — | — |
| 03-76 | C | C | — | — |
| 03-77 | — | D | — | — |
| 03-78 | A | — | — | — |
| 03-79 | — | D | — | — |
| 03-80 | D | B | C | — |
| 03-83 | D | C | — | — |
| 03-84 | — | D | — | — |
| 03-85 | D | C | — | — |
| 03-86 | D | C | — | — |
| 03-89 | D | C | D | — |
| 03-90 | D | D | — | — |
| 03-92 | D | D | — | — |
| 03-95 | A | A | A | — |
| 03-98 | D | D | — | — |
| 03-101 | D | B | C | — |
| 03-102 | C | B | B | — |
| 03-104 | C | C | C | — |
| 03-108 | — | D | — | — |
| 03-109 | C | C | — | — |
| 03-110 | D | D | — | — |
| 03-111 | D | B | C | — |
| 03-112 | — | D | — | — |
| 03-113 | — | D | — | — |
| 03-114 | C | B | — | — |
| 03-115 | C-D | B | C | D |
| 03-116 | — | D | — | — |
| 03-118 | — | C | — | — |
| 03-119 | C | — | — | — |
| 03-121 | C | A | A | — |
| 03-122 | D | C | — | — |
| 03-123 | A | A | A | — |
| 03-124 | C | B | — | — |
| 03-125 | C | C | — | — |
| 03-126 | B | B | B | C |
| 03-127 | B | B | B | D |
| 03-128 | D | D | — | — |
| 03-129 | B | A | — | — |
| 03-130 | C | B | — | — |
| 03-131 | B | A | — | — |
| 03-132 | D | — | — | — |
| 03-133 | C | A | — | — |
| 03-135 | C | A | — | — |
| 03-136 | — | B | — | — |
| 03-137 | C | A | — | — |
| 03-138 | D | — | — | — |
| 03-139 | D | — | — | — |
| 03-141 | B | A | B | D |
| 03-142 | D | C | D | — |
| 03-143 | D | C | — | — |
| 03-145 | B | A | — | — |
| 03-146 | C | — | — | — |
| 03-147 | B | A | — | — |
| 03-148 | C | C | — | — |
| 03-149 | C | A | — | — |
| 03-150 | D | — | — | — |
| 03-151 | B | A | — | — |
| 03-152 | D | B | — | — |
| 03-153 | B | A | B | — |
| 03-154 | D | D | — | — |
| 03-155 | B | A | — | — |
| 03-156 | D | B | — | — |
| 03-157 | A | A | — | — |
| 03-158 | D | B | — | — |
| 03-159 | B | — | — | — |
| 03-160 | — | C | — | — |
| 03-161 | A | A | A | C |
| 03-162 | D | B | C | — |
| 03-167 | A | A | A | D |
| 03-168 | B | B | C | C |
| 03-169 | B | A | C | D |
| 03-170 | D | C | — | — |
| 03-173 | C | A | A | D |
| 03-175 | B | A | A | D |
| 03-176 | D | C | — | — |
| 03-177 | B | A | A | C |
| 03-178 | — | C | — | — |
| 03-179 | C | A | A | C |
| 03-180 | — | C | — | — |
| 03-181 | D | C | C | — |
| 03-182 | B | A | A | C |
| 03-183 | D | C | — | — |
| 03-184 | B | B | B | C |
| 03-185 | D | D | — | — |
| 03-186 | D | C | — | — |
| 03-189 | B | A | B | — |
| 03-190 | B | A | A | — |
| 03-191 | B | A | A | — |
| 03-192 | B | A | B | — |
| 03-193 | A | A | A | — |
| 03-194 | — | D | — | — |
| 03-195 | C | B | B | — |
| 03-196 | B | A | — | — |
| 03-197 | B | A | A | — |
| 03-198 | D | B | — | — |
| 03-200 | B | A | — | — |
| 03-206 | A | A | — | — |
| 03-207 | A | A | — | — |
| 03-209 | A | A | A | — |
| 03-211 | C | C | — | — |
| 03-212 | D | C | — | — |
| 03-213 | D | B | — | — |
| 03-214 | C | A | — | — |
| 03-215 | C | A | B | — |
| 03-216 | D | B | — | — |
| 03-218 | — | D | — | — |
| 03-219 | C | C | D | C |
| 03-220 | D | B | — | — |
| 03-221 | B | A | — | — |
| 03-222 | — | D | — | — |
| 03-224 | — | C | — | — |
| 03-225 | C | C | — | — |
| 03-226 | D | C | — | — |
| 03-227 | — | D | — | — |
| 03-228 | B | A | A | — |
| 03-229 | D | D | — | — |
| 03-230 | B | B | C | — |
| 03-231 | D | B | — | — |
| 03-232 | B | B | — | — |
| 03-234 | B | B | — | — |
| 03-235 | D | D | — | — |
| 03-236 | — | C | — | — |
| 03-237 | B | A | A | — |
| 03-238 | C | B | C | — |

TABLE 36B-continued

The pharmacological data of certain additional chemical compounds disclosed herein.

| Compound | Average pEC$_{50}$ [Receptor subtype: B1-AR; Cell type: CHO-K1 (HitHunter)] | Average pEC$_{50}$ [Receptor subtype: B2-AR; Cell type: CHO-K1 (HitHunter)] | Average pEC$_{50}$ [Receptor subtype: Endogenous; Cell type: 1321N1] | Average pEC$_{50}$ [Receptor subtype: B3-AR; Cell type: CHO-K1] |
|---|---|---|---|---|
| 03-239 | C | B | — | — |
| 03-240 | — | D | — | — |
| 03-241 | D | D | — | — |
| 03-242 | — | D | — | — |
| 03-243 | D | B | C | — |
| 03-244 | C | B | — | — |
| 03-245 | — | D | — | — |
| 03-246 | D | D | — | — |
| 03-247 | D | D | — | — |
| 03-248 | B | B | B | — |
| 03-249 | A | A | A | — |
| 03-250 | D | C | — | — |
| 03-252 | D | D | — | — |
| 03-253 | D | B | C | — |
| 03-254 | D | C | — | — |
| 03-257 | B | A | A | — |
| 03-258 | C | B | — | — |
| 03-259 | B | A | — | — |
| 03-260 | D | A | — | — |
| 03-261 | D | C | — | — |
| 03-262 | B | A | — | — |
| 03-263 | B | A | — | — |
| 03-264 | B | A | — | — |
| 03-265 | B | A | — | — |
| 03-266 | A | A | — | — |
| 03-267 | C | B | C | — |
| 03-268 | B | A | — | — |
| 03-269 | B | A | — | — |
| 03-270 | D | B | — | — |
| 03-271 | C | B | — | — |
| 03-272 | A | A | A | — |
| 03-273 | D | C | — | — |
| 03-274 | D | B | — | — |
| 03-275 | D | B | — | — |
| 03-276 | C | B | — | — |
| 03-277 | D | A | — | — |
| 03-278 | C | A | — | — |
| 03-279 | D | C | — | — |
| 03-280 | D | D | — | — | pEC$_{50}$: A > 8; B = 8-7; C = <7-6; D < 6

Those skilled in the art will recognize, or be able to ascertain, using no more than routine experimentation, numerous equivalents to the specific compositions and procedures described herein. Such equivalents are considered to be within the scope of this disclosure, and are covered by the following claims.

In addition to the various embodiments described in the specification above, the following additional embodiments are contemplated herein.

1. A compound according to Formula (I)

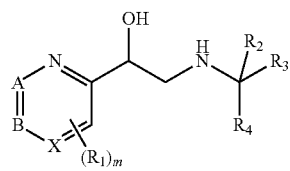

Formula (I)

or an optically pure stereoisomer, pharmaceutically acceptable salt, solvate, or prodrug thereof, wherein each A, B, and X is independently a nitrogen or carbon;

each $R_1$ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C═O)-alkyl, unsubstituted or substituted —(C═O)-cycloalkyl, unsubstituted or substituted —(C═O)-aryl, unsubstituted or substituted —(C═O)-heteroaryl, unsubstituted or substituted aryl, and unsubstituted or substituted heteroaryl;

m is an integer selected from 0 to 4;

$R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

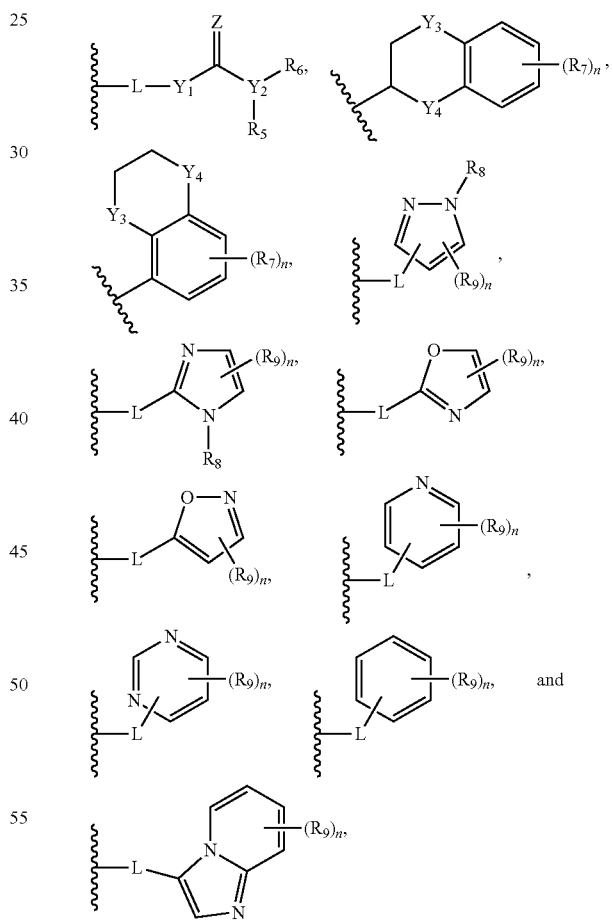

or $R_2$ and $R_3$ together with the carbon form an unsubstituted or substituted 3-7 membered cycloalkyl or heterocycle ring;

L is a C1-C5 alkyl linker optionally substituted;

each $Y_1$, $Y_2$, $Y_3$, and $Y_4$ is independently a covalent bond, a carbon, an oxygen, or a nitrogen, optionally substituted with hydrogen, unsubstituted or substituted alkyl, or unsubstituted or substituted cyclo alkyl;

Z is O or S;

R₅ and R₆ are independently selected from hydrogen, unsubstituted or substituted alkyl, or R₅ and R₆ are cyclically linked and together with Y₂ to form an optionally substituted cycloalkyl or heterocycle;

each R₇ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl;

n is an integer selected from 0 to 4;

R₈ is selected from the group consisting of hydrogen, cyano, unsubstituted or substituted alkyl, and unsubstituted or substituted aryl; and R₉ is selected from the group consisting of hydrogen, halogen, cyano, unsubstituted or substituted alkyl, unsubstituted or substituted alkoxy, and unsubstituted or substituted amino.

2. A compound according to Formula (II)

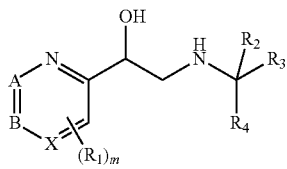

Formula (II)

or an optically pure stereoisomer, pharmaceutically acceptable salt, solvate, or prodrug thereof, wherein each A, B, and X is independently a nitrogen or carbon;

each R₁ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, and unsubstituted or substituted heteroaryl;

m is an integer selected from 0 to 4;

R₂, R₃, and R₄ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl,

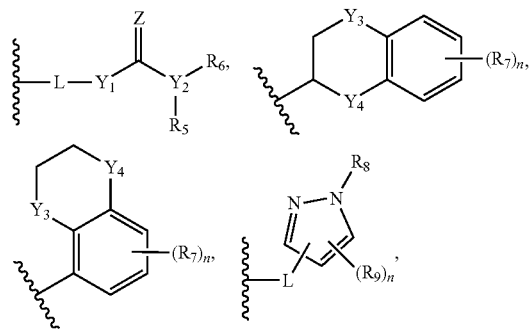

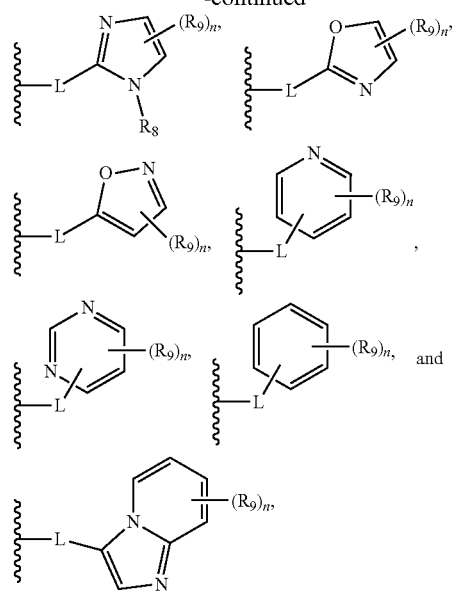

or R₂ and R₃ together with the carbon form an unsubstituted or substituted 3-7 membered cycloalkyl or heterocycle ring;

L is a C1-C5 alkyl linker optionally substituted;

each Y₁, Y₂, Y₃, and Y₄ is independently a covalent bond, a carbon, an oxygen, or a nitrogen, optionally substituted with hydrogen, unsubstituted or substituted alkyl, or unsubstituted or substituted cyclo alkyl;

Z is O or S;

R₅ and R₆ are independently selected from hydrogen, unsubstituted or substituted alkyl, or R₅ and R₆ are cyclically linked and together with Y₂ to form an optionally substituted cycloalkyl or heterocycle;

each R₇ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl;

n is an integer selected from 0 to 4;

R₈ is selected from the group consisting of hydrogen, cyano, unsubstituted or substituted alkyl, and unsubstituted or substituted aryl; and R₉ is selected from the group consisting of hydrogen, halogen, cyano, unsubstituted or substituted alkyl, unsubstituted or substituted alkoxy, and unsubstituted or substituted amino.

3. A compound according to Formula (III)

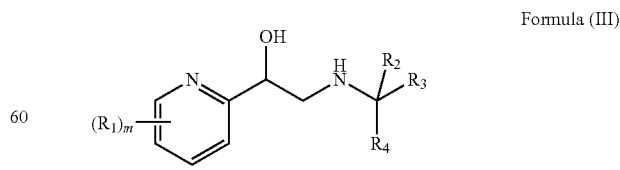

Formula (III)

or an optically pure stereoisomer, pharmaceutically acceptable salt, solvate, or prodrug thereof, wherein each R₁ is independently selected from the group consisting of hydrogen, halogen, cyano, nitro, pentafluorosulfanyl, unsubstituted or substituted sulfonyl, substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted —(C=O)-alkyl, unsubstituted or substituted —(C=O)-cycloalkyl, unsubstituted or substituted —(C=O)-aryl, unsubstituted or substituted —(C=O)-heteroaryl, unsubstituted or substituted aryl, and unsubstituted or substituted heteroaryl;

m is an integer selected from 0 to 4;

$R_2$, $R_3$, and $R_4$ are independently selected from the group consisting of H, halogen, hydroxyl, cyano, nitro, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, unsubstituted or substituted heteroaryl, each $R_7$ is independently selected from the group consisting of hydrogen, halogen, cyano, nitro, hydroxyl, unsubstituted or substituted amino, unsubstituted or substituted alkyl, unsubstituted or substituted alkoxy, unsubstituted or substituted alkenyl, unsubstituted or substituted alkynyl, unsubstituted or substituted cycloalkyl, unsubstituted or substituted aryl, and unsubstituted or substituted heteroaryl;

n is an integer selected from 0 to 4;

$R_8$ is selected from the group consisting of hydrogen, cyano, unsubstituted or substituted alkyl, and unsubstituted or substituted aryl; and $R_9$ is selected from the group consisting of hydrogen, halogen, cyano, unsubstituted or substituted alkyl, unsubstituted or substituted alkoxy, and unsubstituted or substituted amino.

4. The compound of embodiment 1 with the following structure

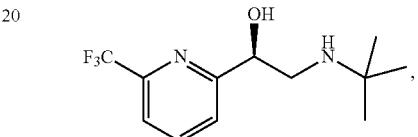

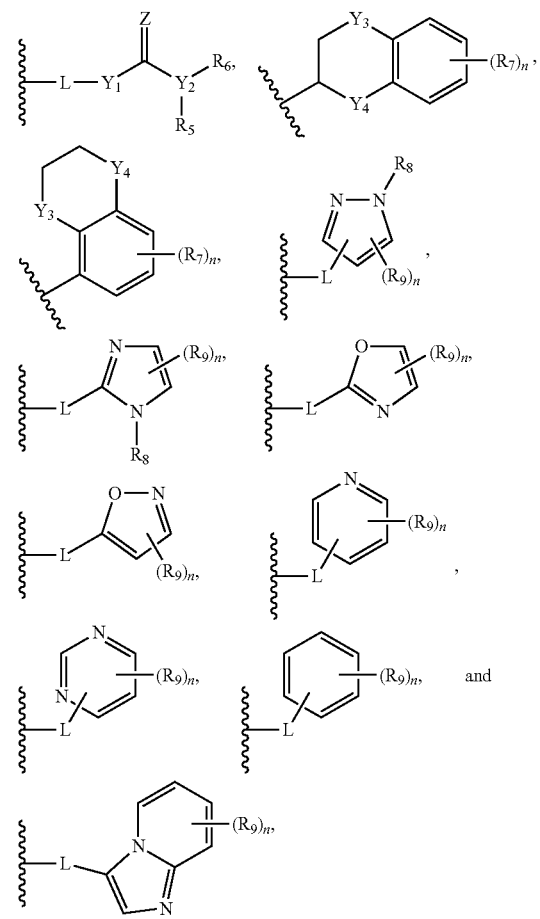

or a pharmaceutically acceptable salt thereof.

5. The compound of any one of embodiments 1-4 wherein said compound is an agonist, partial agonist or antagonist of an adrenergic receptor.

6. The compound of any one of embodiments 1-4 wherein said compound is a β1-adrenergic receptor agonist, β2-adrenertic receptor agonist or non-selective β1/β2-adrenergic receptor agonist.

7. The compound of any one of embodiments 1-4 wherein said compound is a β1-adrenergic receptor agonist.

8. The compound of any one of embodiments 1-4 wherein said compound is a β2-adrenergic receptor agonist.

9. The compound of any one of embodiments 1-4 wherein said compound is a non-selective β1/β2-adrenergic agonist.

10. A pharmaceutical composition comprising the compound of any one of embodiments 1-9 and a pharmaceutically acceptable excipient.

11. A method of treating a subject with a disease comprising administering to the subject a therapeutically effective amount of a compound according to any one of embodiments 1-9.

12. A method of treating a subject with a disease comprising administering to the subject a therapeutically effective amount of a compound according to any one of embodiments 1-9, thereby treating the subject.

13. A method of treating a subject with a disease associated with an adrenergic receptor comprising administering to the subject a therapeutically effective amount of the compound according to any one of embodiments 1-9.

14. The method of any one of embodiments 11-13, wherein the disease is a neurodegenerative disease.

15. The method of embodiment 14, wherein the disease is one or more selected from the group consisting of MCI (mild cognitive impairment), aMCI (amnestic MCI), Vascular Dementia, Mixed Dementia, FTD (fronto-temporal dementia; Pick's disease), HD (Huntington disease), Rett Syndrome, PSP (progressive supranuclear palsy), CBD (corticobasal degeneration), SCA (spinocerebellar ataxia), MSA (Multiple system atrophy), SDS (Shy-Drager syndrome), olivopontocerebellar atrophy, TBI (traumatic brain injury), CTE (chronic traumatic encephalopathy), stroke, WKS or $R_2$ and $R_3$ together with the carbon form an unsubstituted or substituted 3-7 membered cycloalkyl or heterocycle ring;

L is a C1-C5 alkyl linker optionally substituted;

each $X_1$, $X_2$, $X_3$, and $X_4$ is independently a covalent bond, a carbon, an oxygen, or a nitrogen, optionally substituted with hydrogen, unsubstituted or substituted alkyl, or unsubstituted or substituted cyclo alkyl;

Y is O or S;

$R_5$ and $R_6$ are independently selected from hydrogen, unsubstituted or substituted alkyl, or $R_5$ and $R_6$ are cyclically linked and together with $Y_2$ to form an optionally substituted cycloalkyl or heterocycle;

(Wernicke-Korsakoff syndrome; alcoholic dementia & thiamine deficiency), normal pressure hydrocephalus, hypersomnia/narcolepsy, ASD (autistic spectrum disorders), FXS (fragile X syndrome), TSC (tuberous sclerosis complex), prion-related diseases (CJD etc.), depressive disorders, DLB (dementia with Lewy bodies), PD (Parkinson's disease), PDD (PD dementia), ADHD (attention deficit hyperactivity disorder), Alzheimer's disease (AD), early AD, and Down Syndrome (DS).

16. The method of any one of embodiments 11-15, wherein the subject is a human.

17. The method of any one of embodiments 11-16, wherein the compound is administered to the subject through an oral, enteral, topical, inhalation, transmucosal, intravenous, intramuscular, intraperitoneal, subcutaneous, intranasal, epidural, intracerebral, intracerebroventricular, epicutaneous, extra-amniotic, intra-arterial, intra-articular, intracardiac, intracavernous, intradermal, intralesional, intraocular, intraosseous infusion, intraperitoneal, intrathecal, intrauterine, intravaginal, intravesical, intravitreal, transdermal, perivascular, buccal, vaginal, sublingual, or rectal route.

18. A compound according to Formula (XXII'):

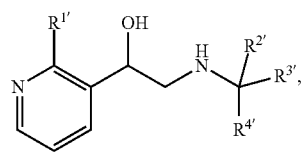

Formula (XXII')

or a pharmaceutically acceptable salt thereof,
wherein:
$R^{1'}$ is halogen, —R', —CN, or —NO$_2$;
each R' is an optionally substituted $C_{1-6}$ aliphatic; and $R^{2'}$, $R^{3'}$, and $R^{4'}$ are each independently halogen, —R', —CN, —NO$_2$, —OR', or —NR'$_2$, or
$R^{2'}$ and $R^{3'}$ together with the carbon form an optionally substituted 3-7 membered cycloalkyl or heterocycle ring.

19. A compound of embodiment 18, wherein the carbon attached to the OH group has an (R) configuration.

20. A compound of either of embodiments 18-19, wherein $R^{1'}$ is methyl.

21. A compound of any of embodiments 18-20, wherein $R^{2'}$ is $C_{1-6}$ aliphatic.

22. A compound of any of embodiments 18-21, wherein $R^{2'}$ is methyl.

23. A compound of any of embodiments 18-22, wherein $R^{3'}$ is $C_{1-6}$ aliphatic.

24. A compound of any of embodiments 18-23, wherein $R^{3'}$ is methyl.

25. A compound of any of embodiments 18-22, wherein $R^{4'}$ is $C_{1-6}$ aliphatic.

26. A compound of any of embodiments 18-23, wherein $R^{4'}$ is methyl.

27. A compound according to Formula (XVIII'):

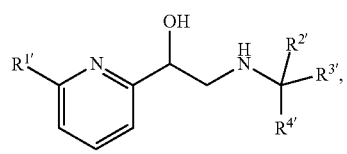

Formula (XVIII')

or a pharmaceutically acceptable salt thereof,
wherein:
$R^{1'}$ is halogen, —R', —CN, or —NO$_2$;
each R' is an optionally substituted $C_{1-6}$ aliphatic; and
$R^{2'}$, $R^{3'}$, and $R^{4'}$ are each independently halogen, —R', —CN, —NO$_2$, —OR', or —NR'$_2$, or
$R^{2'}$ and $R^{3'}$ together with the carbon form an optionally substituted 3-7 membered cycloalkyl or heterocycle ring.

28. A compound of embodiment 26, wherein the carbon attached to the OH group has an (S) configuration.

29. A compound of either of embodiments 26-27, wherein $R^{1'}$ is cyano.

30. A compound of any of embodiments 26-28, wherein $R^{2'}$ is $C_{1-6}$ aliphatic.

31. A compound of any of embodiments 26-29, wherein $R^{2'}$ is methyl.

32. A compound of any of embodiments 26-30, wherein $R^{3'}$ is $C_{1-6}$ aliphatic.

33. A compound of any of embodiments 26-31, wherein $R^{3'}$ is methyl.

34. A compound of any of embodiments 26-32, wherein $R^{4'}$ is $C_{1-6}$ aliphatic.

35. A compound of any of embodiments 26-33, wherein $R^{4'}$ is methyl.

What is claimed is:

1. A compound of the following structure:

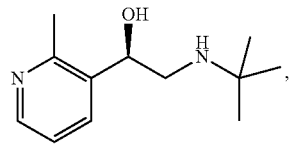

or a pharmaceutically acceptable salt thereof.

2. The compound of claim 1, wherein said compound is a pharmaceutically acceptable salt of

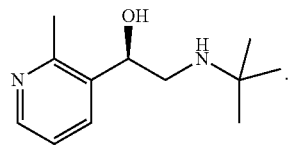

3. The compound of claim 1 of the following structure:

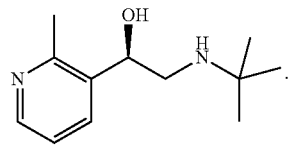

4. A pharmaceutical composition comprising a compound of the following structure:

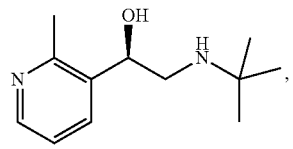

or a pharmaceutically acceptable salt thereof, and a pharmaceutically acceptable carrier.
5. The pharmaceutical composition of claim 4, wherein the compound is a pharmaceutically acceptable salt of
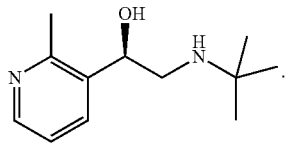
6. The pharmaceutical composition of claim 4, wherein the compound is of the following structure:
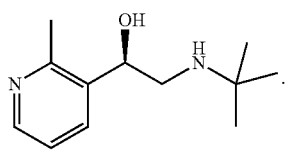
* * * * *